United States Patent [19]

Brois

[11] Patent Number: 5,646,098
[45] Date of Patent: Jul. 8, 1997

[54] CARBONYL CONTAINING COMPOUNDS AND THEIR DERIVATIVES AS MULTIFUNCTIONAL FUEL AND LUBE ADDITIVES

[75] Inventor: Stanley J. Brois, Westfield, N.J.

[73] Assignee: Exxon Chemical Patents Inc, Linden, N.J.

[21] Appl. No.: 242,750

[22] Filed: May 13, 1994

Related U.S. Application Data

[63] Continuation-in-part of Ser. No. 48,625, Apr. 16, 1993, abandoned, which is a continuation-in-part of Ser. No. 927,990, Aug. 11, 1992, abandoned, which is a continuation of Ser. No. 844,064, Mar. 2, 1992, abandoned, which is a continuation-in-part of Ser. No. 775,878, Oct. 11, 1991, abandoned, which is a continuation-in-part of Ser. No. 556,243, Jul. 23, 1990, Pat. No. 5,057,564.

[51] Int. Cl.$^6$ .................. C10M 159/12; C10M 129/86; C10M 139/00

[52] U.S. Cl. .................. 508/189; 508/190; 508/198; 508/221; 508/222; 508/452; 508/575; 525/374; 525/375; 525/383; 525/385; 526/213; 526/269; 528/222; 544/221; 546/13; 546/155; 548/110; 548/544; 549/4; 549/285; 549/292; 549/295; 560/170; 560/174; 560/190; 562/567; 562/578; 562/590; 564/160; 568/1; 568/3; 568/376; 568/379

[58] Field of Search ............... 546/13, 155; 548/110, 548/544; 549/4, 285, 292, 295; 568/1, 3, 376, 379; 525/383, 375, 374, 385, 386; 526/213, 269; 528/222; 544/221; 560/170, 174, 190; 562/567, 578, 590; 564/160; 252/32, 49.6, 51.5 R, 52 R, 56 R; 508/189, 190, 198, 221, 222, 452, 575

[56] References Cited

U.S. PATENT DOCUMENTS

| | | | |
|---|---|---|---|
| 3,087,936 | 4/1963 | Le Suer | 260/326.3 |
| 3,115,398 | 12/1963 | Thayer | 44/66 |
| 3,322,670 | 5/1967 | Burt et al. | 252/49.6 |
| 3,328,463 | 6/1967 | Lee et al. | 260/566 |
| 3,344,069 | 9/1967 | Stuebe | 252/49.6 |
| 4,011,167 | 3/1977 | Chibnik et al. | 252/42.7 |
| 4,025,445 | 5/1977 | Hellmuth et al. | 252/49.6 |
| 4,328,113 | 5/1982 | Horodysky et al. | 252/49.6 |
| 4,329,239 | 5/1982 | Chou | 252/51.5 A |
| 4,474,670 | 10/1984 | Braid et al. | 252/32.7 E |
| 4,474,671 | 10/1984 | Herd et al. | 252/33.6 |
| 4,524,004 | 6/1985 | Horodysky | 252/32.7 E |
| 4,524,005 | 6/1985 | Horodysky | 252/49.6 |
| 4,529,529 | 7/1985 | Horodysky | 252/49.6 |
| 4,566,984 | 1/1986 | Bush | 252/140 |
| 4,599,183 | 7/1986 | Horodysky et al. | 252/32.7 E |
| 4,925,983 | 5/1990 | Stockel | 564/8 |
| 4,961,868 | 10/1990 | Doner et al. | 252/32.7 E |
| 5,057,564 | 10/1991 | Brois | 524/101 |
| 5,084,194 | 1/1992 | Doner et al. | 252/32.7 E |
| 5,211,860 | 5/1993 | Doner et al. | 252/32.7 E |
| 5,274,051 | 12/1993 | Brois et al. | 525/383 |
| 5,277,833 | 1/1994 | Song et al. | 252/56 R |
| 5,288,811 | 2/1994 | Brois | 525/383 |

FOREIGN PATENT DOCUMENTS

| | | | |
|---|---|---|---|
| 650770 | 11/1964 | Belgium | C10M 133/58 |
| 099478A3 | 2/1984 | European Pat. Off. | C08C 19/00 |
| 105772 | 4/1984 | European Pat. Off. | C07C 49/245 |
| 0132383A2 | 1/1985 | European Pat. Off. | C10M 133/52 |
| 264247 | 4/1988 | European Pat. Off. | C10M 129/95 |
| 2344625 | 3/1977 | France | C10L 1/18 |
| WO91/16408 | 10/1991 | WIPO | C10L 1/22 |
| WO95/15303 | 6/1995 | WIPO | C07C 59/21 |

OTHER PUBLICATIONS

Chemical Abstracts, vol. 81, No. 18, Nov. 4, 1974, Columbus, Ohio, U.S. Abstract No. 108403y, Zalukaev et al. "Lubricating Composition" p. 175, col. 2.

*Primary Examiner*—Jerry D. Johnson
*Attorney, Agent, or Firm*—Harvey L. Cohen

[57] ABSTRACT

The invention relates to novel compositions comprising ene and free radical adducts of unsaturated and saturated hydrocarbons, and acyclic and cyclic vicinal polycarbonyl compounds such as diethyl ketomalonate and indantrione. The adducts are reacted with nucleophiles such as amines, electrophiles such as anhydrides and esters, and metal ions. Post-products are obtained via reaction of said products with capping reagents such as boric acid. Compositions containing said adducts, products and post-products include oleaginous substances such as fuels and lube oils.

11 Claims, No Drawings

CARBONYL CONTAINING COMPOUNDS AND THEIR DERIVATIVES AS MULTI-FUNCTIONAL FUEL AND LUBE ADDITIVES

RELATED APPLICATIONS

The application is a continuation in part of U.S. Ser. No. 048,625, filed Apr. 16, 1993 and now abandoned; which is a continuation-in-part of U.S. Ser. No. 927,990, filed Aug. 11, 1992, abandoned; which is a Rule 60 continuation of U.S. Ser. No. 844,064, filed Mar. 2, 1992, abandoned; which is a continuation-in-part of U.S. Ser. No. 775,878, filed Oct. 11, 1992, abandoned; which is a continuation-in-part of U.S. Ser. No. 556,243, filed Jul. 23, 1990, U.S. Pat. No. 5,057,564.

FIELD OF THE INVENTION

This invention relates to novel carbonyl containing compounds and their derivatives as additives useful in oleaginous compositions such as fuels, lubricants, power transmission fluids, and the like.

BACKGROUND OF THE INVENTION

Oleaginous substances have found wide use in contemporary industry. Unfortunately, many oleaginous compositions contain additives that from an environmental viewpoint could be improved. For example, many additives used today contain chlorine which is environmentally undesirable. Therefore, there is a need for chlorine-free additives. Also, many of today's high performance applications for oleaginous compositions require additives that can meet multi-functional requirements. Therefore, any environmentally acceptable additives for oleaginous compositions should preferably provide the benefits of multi-functional properties.

One approach to providing such additives for oleaginous compositions is to take advantage of the unique multi-functional properties of the novel carbonyl compounds described hereinafter by preparing oleaginous compositions containing the chlorine-free adducts and derivatives of this invention.

Organic compounds containing two or more carbonyl groups in a row are generally referred to as vicinal polycarbonyl (VP) monomers. When the vicinal polycarbonyl (VP) group forms part of an acyclic hydrocarbon structure, such compounds are generally referred to as acyclic VP monomers. When the polycarbonyl group forms part of a cyclic structure, such compounds are generally referred to as cyclic VP monomers.

The reactions of VP monomers with unsaturated hydrocarbons, including unsaturated hydrocarbon polymers, will produce carbonyl containing adducts as disclosed in U.S. Pat. No. 5,057,564 and Application Ser. No. 935,604. These adducts are referred to herein as ene adducts.

More recently, various hydrocarbons, and especially saturated hydrocarbons, and saturated hydrocarbon polymers, have been found to react with VP monomers in the presence of a free radical initiator. These compounds are disclosed, for example, in U.S. Pat. Nos. 5,288,811, and 5,274,051, and are referred to herein as radical adducts.

By means of this present invention, it is possible to provide improved oleaginous compositions such as fuels, lube oils, and the like, by incorporating into these compositions additives selected from ene adducts, radical adducts, derivatives of said adducts, and mixtures thereof.

SUMMARY OF THE INVENTION

Simply stated, the present invention relates to novel compounds referred to herein as "ene and radical adducts," novel compounds derived from said ene and radical adducts, and are referred to herein as "products," and novel compounds derived from said products, and referred to herein as "post-products," their method of preparation, and compositions containing the same. Thus, non-limiting embodiments of the invention include: (a) oleaginous compositions containing a major amount of an oleaginous substance and a minor amount of an ene or radical adduct of at least one VP monomer and a hydrocarbon having a number average molecular weight ($M_n$) in the range of about 200 to about 10 million; (b) oleaginous compositions comprising a major amount of an oleaginous substance and a minor amount of a product formed by reacting: (i) a compound selected from the group consisting of ene and radical adducts, with (ii) a compound selected from the group consisting of amines, polyamines, amino alcohols, alcohols, polyols, hydrazines, derivatives of hydrazines, hydroxylamines, semicarbazides, hydrides, cyanohydrins, phosphites, carbon acids and metal ions; and (c) oleagineous compositions comprising a major amount of an oleaginous substance and a minor amount of a post-product formed by reacting: (i) a compound selected from the group consisting of ene and radical adducts, with (ii) a compound selected from the group consisting of amines, polyamines, amino alcohols, alcohols, polyols, hydrazines, derivatives of hydrazines, hydroxylamines, semicarbazides, hydrides, cyanohydrins, phosphites, and carbon acids to form a product; and then reacting said product with (iii) borating, acylating, and thio acid reagents, as well as metal ions to form a post-product.

In a special embodiment of the present invention, chlorine-free dispersants are provided comprising adducts of VP monomers and polyisobutylenes, ethylene alpha-olefin copolymers, ethylene butene copolymers, poly-alpha-olefins, and poly-n-butenes having $M_n$ values ranging from about 500 to about 20,000 (20K) that have been aminated with polyamines, such as tetraethylene pentamine.

These and other embodiments will be set forth in greater detail in the general description which follows.

General Description

In its broadest sense, the present invention is concerned with a new family of compounds consisting of (a) ene and radical adducts having one or more VP monomers per adduct, (b) products derived from said ene and radical adducts, and (c) post-products derived from said products, which are useful in oleaginous compositions, especially as multifunctional additives, dispersants, and dispersant viscosity modifiers. The adducts are prepared via the ene and radical addition of VP monomers to unsaturated and saturated hydrocarbons and polymers respectively, with $M_n$ values ranging from about 200 to about 10 million. Moreover, the hydrocarbon and polymer reactants may contain one or more polar substituents, provided that the polar substituents are compatible with the ene and radical chemistry involved in the functionalization with VP monomers. The adducts can be further reacted with a variety of nucleophiles, electrophiles, and metal ions to form products which in turn can be reacted with borating reagents, thio acids, and metal ions to form post-products. Each of these will be described hereinafter. Also, oleaginous compositions containing the adducts, products, and post-products are encompassed within this invention. Oleaginous substances include fuels, oils, and other lubricants such as greases. Non-limiting examples include diesel, jet, and motor fuels, gasoline, heating fuels, and the like; lubricating oils, transmission fluids, hydraulic fluids, functional fluids, and the like.

Ene Adducts

The ene adducts, 1a, 2a, and 3a, of the instant invention are produced by reacting one or more cyclic or acyclic VP monomers, 1, 2, and 3, respectively, with an unsaturated hydrocarbon or unsaturated polymer according to the following equations:

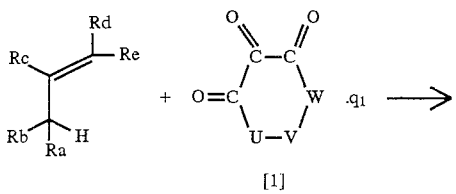

[1]

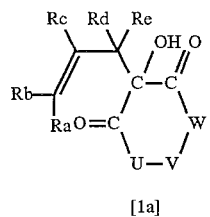

[1a]

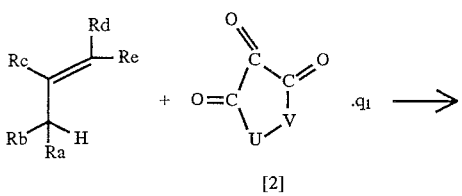

[2]

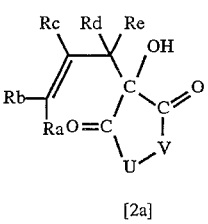

[2a]

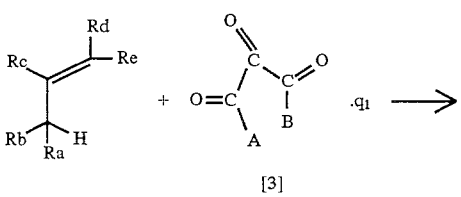

[3]

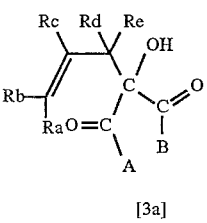

[3a]

wherein $R_a$, $R_b$, $R_c$, $R_d$, and $R_e$ are independently selected from the group consisting of: H, alkyl groups having about 1 to about a million carbon atoms; alkenyl groups having about 3 to about a million carbon atoms; substituted alkyl and alkenyl groups having one or more substituents selected from the groups consisting of $HO(CH_2CH_2O)_x$ where x is an integer ranging from 1 to about 10; $OR_f$, $COOR_f$ wherein $R_f$ is independently selected from the group consisting of: H, alkyl radicals having about 1 to about 18 carbon atoms; aryl and substituted aryl groups; $C(=O)R_g$, $OC(=O)R_g$, wherein $R_g$ is selected independently from the group consisting of alkyl radicals having 1 to about 18 carbon atoms, aryl radicals, and substituted aryl radicals; CN; heteroaryl radicals ($R_h$) wherein $R_h$ is independently selected from the group consisting of radicals of 5 or 6 membered heterocyclic and fused heterocyclic rings which are derived from furan, thiophene, imidazole, triazole, oxazole, thiazole, thiadiazole, indole, benzofuran, benzimidazole, benzoxazole, benzotriazole, benzothiazole, purine, xanthine, pyridine, pyrimidine, pyrazine, triazine, quinoline, isoquinoline, phthalazine, quinazoline, quinoxaline, and phenanthroline; aryl, and ethylenically unsaturated groups; q is selected from the group consisting of $H_2O$, and alcohols, especially MeOH, EtOH, and n-BuOH; i is a numerical value ranging from from 0 and a number greater than zero; U, V and W are independently selected from the group consisting of C=O, C=NR$_f$, NR$_f$, O, S, CHR$_g$, C(R$_g$)$_2$ and CHCHOHCH$_2$OH; and in which U and V may be dependently selected so that U+V=1,2-phenylene, naphthalene-1, 2-diyl, and 1,2-dihydroxy-ethylene-1,2-diyl; and wherein A and B are independently selected from OR$_f$, N(R$_g$)$_2$, COOR$_f$, and C(=O)R$_g$ wherein R$_f$ and R$_g$ are as defined above.

Typical cyclic VP monomers include alloxan (AX), 1,3-dimethyl-alloxan, indan-1,2,3-trione (IT), naphthalene-1,2,3,4-tetrone, cyclopentane-1,2,3-trione, cyclohexane-1,2,3-trione, furan-2,3,4-trione, benzopyran-2,3,4-trione, benzothiopyran-2,3,4-trione, quinoline-2,3,4-trione, rhodizonic acid, croconic acid, triquinoyl, leuconic acid, isopropylidene ketomalonate, dehydroascorbic acid, and their hydrates, alcoholates and solyates. Useful derivatives of indantrione include 5-methoxy-, 5-methylthio-, 5-dimethylamino-, and 5-phenyl-indantrione; 4-aza-indantrione, thieno[f]indantrione, benzo[f]indantrione, and their hydrates.

Typical acyclic VP monomers include ketomalonic acid; amides, and esters of ketomalonic acid including alkyl and aryl esters such as diethyl ketomalonate (KM); diketosuccinic acid; alpha, beta-diketo acids and their ester and amide derivatives; polyketone monomers such as dimethyl, diphenyl, di-tolyl, and di-mesityl tri-ketones and tetra-ketones.

Multiple Ene Adducts

Depending on reaction conditions, but primarily on reactant ratios, more than one VP monomer selected from 1, 2, and 3, may be appended to ene-reactive sites present in the previously described unsaturated hydrocarbons and polymers to afford 1y, 2y and 3y (shown below) wherein $R_y$ is the radical corresponding to the unsaturated hydrocarbyl group, and U, V, W, A and B are as previously defined; and n is a numerical value ranging from 1 to about twenty, and even greater depending on the level of unsaturation and the $M_n$ of the hydrocarbon or polymer.

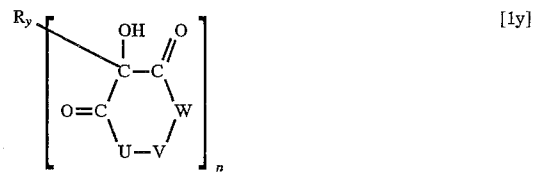

[1y]

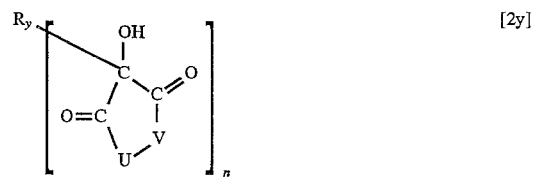

[2y]

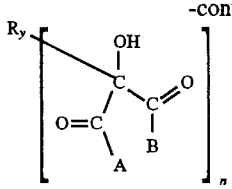

[3y]

Mixtures of ene adducts of mono-unsaturated polymers wherein n averages from about 1.2 to about 1.8, are useful multi-functional additives per se, as well as invaluable precursors to highly potent dispersants with outstanding high and low temperature viscometrics.

Also, a plurality of VP monomers can be ene-added to poly-unsaturated substrates, such as dienes, trienes, and polyenes, as well as polymers with multiple double bonds such as polybutadiene, polyisoprene, and terpolymers such as ethylene propylene terpolymers containing about 5 to about 10 wt.% of termonomers such as 5-ethylidene-2-norbornene (ENB). For example, an EPDM terpolymer with an $M_n$ of about 50K, containing 5 wt.% ENB which corresponds to about twenty double bonds per chain, can add at least one VP monomer per double bond to give functionalized polymers bearing approximately twenty VP monomers (n=20 in the above formulae). For other poly-unsaturated polymers such as polybutadiene and polyisoprene having $M_n$ values above a million, n can exceed a hundred.

Unsaturated Substrates

In general, the olefinic hydrocarbons and polymers with which the VP monomers of the present invention are to be reacted are well known in the art. These oil soluble olefinic compounds comprise substantially saturated hydrocarbon backbones, yet they have a minor amount of ethylenic unsaturation which is available for adduct formation by means of the thermal ene addition process. Thus, the hydrocarbon or polymer should preferably be substantially saturated, i.e., a substantial portion of the total number of carbon-to-carbon covalent linkages are saturated linkages.

Olefins which form useful ene adducts with VP monomers will typically be long chain, straight, and/or branched alkenes consisting of about 10 or more carbon atoms, so as to provide suitable oil solubility. Useful alkenes include $C_{12}$ to $C_{30}$ olefins, such as dodecene-1, dodecene-6, 2-methylundecene-2, 2-methylundecene-4, 6-methylundecene-5, 2-ethyldecene-1, 2,3-dimethyldecene-1, 2,5-dimethyldecene-2, 2-propylnonene-1, 4-propylnonene-3, 2,5,8-trimethylnonene-4, 2-butyloctene-1, 3-butyloctene-1, 4-butyloctene-2, 7-methyl-4-propyloctene-3, 3,6-diethyloctene-4, 2,6-dimethyl-3-isopropylheptene-2, 2,4,4-tri-methyl-3-ethylheptene-2, 3,4,5-trimethyl-5-ethylheptene-3, 2,2,3,5,6-pentamethylheptene-3, 2,5-dimethyl-3-isobutylhexene-2, 2,2,3,4,5,5-hexamethyl-hexene-3, 2,4,4-trimethyl-3-tert-butyl-pentene-2, tridecene-1, tridecene-6, 3-methyldodecene-3, 6-ethyl-undecene-5, 5-butylnonene-4, 3-propyl-2-tert-butylhexene-1, tetradecene-1, tetradecene-7, 4-methyltridecene-4, 2,3-dimethyl-dodecene-3, 6-propylundecene-5, 4-pentylnonene-3, 5-butyldecene-4, 2-pentylnonene-1, 3-pentylnonene-1, 2-hexyloctene-1, 4,5-dipropyloctene-4, pentadecene-1, pentadecene-6, 3,7,11-trimethyl-dodecene-1, 6-butylundecene-5, 5-pentyldecene-4, hexadecene-1, 9-methylpentadecene-6, 5-butyldodecene-4, 6-pentylundecene-5, 2,8-dimethyl-5-isoamylnonene-4, heptadecene-1, heptadecene-8, 5,9,13-trimethyltetradecene-1, octadecene-1, octadecene-9, 2-methyl-heptadecene-2, nonadecene-1, 2-methylnonadecene-1, 3-ethyl-octadecene-2, 3-ethyloctadecene-2, 5,7,9-trimethylheptadecene-4, 3,7,11,15-tetramethylhexadecene-2, 5-butylhexadecene-4, 2-octyl-dodecene-1, heneicosene-9, docosene-1, 4-propylnonadecene-3, tri-cosene-11, 2-methyltricosene-2, 5-butyleicosene-4, hexacosene-1, 2-methyl-5-isoamyleicosene-4, heptacosene-1, heptacosene-13, octacosene-1, 10-nonylnonadecene-9, hentriacontene-1, hentriacontene-15, 3-pentadecyloctadecene-2, and pentatriacontene-17; and diolefins such as hexadecadiene-1,15, eicosadiene-1,19, 2,19-dimethyl-eicosadiene-1,19, and octahydrosqualene. Oligomers of $C_3$ to $C_{12}$ olefins, preferably of $C_3$ to $C_8$ olefins, both alpha-olefins and internal olefins are also useful. These preferably include from 2 to 8 repeating units, as typified by pentaisobutylene and octapropylene, and trimers of alpha-olefins such as 1-decene.

Other useful unsaturated substrates can incorporate one or more polar groups. In this instance, the optimal number and type of polar groups attached to the alkene depends upon the oil solubility of the adducts with VP monomers, as well as their effectiveness as additives. Useful olefins containing one or more polar groups include unsaturated alcohols such as beta-citronellol, geraniol, nerol, nerolidol, dihydromyrcenol, 5-decene-1-ol, 9-decen-1-ol, 2,4,6-tri-methyl-1,6-heptadiene-4-ol, 10-undecen-1-ol, 7-dodecen-1-ol, 8,10-dodecadiene-1-ol, 11-tetradecen-1-ol, 7-tetradecen-1-ol, 9-tetra-decen-1-ol, farnesol, 11-hexadecen-1-ol, 9-octadecen-1-ol, oleyl alcohol, 13-docosen-1-ol, 1,1-diallyl-1-docosanol, phytol, para-menth-1-en-9-ol, alphaterpinol, dihydrocarveol, isopulegol, carveol, paramenth-6-ene-2,8-diol, retinol, and cholesterol; ethers: such as 7, 9-dioxa-1-dodecene, tetraethylene glycol diallyl ether, Brij 92, and Brij 99; carboxylic acids, esters and amides such as undecenylic acid, 2-dodecenyl succinic acid, myristoleic acid, palmitoleic acid, oleic acid, elaldic acid, linoleic acid, vaccenic acid, arachidonic acid, erucic acid; ethyl undecenylate, methyl 9-hexadecenoate, methyl oleate, vaccenic acid methyl ester, methyl 11-eicosenate, methyl linoleate, methyl linolinate, dimethyl brassylate, triolein; N,N-dimethyl 10-undecenamide, N,N-bis-(2-hydroxyethyl)-oleamide, N,N-dimethyl erucamide, N-methyl-2-dodecenyl-succinimide, and N-ethyl-2-octadecenylsuccinimide; sulfides, sulfur-oxygen, and phosphorus compounds such as 7-octenyl methyl sulfide, 10-undecenyl methyl sulfide, methyl oleyl sulfide, benzyl oleyl sulfide and phenyl oleyl sulfide; ethyl oleyl sulfone, phenyl 10-undecenyl sulfone; oleyl methanesulfonate; diethyl 7-octenyl phosphonate, dimethyl oleylphosphonate, and trioleyl phosphate; alkene-substituted aromatics, and heteroaromatics, such as 10-undecenyl benzene, oleylbenzene, oleyl 2-furoate, 10-undecen-1-yl 2-thiophenecarboxylate, 10-undecen-1-yl 3-indolecarboxylate, 2-(10-undecen-1-yl) amino-benzimidazole, 2-oleylthio-benzothiazole, 5-(4-pyridyl)-2,7-nonadiene, 4-(10-undecenyl) pyridine, 10-undecenyl pyrazine, and 5-(10-decenyl) amino-1,10-phenanthroline.

An especially useful group of unsaturated reagents amenable to the ene process of the present invention is cited in "McCutcheon's Emulsifiers and Detergents", 1986 North American Edition, McCutcheon Division, MC Publishing Co., Glen Rock, N.J. A variety of unsaturated anionic, nonionic, cationic, and amphotheric emulsifiers and detergents having a range of HLB values from 0.8 to about 42.0 can be functionalized with the ene reactive VP monomers of the present invention to produce useful additives for fuels and lubes. Included are unsaturated alkanolamides, amine oxides, sulfonated amines and amides, betaines, ethoxylated alcohols, amines, amides, fatty acids, and fatty esters; fatty esters, glycerol esters, glycol esters, imidazolines, lecithins, monoglycerides, phosphates, phosphate esters, propoxylated and ethoxylated fatty acids and alcohols; sarcosine derivatives, sorbitan derivatives, sucrose esters, sulfates and sulfonate derivatives, and sulfosuccinates.

Examples of useful unsaturated emulsifiers and detergents include lecithin, glycerol trioleate, sorbitan trioleate, diethylene glycol dioleate, glycerol monooleate, glycerol dioleate, glycerol ricinoleate, polyethylene glycol (100) monooleate, polyoxyethylene (2) oleyl ether, N,N-dimethyl oleamide, oleyl dimethylamine oxide, oleyl alkanolamide, oleic isopropanolamide, N,N-bis(2-hydroxyethyl) oleamide, ethoxylated oleylamine, linolenic diethanolamide, phosphated oleyl ethers, oleamide sarcosine, N,N-dimethyl undecylenamide, rape seed oil, castor oil, pentaerythritol monooleate, PEG 400 dioleate, PEG 200 monooleate, triglycerol monooleate, sucrose ricinoleate, propylene glycol monoricinoleate, ethyoxylated oleic acid, ethoxylated castor oil, PEG 400 monooleate, polyoxyethylene(10) oleyl alcohol, tall oil monooleate, polyoxyethylene(20) sorbitan monooleate, and polyoxy ethylene(20) oleyl alcohol. Usually, a suitable combination of unsaturated detergents and VP monomers will lead to adducts for fuel and lube applications especially in fossil fuel, and alcohol burning engines. Moreover, the polyamine-treated adducts will also serve as useful additives.

Oil soluble olefinic polymers which form useful ene adducts will generally have a number average molecular weight ($M_n$) of about 500 to about 20K when the ene adducts are used for dispersant and detergent applications, and from about 10K to about one million, and most generally from about 20K to about 200K for dispersant-viscosity improver applications. For the latter applications, polymers useful as V.I. improvers will be used in forming the ene adducts. Preferred V.I. improver polymers will generally have a narrow range of molecular weight, as determined by the ratio of weight average molecular weight ($M_w$) to number average molecular weight ($M_n$). Polymers having a $M_w/M_n$ of less than about 10, for example from about 1 to about 4 are most desirable.

The olefinic polymers useful in this invention may be essentially amorphous in character, including those with up to about 25 percent by weight of crystalline segments as determined by x-ray or differential scanning calorimetry. Additionally, the polymers may be of any of the tapered or block copolymers known in the prior art or the copolymers of alpha-olefins comprised of chains of intra-molecularly heterogenous and inter-molecularly homogenous monomer units, such as those prepared by the process of U.S. Pat. No. 4,540,753.

Specific examples of suitable hydrocarbon polymers include homopolymers and copolymers of one or more monomers of $C_2$ to $C_{30}$, e.g., $C_2$ to $C_8$ olefins, including both alpha-olefins and internal olefins, which may be straight or branched, aliphatic, aromatic, alkylaromatic, and cycloaliphatic. In one preferred embodiment, these will be polymers of ethylene with $C_3$ to $C_{30}$ olefins, preferably copolymers of ethylene and propylene, and more preferably, copolymers of ethylene and butene. Examples of polymers of other olefins include polymers of ethylene or polymers of propylene which contain nonconjugated diolefins, such as 1,4-hexadiene. Also included are polymers of butene, isobutylene, polymers and copolymers of $C_6$ and higher alpha-olefins, particularly useful examples being polybutenes, polyisobutylenes, copolymers of propylene and isobutylene, copolymers of isobutylene and butadiene, and the like.

Other suitable hydrocarbon polymers containing olefinic unsaturation well known in the art include those which may be described as hydrogenated or partially hydrogenated homopolymers, and random, tapered or block polymers (copolymers, including terpolymers and tetrapolymers) of conjugated dienes and/or monovinyl aromatic compounds with, optionally, alpha-olefins or lower alkenes e.g., $C_3$ to $C_{18}$ alpha-olefins or lower alkenes. The conjugated dienes include isoprene, butadiene, 2,3-dimethylbutadiene, piperylene and/or mixtures thereof. The monovinyl aromatic compounds are preferably monovinyl monoaromatic compounds, such as styrene or alkylated styrenes substituted at the alpha-carbon atoms of the styrene, such as alpha-methylstyrene, or at ring carbons, such as methylstyrene, ethylstyrene, propyl-styrene, isopropyl-styrene, butyl-styrene, isobutylstyrene, and tert-butylstyrene. Alpha-olefins and lower alkenes optionally included in these random, tapered and block copolymers preferably include ethylene, propylene, butene, ethylene-propylene copolymers, isobutylene, and polymers and copolymers thereof. As is also known in the art, these random, tapered and block copolymers may include relatively small amounts, that is less than about 5 mole %, of other copolymerizable monomers such as vinyl pyridines, vinyl lactams, methacrylates, vinyl acetate, vinyl stearate, and the like. Specific examples include random polymers of butadiene and/or isoprene and polymers of isoprene and/or butadiene and styrene. Typical block copolymers include polystyrene-polyisoprene, polystyrene-polybutadiene, polystyrene-polyethylene, polystyrene-ethylene propylene copolymer, polyvinyl cyclohexane-hydrogenated polyisoprene, and polyvinyl cyclohexane-hydrogenated polybutadiene. Tapered polymers include those of the foregoing monomers prepared by methods known in the art. Useful polymers include styrene-butadiene block and tapered copolymers. Examples of suitable normal block copolymers as set forth above include hydrogenated styrene-isoprene block copolymers.

The present invention also includes star polymers as disclosed in patents such as U.S. Pat. Nos. 3,711,406, 4,108,945, 4,116,917, 5,049,294 and 5,070,131. Particularly useful are star branched polyisoprene polymers, since they offer several advantages over other polymers used in producing multigrade oils. For example, star branched polymers are often less sensitive to degradation by shearing which is a very desirable property in lube formulations. Moreover, the star branched polyisoprene polymers feature low intrinsic viscosities even at high molecular weight. Finally, star polymers which are functionalized according to the ene process of the present invention do not suffer substantial breakdown. Usually, these star polymers will contain a substantial number of functional groups per unit volume as well as a uniform distribution of such functional groups.

The term copolymer as used herein, unless otherwise indicated, is thus meant to include terpolymers, and tetrapolymers of ethylene, $C_3$ to $C_{28}$ alpha-olefins, non-conjugated diolefins, and mixtures of such diolefins, and of isobutylene with $C_4$ to $C_{18}$ non-conjugated diolefins, and mixtures of such diolefins. The amount of non-conjugated diolefin will generally range from about 0.5 to 20 wt percent, and preferably from about 1 to about 10 wt percent, based on the total amount of ethylene and alpha-olefin present.

Representative examples of non-conjugated dienes that may be used in forming adducts targeted for use as dispersant viscosity modifiers (VM's), include acyclic dienes such as: 1,4-hexadiene; 1,5 heptadiene; 1,6-octadiene, 5-methyl-1,4-hexadiene, 3,7-dimethyl-1,6-octadiene, and mixed isomers of dihydro-myrcene; alicyclic dienes such as: 1,4-cyclo-hexadiene, 1,5-cyclooctadiene, 1,5-cyclododecadiene, 4-vinylcyclohexene, 1-allyl-4- isopropylidene cyclohexene, 3-allylcyclopentene, 4-allyl cyclohexene, and 1-isopropenyl-4-butenyl-cyclohexene; and alicyclic fused and bridged ring dienes such as tetrahydroindene, dicyclo-pentadiene, bicyclo[2.2.1]hepta-2,5-diene, 5-methylene-6-methyl-2-norbornene, 5-propenyl-2-norbornene, 5-(1-cyclopentenyl)-2-norbornene, and most preferably, 5-ethylidene-2-norbornene.

Polymers derived from butadiene, and isoprene such as polybutadiene, and polyisoprene having $M_n$ ranging from about 50K to about 10 million including natural rubber, are also useful.

Ene Adduct Formation

The ene adducts of the present invention can be prepared by various processes in which the unsaurated hydrocarbon or polymer, and the VP monomers are intimately intermixed and reacted at a temperature at which thermal ene addition occurs without appreciable decomposition. This, of course, is possible in accordance with the present invention because of the high reactivity of the VP monomers. Generally, reaction temperatures within the range of from about 20° C. to about 200° C. are useful. The reaction temperature will vary depending upon the particular unsaturated hydrocarbon or polymer and VP monomer that are employed. Effective mixing of the olefinic polymer and the VP monomer can be achieved by combining these reactants together with a solvent, or neat as described below.

Solution

The ene adducts can be prepared in solution, in which case, the unsaturated hydrocarbon or polymer substrate is dissolved in a solvent such as toluene, xylene, synthetic oil, mineral oil or other suitable solvents, and mixtures thereof, and the VP monomer is added as is, or as a solution, to the dissolved hydrocarbon. The mixture can then be reacted at temperatures of about 50° C. to about 200° C. for several hours (reaction is monitored by IR analysis) in the substantial absence of air, preferably under a blanket of inert gas, such as nitrogen until ene adduction is complete. Optionally, a trace of an antioxidant such as BHT (butylated hydroxy toluene) can be used.

Typically, the ene adducts are separated from the reaction mixture by stripping off the solvent, and further diluted with appropriate lubricating oil packages for desired intermediate or end use purposes. Ene and radical adducts formed in mineral or synthetic oils can be used directly in product forming reactions, or a specific ene use.

The proportions in which the reactants of the present invention are to be used can vary according to the particular olefinic hydrocarbon employed, but normally will range between about 0.01 and 3, and preferably between about 0.1 and 2 moles of the VP monomer per mole of ethylenic unsaturation in the polymer. The degree of ethylenic unsaturation of the polymer is measured by several methods which are known to those of ordinary skill in this art, among which are included nuclear magnetic resonance (NMR), calibrated infrared spectroscopy, refractive index comparisons (particularly for ethylene-propylene-norbornene terpolymers), and calibrated iodine titration measurements.

It is important to note that polyfunctional adducts with n ranging from about 1.1 to about 1.8 (average number of functional groups per chain) prepared from mono-unsaturated polymers afford highly useful additives and additive precursors, owing to their outstanding V.I. properties. Usually, n will be dictated by the number of C=C bonds present in the unsaturated reactant, and the reactant ratio. Thus, a high VP monomer/olefin ratio usually affords high n values owing to multiple ene reactions on each reactive olefinic site. It is notable that with terpolymers containing about 20–40 olefinic sites, n values of about 20–40 or greater can be obtained.

Neat

When the mixture of hydrocarbon and VP monomer has sufficiently low melt viscosity for effective mixing, they may be reacted without a solvent in a stirred mixer or in a masticator. In a typical stirred mixer experiment,a neat polyolefin such as ethylene butene-1 copolymer ($M_n$ of approximately 2K, and about 55 wt % ethylene), and an equimolar amount of VP monomer such as IT, or AX, are combined in a nitrogen-purged reactor and stirred at about 160° C. for about 6 hours, or until infrared analysis indicates complete reaction. Ene adduct formation is usually quick and quantitative, and multiple ene adductions can be achieved by using an excess of the VP monomer.

In a typical masticator experiment, a polyolefin such as ethylene propylene 5-ethylidene-2-norbornene (ENB) terpolymer (EPDM) with $M_n$ of approximately 50K and containing about 5 wt % ENB, and 10 mg of BHT inhibitor are placed into a Braebender mechanical mixer at about 160° C. Subsequently, about 2 wt %, (based on polymer weight), of IT monomer is added in small portions over a two minute span under moderate mixing conditions (40 rpm) to give a purple colored mixture. Within 2 minutes, the color changes to a golden yellow indicating that ene addition of IT to the EPDM copolymer is complete. After mixing for several more minutes, the modified polymer is dissolved in hexane. Complete dissolution of the EPDM-IT adduct in cyclohexane, indicates that no crosslinking occurs during functionalization. The addition of the polymer solution to a large excess of acetone precipitates the EPDM-IT adduct. Oxygen analysis of the dried polymer indicates virtually complete utilization of IT in the grafting process. Reaction times will of course vary with the nature and amount of polymer, the VP monomer, the reactant ratio and melt reaction conditions, and accordingly, IR analysis for example, is useful to ascertain complete reaction. This melt grafting protocol is applicable to the design of a wide range of IT-polymer adducts which are useful, per se, as antioxidant-viscosity modifiers. As a precursor to dispersants, EPDM-IT adducts are readily aminated with N-(3-aminopropyl) morpholine for example, in the melt at about 120° C. to about 150° C. to produce antioxidant bound dispersant-viscosity modifiers which do not tend to thicken or gel on aging for extended (over 60 days) periods.

Radical Adducts

The radical adducts of the present invention are prepared by reacting a cyclic or acyclic VP monomer with a hydrocarbon or polymer in the presence of a free radical initiator according to the equation:

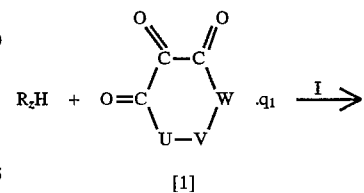

[1]

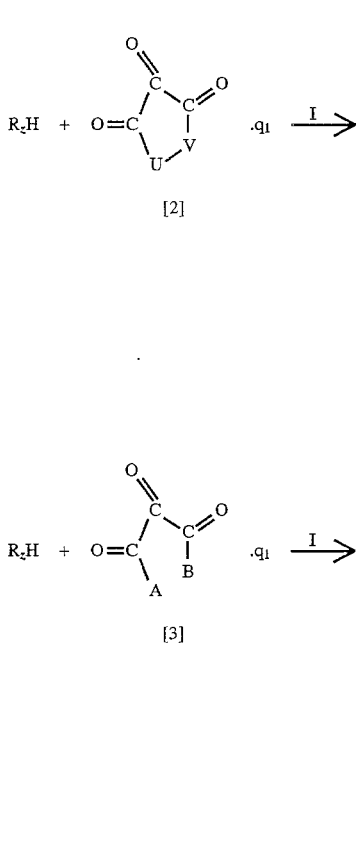

wherein 1, 2 and 3 were previously described, and 1b and 2b represent cyclic radical adducts, and 3b represents an acyclic radical adduct. $R_z$ represents the hydrocarbyl radical derived from the hydrocarbons and polymers described below; "I" represents the free radical initiator; and n is a numerical value ranging from about one to about 20 and even greater with polymers having higher $M_n$ values exceeding 50K; q and i are defined above.

Useful free radical initiators, I, essential to the formation of the radical adducts of this invention include dialkyl peroxides such as di-tertiary-butyl peroxide, 2,5-dimethyl-2,5-di-tertiary-butyl-peroxy-hexane, di-cumyl peroxide; alkyl peroxides such as tertiary-butyl hydroperoxide, tertiary-octyl hydroperoxide, cumene hydroperoxide; aroyl peroxides such as benzoyl peroxide; peroxyl esters such as tertiary-butyl peroxypivalate, tertiary-butyl perbenzoate; and azo compounds such as azo-bis-isobutyronitrile. Any free radical initiator with a suitable half life at the reaction temperatures between about 80° C. and 200° C. can be used, as well as ionizing radiation.

The radical-initiated reaction of VP monomers can be applied to a wide spectrum of hydrocarbons ($R_zH$) selected from the group consisting of (a) normal alkanes such as decane, hexadecane, octadecane, tricosane, and paraffins having abaout 10 to about 40 carbons; branched alkanes such as trimethyldecane, tetramethylpentadecane (pristane); squalane, white oils, Nujols, mineral oils, hydrogenated oligomers and co-oligomers of ethylene, propylene, butylene and higher molecular weight olefin oligomers having 10 to about 40 carbons; (b) substituted hydrocarbons consisting of normal and branched alkanes with about 10 to about 40 carbons may feature one or more functional groups such as $OR_f$, $O(CH_2CH_2O)_xH$ wherein x is an integer ranging from about 1–10; CN, $COOR_f$, $C(=O)R_g$, aryl, and ethylenically unsaturated groups; useful substituted hydrocarbons comprise decanol, octadecanol, ethoxylated octadecanol, stearic acid, ethyl stearate, methyl decyl ketone, tetrapropylbenzene, and polyesters; (c) polymers derived from one or more of the following monomers: ethylene, propylene, butenes, higher alpha-olefins, styrene, allyl esters, vinyl esters such as vinyl acetate, acrylic acid, acrylonitrile, and the like. Polymers can be linear or branched, with $M_n$ values ranging from about 500 to about 10 million. Homo-polymers of ethylene such as high and low density polyethylene, atactic or crystalline polypropylene, polybutene, polyisobutylene, homopolymers and copolymers of higher alpha-olefins, copolymers of ethylene with propylene, EPR, which may also contain unconjugated dienes (EPDM), copolymers of ethylene with butenes or higher alpha-olefins, copolymers of propylene with butenes, and higher alpha-olefins. When dienes such as butadiene and isoprene are used in copolymer formation, the resulting polymers are preferably hydrogenated to saturate substantially all of the ethylenic unsaturation. Useful polymers include hydrogenated poly-alpha-olefins, styrene butadiene and/or isoprene block, and tapered copolymers; hydrogenated styrene isoprene block, and hydrogenated star branched polyisoprene polymers. Since polymers containing excess ethylenic unsaturation are prone to crosslinking reactions during radical grafting, polymers containing only residual levels of ethylenic unsaturation are preferred. The polymers described above for ene adductions leading to 1a, 2a, and 3a are useful, per se; however, the hydrogenated versions of these polymers, are most preferred.

Radical Adduct Formation

The radical-induced reactions of VP monomers with hydrocarbon and/or polymer substrates can occur in the neat state, in a melt, or in solution; bulk modifications can be effected in polymer processing equipment such as a rubber mill, an extruder, and a Brabender or Banbury mixer.

Neat

Radical grafting of hydrocarbons, and saturated polymers, as well as substituted hydrocarbons, and polymers is conveniently conducted without a solvent or diluent. For example, a neat hydrocarbon such as pristane, or a neat polyester basestock, and about 2 wt % (based on hydrocarbon weight) of a monomer such as II, are combined in a nitrogen-blanketed reactor, at about 160° C. Radical grafting is intiated by adding in one dose, about 1–100 wt % (based on monomer weight) of a free radical initiator such as t-butyl peroxide for example, and stirring the mixture at 160° C. until the color of the mixture changes from green to gold, or IR analysis indicates that radical grafting is complete.

Melt.

Radical grafting of high molecular weight polymers may also be conducted without a solvent, as in a melt, and is a preferred route to multifunctional viscosity improvers (MFVI). To this end, polymer processing equipment such as a rubber mill, an extruder, a Banbury mixer, Brabender mixer, and the like are used. When radical grafting is conducted in bulk, reaction temperatures ranging from about 90° C. to about 220° C., and reaction times ranging from about 1 minute to about 1 hour are employed. For example, a saturated polymer such as ethylene propylene (EP) copolymer with $M_n\approx 50K$ is charged into a Braebender melt mixer at a temperature of about 170° C. Moderate mixing conditions (40 rpm) are employed. Subsequently, a suitable VP monomer such as IT hydrate is added (about 2 to about 5 wt % based on the polymer weight) in 2–3 portions over a ca. two minute span. The polymer melt rapidly turns a brilliant purple color owing to the dehydration of IT to its anhydrous form. No further color changes occur even after extended mixing times, indicating an absence of reaction. However, when a radical initiator such as t-butyl peroxide (about 1–100 wt % based on monomer weight), is slowly added to the purple reaction mixture, and the mixing speed increased to 100 rpm, the polymer mixture turns yellow within a few minutes, thus indicating that the IT monomer is consumed in the radical reaction with the saturated EP copolymer (IR analysis confirms the visual endpoint). Complete dissolution of the functionalized polymer in heptane confirms that the melt reaction conditions do not crosslink the IT-modified EP polymer. The addition of the heptane solution of the polymer to a large volume of acetone effectively precipitates the polymer. After repeating this procedure, the IT-modified polymer is vacuum dried at 60° C. for 48 hours. Oxygen analyses consistently show complete IT monomer utilization in the modification of EP copolymer. UV-GPC analysis indicates that the IT monomer appears to be randomly distributed on the EP copolymer backbone.

In the melt grafting process of the instant invention, reaction times will vary with the nature and amount of polymer, the VP monomer, the reactant ratio and melt reaction conditions, and accordingly, IR analysis for example, is used to ascertain complete reaction.

The melt functionalization protocol for producing radical adducts is quite general, and is applicable to a wide range of polymers, copolymers, block and graft copolymers. The IT-functionalized polymers are useful in their own right as antioxidants, but can be aminated with polyamines such as N-(3-aminopropyl)morpholine or 3-(dimethylamino)-propylamine in the melt, or in solution, to produce antioxidant bound dispersant-viscosity modifiers for use in lubricants.

Solution

Typically, when grafting in solution, the polymer is dissolved in a suitable solvent, such as chlorobenzene, dichlorobenzene, or mineral oil, and heated to temperatures ranging from about 90° C. to about 180° C. depending upon the radical initiator used. The VP monomer is added and heated for a suitable period to free any radical-reactive carbonyl groups which may be tied up as a hydrate, alcoholate, or polar solvate. At this point, the radical initiator is added in one dose, or dropwise over a suitable time span, usually from about 5 to 60 minutes. Another option is to add a mixture of compatible monomer and peroxide in a suitable solvent to the hydrocarbon or polymer solution at an addition rate and suitable reaction temperature consistent with the half life of the radical initiator. The reaction mixture is heated, with stirring, until visual color changes, infrared analysis, and/or NMR analysis indicate that the radical addition of the VP monomer to the hydrocarbon is complete. In the case of purple-colored IT, the visible color change from lavender to amber that occurs during radical grafting, provide a convenient method for monitoring the reaction. Depending on the temperature and concentration, reaction times of about 0.05 to about 12 hours are usually sufficient to achieve high conversions to the radical adducts.

In general, the amount of VP monomer employed is dictated by the level of functionality desired in radical adducts while still maintaining sufficient oil solubility. Levels of radical grafting onto hydrocarbons and polymers ranging from about 1 to 2 VP monomers per each hydrocarbon chain or a polymer chain segment containing about 20 to about 200 carbons, are useful. For example, each chain of a saturated ethylene propylene (EP) copolymer with $M_n\approx 50K$ and about 55% propylene, contains about twenty functional groups resulting from the radical addition of a VP monomer such as KM, IT or AX. The optimal level of functionality as indicated before, is usually dictated by a suitable degree of oil solubility. Normally, the high efficiency of radical grafting of cyclic VP monomers onto hydrocarbons and polymer substrates do not usually require stripping or filtering procedures. Functionality levels leading to desirable chain extension are preferred when designing dispersants, and multifunctional additives.

When necessary, functionalized products can be isolated by solvent removal using evaporative techniques, or in the case of functional polymers, by adding the reaction mixture to polar solvents such as acetone and methanol, which effectively precipitate the functionalized polymers.

The amount of free radical initiator used is generally between 1 and 100 wt % based on the weight of VP monomer, and often depends upon the nature of the free radical initiator, and hydrocarbon or polymer substrate being grafted. The susceptibility of certain polymers to undergo crosslinking and/or chain scission necessitates careful discretion regarding reagent concentrations, time, temperature, and process conditions since these parameters are all dependent variables in the grafting process. Carefully balancing these parameters should help to retain the integrity of the polymer during radical grafting. Ordinarily, grafting processes which use from about 1 wt.% to about 100 wt.% levels of free radical initiator (based on monomer weight), at grafting temperatures from about 80° C. to about 180° C. in an oxygen-free reactor can produce functional polymers with significant levels of appended VP monomers. The level of functionality is crucial to the design of dispersant viscosity improvers with optimal viscometrics and performance, and the radical process of the present invention allows one to tailor a functional polymer for specific fuel and lube uses.

Products

The adducts of this invention have value as additives, especially as multifunctional additives, and lubricant compositions containing 1c, 2c, and 3c constitute a significant part of this invention. These and other uses are described hereinafter in the Section headed: "Additive Uses." In addition, the ene and radical adducts identified by 1c, 2c and 3c are highly versatile precursors to new and useful products. Thus, one or more ene and radical adducts can be reacted with a wide assortment of nucleophiles, electrophiles, and metal salts to produce a highly useful array of products: 1d, 2d, and 3d, as illustrated below:

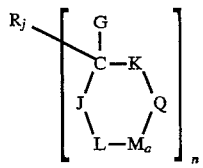

[1d]

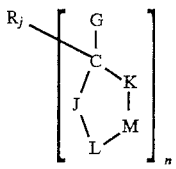
[2d]

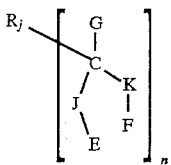
[3d]

wherein $R_j$ is selected from the group consisting of saturated and unsaturated hydrocarbyl groups containing from about 10 to about 40 carbon atoms; polyalkyl and polyalkenyl groups of $M_n$ ranging from about 200 to about 10 million, each of which may contain one or more functional groups selected from the groups consisting of HO, HO(CH$_2$CH$_2$O)$_x$; OR$_g$, COOR$_f$, C(=O)R$_g$, aryl, and heteroaryl (R$_h$) groups wherein x is an integer ranging from about 1 to about 10, and R$_g$, R$_f$, and R$_h$ are as previously defined. The integer, n, can vary from about 1 to about a thousand or greater depending upon the $M_n$ of the hydrocarbon; G is selected independently from the group consisting of OH, OC(=O)R$_g$, OB(OR$_g$)$_2$, OP(OR$_g$)$_2$, OP[=O](OR$_g$)$_2$, and R$_g$ is defined above.

When J and K are attached to carbon atoms, they are independently selected from the group consisting of C=O, C(OR$_g$)$_2$, CHOH, C=NR$_g$, CHNHR$_g$, C=NR$_k$, and CHNHR$_k$ wherein R$_k$=CH$_2$CH$_2$OH, C(CH$_2$OH)$_3$, and CH$_2$CH$_2$SH; C=NR$_1$ wherein R$_1$=OH, NHR$_f$ and NHR$_h$; C=NR$_m$ wherein R$_m$=ureido, thioureido, and guanidino; C=NR$_n$, and CHNHR$_n$, wherein R$_n$=3-dimethylaminopropyl, and 3-(4-morpholinyl)propyl; C=NR$_o$, and CHNHR$_o$, wherein R$_o$=NH$_2$CH$_2$CH$_2$, NH$_2$CH$_2$CH$_2$CH$_2$, NH$_2$(CH$_2$CH$_2$NH)$_x$$_{CH2}$CH$_2$, and x is an integer ranging from about 1 to 10; C(Σ)—OH, and C(Σ)NHR$_g$, wherein Σ is selected from the group consisting of CN, and P(=O)[OR$_g$]2; C=CΩ$_2$ wherein Ω is selected from the group consisting of CN, and COOR$_g$; moreover, L, M, and Q are independently selected from the group consisting of C(R$_f$)$_2$, J and K; in addition, L and M is also selected dependently from the group consisting of 1,2-phenylene, and 1,2-dihydroxyethylene-1,2-diyl; however, when attached to heteroatoms, J and K are C=O, and M$_a$ is independently selected from the group consisting of C=O, C=NR$_f$, and C(R$_f$)$_2$; moreover, L, M and Q can be independently selected from O, NR$_f$, and N-m, wherein m is selected from the group consisting of Li, Na, K, Ca/2, Mg/2, Ba/2 and Cu/2; when a is zero, M is deleted in (1d), J and K are C=O, and L and Q are independently selected from the group consisting of OR$_f$, O-m, OCH$_2$C(CH$_2$OH)$_3$, NHC(CH$_2$OH)$_3$, NHR$_n$, and NHR$_o$; also, L and Q are selected dependently from NHCH$_2$CH$_2$NHCH$_2$CH$_2$CH$_2$NHCH$_2$CH$_2$NH, and NH(CH$_2$CH$_2$NH)$_x$CH$_2$CH$_2$NH, wherein x is an integer ranging from about 1 to about 10.

Again, when attached to heteroatoms in 3d, J and K are C=O, and E and F are independently selected from the group consisting of OR$_f$, O-m, OCH$_2$C(CH$_2$OH)$_3$, NHC(CH$_2$OH)$_3$, NHR$_n$, and NHR$_o$; also, when J and K are C=O, E and F are selected dependently from NHCH$_2$CH$_2$NHCH$_2$CH$_2$CH$_2$NHCH$_2$CH$_2$NH, and NH(CH$_2$CH$_2$NH)$_x$CH$_2$CH$_2$NH, wherein x, m, R$_f$, R$_n$, and R$_o$ are defined above.

When 2 or more ene adducts are condensed with polyamines, amino alcohols or polyols, coupling and chain extension can occur. With polyfunctional dispersant polymers containing one double bond per chain, wherein n averages about 1.1 to about 1.8 functional groups per chain, chain extension occurs, and often enhances dispersant performance.

Highly preferred dispersant products are prepared via the amination of ene adducts of IT monomer and R$_p$H, wherein R$_p$H comprises a group of unsaturated polymers consisting of polyisobutylene, poly-n-butene, poly-alpha-olefin, ethylene propylene, and ethylene butene-1 copolymers having $M_n$ values of from about 500 to about 20K, and having about one double bond per chain.

Especially preferred dispersant viscosity modifier products are prepared via ene and radical are designated by R$_q$H, and are selected from the group consisting of ethylene propylene 5-ethylidene 2-norbornene terpolymers, ethylene propylene copolymers, partially hydrogenated star-branched polyisoprene, and styrene butadiene block and tapered copolymers having $M_n$ values of about 20K to about 500K.

Preferred products of the present invention for use as dispersants and V.I.-dispersants, are 2d (shown above) wherein R$_j$=polyalkyl, and polyalkenyl, with $M_n$ ranging from about 500 to about 100K, J and K are independently selected from the group consisting of C=O, C=NR$_n$ and C=NR$_o$, where L+M=1,2-phenylene; also, 1d wherein a is zero and M is deleted, G=OH, J and K are C=O, and L and Q are selected independently from the group consisting of OR$_f$, NHR$_n$, and NHR$_o$; also, L+Q are dependently selected from NHCH$_2$CH$_2$(NHCH$_2$CH$_2$CH$_2$NHCH$_2$CH$_2$NH, and NHCH$_2$CH$_2$(NHCH$_2$CH$_2$)$_x$CH$_2$CH$_2$NH, wherein x is an integer ranging from 1 to about 10.

Still other preferred dispersant products are prepared by reacting 1 to 2 moles of adducts derived from KM, IT and AX and ethylene butene copolymers with $M_n$ ranging from about 1K to about 20K, and n averaging from about 1.2 to about 1.8, with about one to two moles of a polyamine such as tetraethylene pentamine.

Product Formation

The products of this invention are preparedly reacting a wide assortment of ene and radical adducts with selected nucleophiles, electrophiles and metal ions according to the following protocol:

Adducts of hydrocarbons and polymers derived from:

[i] vicinal polyketones such as indantrione (IT), naphthalene 1,2,3,4-tetrone, rhodizonic acid, triquinoyl, croconic acid, leuconic acid, dimethyl triketone, and diphenyl triketone;

[ii] vicinal polycarbonyl containing amides such as alloxan (AX), 1,3-dimethylalloxan, quinoline-2,3,4 -trione; and

[iii] vicinal polycarbonyl containing esters , and lactones, such as isopropylidene ketomalonate, furan-2,3,4-trione, benzopyran-2,3,4-trione, dehydroascorbic acid and its derivatives, and diethyl ketomalonate (KM);

when reacted with:

[a] nucleophiles such as amines, hydrazines, alcohols, water, polyamines, polyols, amino alcohols, amino thiols, and dithiols;

[b] electrophiles such as acylating agents like carboxy anhydrides and esters, borate esters, phosphite and phosphate esters; and

[c] metal salts and metal complexes;

produce a wide assortment of products consisting of antioxidants, antioxidant-dispersants, dispersant viscosity modifiers, detergents, and multi functional additives for fuels and lubes.

It was found that the structure, and yield of products derived from the chemistry outlined above are a sensitive function of reagent structure, and reaction parameters. The structures depicted for the characterized products illustrate in part, the multiple reaction pathways involved in product formation. When polyfunctional adducts are used in the foregoing reactions, related products, some of which can be chain extended in nature, and not easily defined, will often be present. Suffice it to say that the products derived from 1c, 2c, and 3c via reaction with the nucleophiles, electrophiles, and metal salts and metal complexes, can be mixtures, and that these mixtures although complex, are highly useful as fuel and lube additives.

Typically the reactions are conducted by contacting, e.g., mixing, the adduct with the nucleophile, electrophile, or metal reagent as the case may be, neat or in a suitable solvent at a temperature, and time sufficient to form the product. The precise conditions for carrying out the reactions are not critical, and illustrative examples are given in the experimental section of this specification.

Useful electrophiles

Typically, electrophilic reactions will usually involve the hydroxyl group attached to the ene or radical adduct. Useful electrophiles for reacting with adducts to from products include carboxylic acids, anhydrides, and esters, phosphites, phosphates, boric acid, and borate esters Useful metal salts, and complexes Useful metals that react with adducts include alkali metals such as lithium, sodium, potassium; alkaline earth metals such as calcium, magnesium, barium; and transition metals such as copper, nickel, and cobalt. Useful carriers (counter ions) for the alkali and alkaline earth metals include acetate, carbonate, bicarbonate, and oxide counter ions; carriers for the transition metals include acetate ion, and oxygen-containing ligands such as acetylacetone (2,4-pentanedione).

Useful nucleophiles

For convenience, useful nucleophiles are grouped into mono-reactive nucleophiles, such as monoamine, hydrazine, and monohydric alcohol reagents, and poly-reactive nucleophiles such as polyamine, amino alcohol, and polyol reagents. Examples of each of these reagents follow.

Monoamine reagents

Useful amines feature a $NH_2$ or NH group capable of reacting with the adducts of the present invention. The $NH_2$ or NH functional group can be attached to linear and/or branched alkanes having from about 1 to 100 carbons. Moreover, the $NH_2$, NH, or aminoalkyl groups can also be attached to homocyclic rings such as a cycloalkane having from 3 to about 18 members, aromatic rings, or fused aromatic rings as typified by benzene and naphthalene, respectively; heterocyclic rings, or fused heterocyclic rings having 5 or 6 members consisting of carbon, nitrogen, oxygen and sulfur as typified by pyrrole, furan, thiophene, imidazole, imidazoline, triazole, tetrazole, oxazole, thiazole, thiazoline, indole, benzofuran, benzothiophene, indazole, benzimidazole, benzotriazole, benzoxazole, purine, pyridine, pyridazine, pyrimidine, pyrazine, quinoline, isoquinoline, cinnoline, phthalazine, quinoxaline, phenanthroline; hydrogenated versions of the above described heterocycles; and N-oxide, nitroxyl, proxyl, and tempo derivatives. Other useful amine reactants can be selected from a wide assortment of heterocycles wherein the reactive NH functional group is actually a member of a heterocyclic ring having from about 3 to about 18 members selected from the group consisting of C, N, O, and S, as exemplified by morpholine and thiomorpholine.

Moreover, the presence of substituents(functionality) in all of the above described amines is sometimes desirable, since the substituents of the present invention may impart useful multifunctional properties to the resulting products. Useful substituents include: ethers, polyethers, $R_gO(\omega O)_x\omega O$—, wherein $R_g$ is defined above, and $\omega$ is selected from the group consisting of ethylene, propylene, trimethylene, butylene, and tetramethylene, and x is an integer ranging from 1 to about 10; thioethers and polythioethers (replace O by S in the above formula); carboxy, carboxamide and nitrile groups; sulfur-oxygen substituents such as sulfoxide, sulfone, sulfonic acid, sulfonate ester, sulfonamide, and sulfate groups; phosphorus-oxygen substituents such as phosphoric acid, phosphonic acid, thiophosphoric acid, and thiophosphonic acid groups. The presence of these substituents in amine containing alkanes, homocycles, and heterocycles imparts new and useful properties to the additive products.

Examples of useful amines wherein the amino group is attached to linear and branched alkanes and cycloalkanes, and their substituted derivatives include: methyl, ethyl propyl, butyl, amyl, hexyl, heptyl, octyl, decyl, undecyl, dodecyl, tridecyl, tetradecyl, pentadecyl, hexadecyl, octadecyl, eicosyl, docosyl, and tricosylamine; isopropyl, isobutyl, sec-butyl, tert-butyl, 2-ethyl-propyl, S-(–)-2-methylbutyl, isoamyl, 1,2-dimethylpropYl, tert-amyl, 3,3-dimethylbutyl, 2-heptyl, 3-heptyl, 2-ethylhexyl, 1,5-dimethylhexyl, t-octyl, 2-decyl, 2-tetradecyl, 7-tetradecyl, 2-hexadecyl, 7-heptadecyl, 2-octadecyl, 9-octadecyl, 2-methyl-2-nona-decyl, 2-eicosyl, 9-heneicosyl, 2-docosyl, 2-octacosyl, 2-tri-cosyl, and 7-tricosylamine; dimethyl, diethyl, methylpropyl, methylisopropyl, dipropyl, diisopropyl, methylbutyl, dibutyl, di-sec-butyl, diisobutyl, dipentyl, dihexyl, dioctyl, bis-(2-ethyl-hexyl), didecyl, methyloctadecyl, dioctadecyl, didocosyl, diocta-cosyl, and ditricosylamine; cyclopropyl, cyclopentyl, cyclohexyl, dicyclohexyl, 4-methylcyclohexyl, cycloheptyl, cyclooctyl, cyclododecyl, (R)-(+)-bornyl, (–)-cis-myrtanyl, 1-adamantyl- and 2-adamantylamine. Useful substituted amines include: methoxy, ethoxy, 2-methoxyethyl, 3-methoxypropyl, 3-butoxypropyl, and 3-isopropoxypropylamine; glycine, iminodiacetic acid, sarcosine, alanine, leucine, beta-alanine, 4-aminobutyric acid, 8-amino-caprylic acid, 12-aminododecanoic acid, aspartic acid, glutamic acid, 3-aminoadipic acid, cysteine, penicillamine, homocysteine, S-methylcysteine, ethioneine, asparagine, glutamine, arginine, cyan-amide, 3,3'-iminodipropionitrile, taurine, 3-aminopropanesulfonic acid, 2-aminoethyl- phosphonic acid, 3-aminopropylphosphonic acid, and 6-amino-1-hexylphosphate and 1-amino-1-cyclohexanecarboxylic acid.

Examples of useful amines wherein an amino group or aminoalkyl group is attached to homocycles such as benzene and fused aromatic rings like naphthalene, and their substituted derivatives include: aniline, 4-methyl- 4-butyl, 4-hexyl-, 4-octyl, 4-decyl, 4-dodecyl, 4-tetradecyl, 4-hexadecyl, 4-cyclohexyl aniline; p-methoxy, 4-butoxy, 4-hexyloxy and 4-methylmercaptoaniline; 5-aminoindan, 5-methoxy-2-methylaniline, 2,4-dimethoxyaniline, 2-aminobiphenyl, 4-phenoxyaniline, 4-(2-aminoethyl)benzenesulfonamide, 1-amino-naphthalene, 2-aminonaphthalene, benzylamine, aminodiphenylmethane, tritylamine, 2,2-diphenylamine, phen-ethylamine, 3-phenyl-propyl-amine, 3,3-diphenylpropylamine, 4-phenylbutylamine, 2-ethoxybenzylamine, 2-methoxyphenethyl amine, 3,5-dimethoxybenzylamine, piperonylamine, 3,4-di-benzyloxyphenethylamine, 2,4,6-trimethoxy-benzylamine, 1-naphthyl methylamine, 1-aminofluorene and 9-amino-fluorene.

Examples of useful amines wherein an amino group or an aminoalkyl group is attached to a heterocycle, a substituted heterocyclic, or a fused heterocycle include: furfurylamine, 2-amino-2-thiophene-carboxylic acid, 3-thiophenemethylamine, 3-aminopyrazole, 2-aminoimidazole, 1-(3-aminopropyl)imidazole, histamine, histidine, 3-amino-1,2,4-triazole, 3-amino-5-mercapto-1,2,4-triazole, 5-amino-3-methylisoxazole, muscimol, ibotenic acid, 5-amino-3-methyl-isothiazole, 2-aminothiazole, 2-amino-5-phenyl-thiazole, 2-amino-4-phenyl-5-tetradecylthiazole, 2-amino-4-thiazole-acetic acid, 2-amino-1,3,4-thiadiazole, 5-amino-1,3,4-thiadiazole-2-thiol, 5-amino-3-phenyl-1,2,4-thiadiazole, indoline, tryptamine, alpha-methyltryptamine, 6-methoxytryptamine, tryptophan, tetrahydro iso quinoline, phenoxazine, phenothiazine, 2-aminobenzimidazole, 2-[aminomethyl] benzimidazole, 2-amino-benzoxazole, 2-aminobenzothiazole, adenine, 2-aminopurine, 8-azaadenine,2-aminopyridine, 2-aminoethylpyridine, 2-aminopyrimidine, 4-aminopyrimidine, 4-amino-2-mercaptopyrimidine, cytosine, 5-aminouracil, aminopyrazine, 3-amino-1,2,4-triazine, 5-azacytosine, 3-aminoquinoline, 1-aminoisoquinoline, 4-amino-tempo, and 3-aminomethyl-1-proxyl.

Examples of useful amines wherein the amino group is a member of a heterocyclic ring include: aziridine, 2-methylaziridine, azetidine, pyrrole, pyrrolidine, pyrazole, imidazole, 2-ethyl-imidazole, 1H-1,2,3-triazole, 1,2,4-triazole, 1H-tetrazole, thi-azolidine, piperidine, 4-methyl piperidine, 4-phenylpiperidine, 4-benzylpiperidine, morpholine, 2,6-dimethylmorpholine, thio-morpholine, hexamethyleneimine, heptamethyleneimine, 1-aza-12-crown-4, 1-aza-15-crown-5, and 1-aza-18-crown-6; substituted heterocycles include pyrrole-2-carboxylic acid, ethyl 4-pyrazole-carboxylate, 2 -mercaptoimidazole, 4-phenylimidazole, tolazoline, urocanic acid, 4,5-dicyanoimidazole, and 1,2,3-triazole-4,5-di-carboxylic acid.

Reaction of the above amines with adducts 1c, 2c and 3c, depending on reaction conditions, produces a wide assortment of useful amide, imide and imine derivatives. The reduction of the imines with boranes affords useful amine products.

Hydrazines

Hydrazines useful in the present invention include hydrazine groups attached to alkanes, homocyclics, and heterocyclics as described above. Accordingly, the conversion of many of the above amine derivatives via suitable N-aminating agent, as in the preparation of N-aminoazoles as described in "Advances in Heterocylic Chemistry" volume 53, pages 85–231 (1992), affords useful hydrazines. Examples of useful hydrazines include hydrazine, 1,1-dimethylhydrazine, 2-hydroxyethylhydrazine, 1-aminopyrrolidine, N-aminopyrazole, N-aminoindazole, N-aminoimidazole, N-aminobenzimidazole, N-amino-1,2,3-triazole, N-aminobenzotriazole, N-aminotetrazole, N-aminothiazole, thiadiazole, and oxazole; 1-aminopiperidine, 1-aminohomopiperidine, 4-aminomorpholine, semi-carbazide, carbohydrazide, thiosemicarbazide, 4-ethyl-3-thiosemicarbazide, thiocarbohydrazide, aminoguanidine, 2-hydrazine-2-imidazoline, phenylhydrazine, 1,1-diphenylhydrazine, 4-methoxy-phenyl-hydrazine, 4-phenyl-semicarbazide, 4-phenylthiosemicarbazide, benzenesulfonylhydrazide, 2-furoic hydrazide, 2-thiophenecarboxylic hydrazide, 4-amino-1,2,4-triazole, purpald, 2-hydrazino-pyridine, isonicotic hydrazide, 4-hydrazinoquinoline, hydralazine, dansyl hydrazine, 9-aminotheophylline, and N-aminopurines.

Reaction of the above hydrazines with adducts 1c, 2c and 3c of the present invention affords useful hydrazide and hydrazone products. Reduction of certain hydrazones with borohydride, for example, gives useful substituted hydrazine derivatives.

Monohydric Alcohols

Monohydric alcohols useful in the present invention include hydroxy alkanes, hydroxy and hydroxyalkyl containing homocycles, and heterocycles as well as their substituted derivatives by analogy with the amines described above.

Examples of useful alkanols and substituted alkanols include butyl, hexyl, octyl, decyl, dodecyl, tetradecyl, hexadecyl, octadecyl, eicosyl, docosyl, hexacosyl and triacontanyl alcohol; 2-methyl-1-pentyl, 2-propyl-1-pentyl, 3,7-dimethyl-1-octyl alcohol; 2-hexyl, 2-octyl, 4-decyl, 2-dodecyl, 2-hexadecyl alcohol; useful alicyclic alcohols include cyclopropylmethyl, cyclopentyl, cyclohexyl, cyclohexylmethyl, dicyclohexylmethyl, cycloheptyl, cycloheptylmethyl, cyclooctyl, cyclododecyl, cyclododecylmethyl, 2-norbornanemethyl, fenchyl, myrtanyl, decahydro-2-naphthyl, 1-adamantyl and 1-adamantylmethyl alcohol; useful substituted alcohols include 2-ethoxyethanol, 2-butoxyethanol, 2-(2-ethoxy-ethoxy) ethanol, diethylene glycol dodecyl ether, dipropylene glycol methyl ether, triethylene glycol monomethyl ether, Brij 30, 35, 58, 78, Triton X-100, and 114; glycidol, 3-hydroxy-tetrahydrofuran, glycerol formal; 2-mercaptoethanol, 2,3-dimercapto-1-propanol, 2-methylthioethanol, 1,5-dithiacyclooctan-3-ol; glycolic acid, 12-hydroxydodecanoic acid, methyl glycolate, ethyl 6-hydroxyhexanoate, alpha-hydroxy-gamma-butyrolactone, 2-methylsulfonylethanol, and isethionic acid; useful aromatic-substituted alcohols include: phenol, 3-pentadecylphenol, 4-cyclopentylphenol, 4-butoxyphenol, 3,3-dimethoxyphenol, 1-naphthol, 4-benzyloxyphenol, benzyl alcohol, 1-phenyl-1-decanol, benzhydrol, 4-butylbenzyl alcohol, 4-butoxy-benzyl alcohol, 3,4,5-trimethyoxybenzyl alcohol, 4-chromanol, 2-biphenylmethanol, 2-naphthalene-ethanol, 9-fluorenemethanol, di-benzosuberol, phenethyl alcohol, 4-phenyl-1-butanol, 6-phenyl-1-hexanol, and 3,4-dimethoxyphenethyl alcohol; 2-phenylthioethanol, thiochroman-4-ol, 4-hydroxyacetophenone, 4-hydroxybenzophenone, 4-hydroxybenzoic acid, salicylic acid, 1-hydroxy-2-naphthoic acid, methyl 4-hydroxyphenyl acetate, methyl salicylate, and methyl 4-hydroxymethyl benzoate; useful heterocyclic-substituted alcohols include furfuryl alcohol, 3-thiophenemethanol, 4-hydroxytempo, and 3-pyridylcarbinol N-oxide.

Polyreactive nucleophiles

Polyamines, amino alcohols, and polyols

In a highly preferred embodiment of the present invention, polyamines, amino alcohols, and polyhydric alcohols are reacted with the ene and radical adducts to give a wide variety of useful products.

An important feature of polyreactive nucleophiles is their ability to couple two or more adducts together thereby chain extending the product, and oftimes enhancing the viscometric properties of the product. Moreover, the presence of multiple functionality in the radical and ene adducts leads to even more pronounced $M_n$ increases, and enhanced V.I. performance owing to the ability of polyamines to induce chain extension via reaction with multiple functional groups attached to the adducts. As described previously, polyfunctionality in the adducts is obtained by control of stoichiometry and reaction conditions during ene and radical addition of the carbonyl monomers to polymers. In addition, the presence of polyamine chains increases basicity, and imparts valuable chelation properties which in additive applications, enhances dispersant and detergent activity. The possibility of adverse interactions of additives containing basic nitrogen with fluoro elastomer seals, for example, can be obviated by acylation, boration or other post-treatment protocols described below.

Polyamines

Useful polyamines and substituted polyamines feature two or more amino groups selected from $NH_2$ and/or NH radicals which are capable of reacting with the adducts of the present invention. By analogy with monoamines, the amine groups can be attached to alkanes, homocycles, and heterocycles; in addition, the polyamine derivatives may also contain one or more substituents Useful polyamines feature two or more amino radicals such as $NH_2$ and/or NH, and are attached to alkanes or branched alkanes containing from about 2 to about ten thousand carbons. Polyamines capable of reacting with the adducts of the present invention are depicted by the formula:

$$\Psi_1 NH\text{-}\xi\text{-}N\text{-}\Psi_2\Psi_3$$

wherein $\Psi_1$, $\Psi_2$, and $\Psi_3$ are independently selected from the group consisting of H, alkyl having about 1–30 carbons, and $H(NH\omega)_x$; also, $\xi=\omega$ and $\omega(N[\phi]\omega)_x$ wherein $\phi=H$, and $\omega(NH\text{-}\omega)_x NH_2$; x is an integer ranging from one to about ten.

Other useful polyamines are those where the amino or aminoalkyl groups are attached to a homocycle, a heterocycle; or, wherein the NH groups of the polyamine are members of a heterocyclic ring having from about 6 to about 30 members. The cyclic polyamines may contain other heteroatoms such as oxygen and sulfur.

The presence of selected substituents in the polyamine can impart useful multifunctional properties to the products. Accordingly, substituents selected from: carboxylic acid, carboxamide and nitrile groups, as well as sulfur-oxygen groups, and phosphorus-oxygen groups are useful. Useful ethers, polyethers, thioethers, and polythioethers are described by the above formula where $\Psi_1$, $\Psi_2$ and $\Psi_3$ are selected from the group consisting of $R_f\Theta\text{-}(\omega\text{-}\Theta)_x\text{-}\omega\text{-}$, wherein $\Theta=$oxygen and/or sulfur.

Examples of polyamines bearing alkane and substituted alkane groups include: ethylenediamine (EDA), 1,3-propanediamine(PDA), 1, 2-propanediamine, 1,4-butanediamine, 2-methyl-1,2-propane-diamine, 1,3-pentanediamine, 1,5-pentane-diamine, 2,2-dimethyl-1,3-propanediamine, 1,6-hexane-di-amine, 2-methyl-1,5-pentane-di-amine, 1,7-heptanediamine, N-methyl-EDA, N-ethyl-EDA, N,N-dimethyl-EDA, N,N-diethyl-EDA, N,N-dibutyl-EDA, N-methyl-PDA, N-propyl-PDA, N,N-dimethyl-PDA, N,N-diethyl-PDA, N,N-dibutyl-PDA, diethylenetriamine (DETA), N-2-aminoethyl-1,3-propane-diamine, 3,3'-diamino-N-methyl-dipropylamine, 3,3'-imino-bis-propylamine, spermidine, bis-hexamethylentriamine, tri-ethylenetetramine(TETA), N,N'-bis-(3-aminopropyl) EDA, N,N'-bis(3-aminopropyl)-1,3-PDA, spermine, tris-2-amino-ethylamine, tetraethylenepentamine (TEPA), and pentaethylenehexamine (PEHA).

Useful examples of substituted polyamines include: ornithine, lysine, lanthionine, cystine, penicillamine disulfide, and diamino-pimelic acid.

For certain fuel and lube applications, "cascade-like" polyamines such as (CP-8) shown below, are quite useful in forming dispersant products which can chelate metals and interact with polar materials such as sludge and varnish precursors.

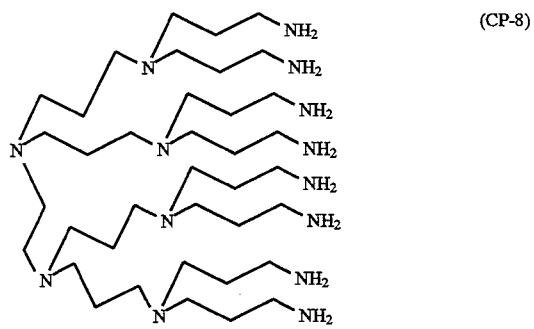
(CP-8)

The most preferred polyamines are the alkylene polyamines as typified by EDA, DETA, TEPA, PEHA, their higher molecular weight polyamine homologs, and commercial polyethylene polyamines such as "Polyamine H, Polyamine 400, and Dow Polyamine E-100."

Useful examples of polyamines containing homocyclic and heterocyclic groups, and substituted groups include: 4,4'-methylene-bis(cyclohexylamine), 1,2-diaminocyclohexane, 1,4-di-aminocyclohexane, 1,3-cyclohexane-bis-(methylamine), 1,4-cyclo-hexane-bis-(methylamine), N-cyclohexyl-PDA, and 1,3-adamantane-diamines; substituted aromatic polyamines: benzidine, 1,2-dianilinoethane, 2-aminophenyl disulfide, 4,4'-ethylenedianiline, 3,3'-methylenedianiline, 4,4'-methylenedianiline, o-tolidine, 4-aminophenyl disulfide, 3,3',5,5'-tetramethylbenzidine, 1,2-phenylenediamine, 3,3'-diaminobenzidine, 4-methoxy-1,2-phenyl-enediamine, 1,2,4,5-benzenetetramine, 1,3-phenylene diamine, 4-methoxy-1,3-phenylenediamine, 1,4-phenylenediamine, 4,4'diamino-di-phenylamine, N,N-diethyl-1,4-phenylenediamine, pararosaniline base, 3,3'dimethoxybenzidine, 3,3'dimethylnaphthidine, 2,3-diaminonaphthaline, 1,1'-binaphthyl-2,2'-diamine, 2,7-diamino-fluorene, 9,10-diaminophenanthrene, N-phenyl-EDA, 1,2-diphenyl-EDA, N,N'-dibenzyl-EDA, 1-phenylpiperazine, 4-aminophenyl sulfone, and 2,5-diaminobenzenesulfonic acid; useful substituted heterocyclics include: 1-(3-aminopropyl)imidazole, histamine, histidine, carnosine, 3,5-diamino-1,2,4-triazole, 2,4-diamino-5-phenyl-thia-zole, trypt-amine, 5-aminoindole, tryptophan, 5-aminoindazole, 6-aminopurine, adenine, guanine, 2-aminomethylpyridine, 2-(2-aminoethyl) pyridine, 2,6-diaminopyridine, 2,3-diamino-pyridine, 2,4-diaminopyrimidine, 2,4,6-triamino-pyrimidine, 2,4-diamino-6-mercaptopyrimidine, 4,5-diamino-2,6-dimercapto-pyrimidine, mel-amine, 4-aminoquinaldine, 8-amino-quinoline, 5-aminoisoquinoline, and thionin.

Useful examples of heterocycles wherein one or more of the NH groups of the polyamine are ring members include: 1-(2-aminoethyl)piperidine, 3-amino-piperidine, 4-aminomethyl-piperidine, 4-amino-2,2,6,6-tetramethyl piperidine, piperazide, 1-methylpiperazine, 1,4-diaminopiperazine, 1-(2-aminoethyl)-piperazine, 1,4-bis-(3-aminopropyl)-piperazine, tetra-hydro-pyrimidine, homopiperazine, 1,4,7-triazacyclononane,1,5,9-triazacyclo-dodecane, cyclen, 1,4,8,11-tetra-aza-cyclotetradecane, 1,4,-8,12-tetraazacyclopentadecane, hexacyclen, 4-(2-aminoethyl) morpholine, 4-(3-aminopropyl) morpholine, and 1,4,10-trioxa-7,13-di-aza-cyclo-pentadecane.

Useful examples of substituted polyamines containing polyether groups capable of complexing with alkali and alkaline earth metals, include: polyoxyethylene diamines, polyoxypropylene diamines, polyoxypropylene triamines as depicted below:

$NH_2\omega(O\omega)_xNH_2$ and $NH_2\omega(O\omega)_xCH_2C(\theta_1\theta_2)CH_2(O\omega)_xNH_2$ wherein $\theta_1$ and $\theta_2$ are independently selected from the group consisting of $R_p$ and $\omega(O\omega)_xNH_2$.

Other useful substituents which impart enhanced chelation properties to dispersants include carboxamido groups.

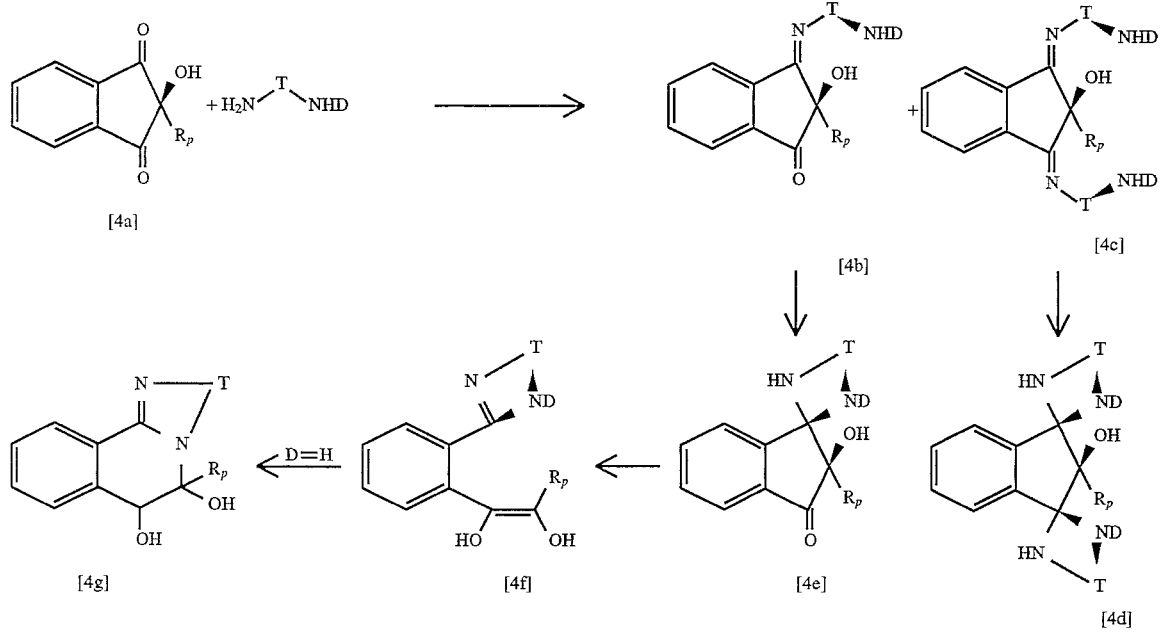

[4a] [4b] [4c] [4d] [4e] [4f] [4g]

Useful polyamines featuring amido groups derived from alpha- and beta-aminoacids are illustrated in the formulae below:

$NH_2CH\Psi C(=O)NH(\omega NH)_xH$ and $H(NH\omega)_xNHCH_2CH_2C(=O)NH(\omega NH)_xH$ wherein $\Psi$ is selected from the group consisting of $R_p$ and substituted alkyl groups, wherein the substituents are derived from natural amino acids such as, cysteine, glutamic acid and lysine.

Polyamine Products

In a highly preferred embodiment of the present invention, the amination of adducts $R_p(KM)_n$, $R_p(IT)_n$, and $R_p(AX)_n$ (wherein n averages from about 1.2 to about 1.8, and $R_p$ is a hydrocarbyl radical of a polymer selected from the group consisting of poly-n-butene, poly-alpha-olefin, ethylene propylene copolymer, and ethylene butene-1 copolymer, said polymers having Mn values ranging from about 500 to about 20K with one double bond per chain) with the above described polyamines using various reactant ratios and reaction conditions produces a new family of dispersants that effectively control sludge and varnish, and feature antioxidant, high base number, and VM credits.

In one aspect of this embodiment, adducts bearing keto groups, typified by IT-polymer adducts, condense with polyamines ($NH_2$-T-NHD) to give as a function of stoichiometry, a wide assortment of products represented in part by structures 4b–4g shown below wherein T is selected from the group consisting of ethylene, propylene, trimethylene, o-phenylene, and $(CH_2CH_2NH)_xCH_2CH_2$; and D is selected from the group consisting of H, and $(CH_2CH_2NH)_xH$ wherein x is an integer ranging from 1 to about 10, and $R_p$ is defined above. The kind and amount of the products illustrated below, can vary substantially depending on the structure of the adducts, the polyamines, stoichiometry, and reaction conditions.

In addition, when the mole ratio of $R_p$IT:polyamine is about 2 or more, and $D=(CH_2CH_2NH)_xH$, the primary amine groups available in structures 4b–4f shown below condense with additional $R_p$IT to afford a plurality of other higher molecular weight products. With a judicious choice of reagents, stoichiometry, and reaction parameters, one skilled in the art, can design an additive composition which meets a specific fuel and/or lube end use. Aminating polyfunctional adducts such as $R_p(IT)_n$ wherein n averages from about 1.2 to 1.8, with the above-described polyamines provides high nitrogen products with significantly enhanced antioxidant, dispersant and viscosity properties, and said products represent an especially preferred embodiment of the present invention.

In another aspect of the preferred embodiment, adducts bearing ester, and amide groups as typified by keto malonate and alloxan polymer adducts, $R_jKM$, and $R_jAX$, respectively, condense with polyamines to give mixtures of macrocyclic amidoamines ($R_jMC$) and acyclic amidoamines ($R_jAC$). The aminolysis of $R_jAX$ (5a) with NH2-T-NHD (pa) involving the proposed ureido intermediate as depicted by 5b is shown below:

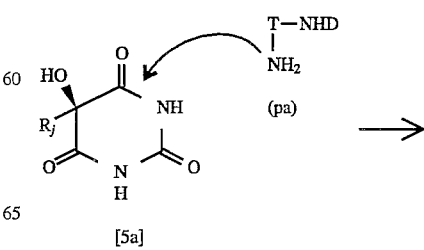

[5a] (pa)

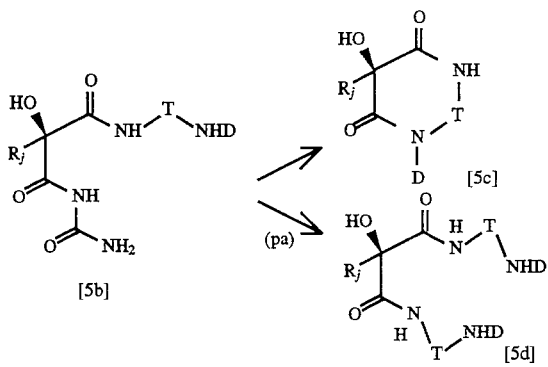

The kind and amount of amidoamines, 5c and 5d, will depend upon the nature of the adduct, and the polyamine, as well as stoichiometry and reaction conditions. Both the macrocyclic amidoamines (5c) and acyclic amidoamines (5d) are useful additives, per se, as well as precursors to transition metal complexes, such as copper complexes which are known to be effective antioxidants.

Aminating polyfunctional adducts such as $R_p(AX)_n$, and $R_p(KM)_n$, wherein n averages from about 1.2 to about 1.8, as taught above, provide highly preferred products comprising macrocyclic amidoamines ($R_pMC$) and acyclic amidoamines ($R_pAC$), with enhanced dispersant and viscosity properties.

"Cascade" additives can be designed by treating the adducts 1c, 2c and 3c with the above described cascade-like polyamines (e.g., CP-8), and polyamidoamine derivatives. The presence of high concentrations of amine functionality arranged in a compact, spheroidal configuration may enhance additive performance.

Amino alcohols

Amino alcohols are also effective nucleophiles in converting the ene and radical adducts to products with useful fuel and lube properties. Useful amino alcohols and substituted amino alcohols feature one or more amino groups selected from $NH_2$ and/or NH radicals, and one or more OH groups capable of reacting with one or more adducts of the present invention. Amino alcohol reagents used in designing effective dispersants feature amino radicals such as $NH_2$ and/or NH, and one or more OH radicals attached to alkanes or branched alkanes containing from about 2 to about a hundred carbons. Amino alcohols capable of reacting with the adducts of the present invention are depicted by the formula:

$$\Phi_1\Phi_2N—\beta—OH$$

wherein $\Phi_1$ and $\Phi_2$ are independently selected from the group consisting of H, alkyl ranging from 1 to about 30 carbon atoms, H—(NHω)$_x$—, H—(Oω)$_x$—; β is selected from the group consisting of ethylene, propylene, butylene, trimethylene, —$CH_2C(CH_2OH)_2$—$CH_2$—, 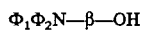, and —ω(N[τ]ω)$_x$— wherein τ=H, and —ω(NHω)$_x$—$NH_2$; ω and x are defined above.

The amino and aminoalkyl groups present in amino alcohol reactants can be attached to alkanes, homocycles, and heterocycles; moreover, each class of amino alcohol may contain one or more substituents.

Examples of aliphatic amino alcohols, and substituted derivatives include: ethanolamine, 3-amino-1-propanol, 2-amino-1-pro-panol, 4-amino-1-butanol, 2-amino-1-butanol, 2-amino-2-methyl-1-propanol, 5-amino-1-pentanol, 2-amino-1-pentanol, 2-amino-3-meth-yl-1-butanol, 6-amino-1-hexanol, 2-amino-1-hexanol, isoleucinol, leucinol, serinol, 1-amino-1-cyclopentanemethanol, 2-aminocyclo-hexanol, 4-amino-cyclo-hexanol, 1-aminomethyl-cyclo-hexanol, 3-aminomethyl-3,5,5-trimethylcyclohexanol, 2-[2-amino-ethoxy]-ethanol, 2-methyl-aminoethanol, 2-ethylaminoethanol, 2-propyl-aminoethanol, diethanolamine, N,N-diethylethanol-amine, 3-dimethylamino-1-propanol, 3-amino-1,2-propanediol, N-ethyl-di-ethanolamine, triethanolamine, 3-dipropylamino-1,2-propanediol, 2-amino-2-ethyl-1,3-propanediol, bis-homotris, tris-(hydroxy-methyl) amino-methane (THAM), 2,2-bis-(hydroxymethyl)-2,2',2"-nitrilo-triethanol, 1,3-diamino-2-hydroxypropane, 2-(2-aminoethylamino) ethanol, 1,3-bis-(dimethylamino)-2-propanol, N,N'-bis-(2-hydroxyethyl)ethylenediamine, 1,3-bis-tris (hydroxymethyl)methylaminopropane, pentrol, 1-amino-1-deoxy-D-sorbitol, N-methyl-D-glucamine, disorbityl-amine, D-galactosamine, D-glucosamine, 1-(2-hydroxyethyl) pyrrolidine, 3-pyrrolidino-1,2-propanediol, 3-pyrrolidino-1,2-pyrrolidinemethanol, 1-methyl-2-pyrrolidine-ethanol, 1-piperidineethanol, 3-piperidino-1,2-propanediol, 2-piperidinemethanol, 2-piperidineethanol, 3-hydroxy-piperidine, 1-ethyl-4-hydroxypiperidine, 3-morpholino-1,2-propane-diol, tricine, bicine, serine, isoserine, homo-serine, threonine, 3-hydroxy-norvaline, muramic acid, 5-hydroxy-lysine, and 4-hydroxy-proline.

Examples of amino alcohols and alkane amino alcohols con-taining homocyclic and heterocyclic groups include: 2-amino-phenol, 2-amminobenzylamine, 2-aminophenethanol, 4-aminophen-ethanol, 2,3-diaminophenol, 4-aminoresorcinol, 2,4-diaminophenol, 1-amino-2-naphthol, 2-amino-1-phenylethanol, 2-phenylglycinol, norephedrine, pseudoephedrine, ephedrine, 2-amino-1-phenyl-1,3-propanediol, S-benzyl-L-cysteinol, tyramine, octopamine, syn-ephrine, thiomicamine, 3,4-dihydroxybenzylamine, epinephrine, dopamine, propranolol, tyrosine, dopa, 3-phenylserine, dops, and phenyl-4-amino-salicylate; useful heterocyclic amino alcohols include: 4-hydroxymethylimidazole, 4-hydroxy-indole, 1-indole-methanol, tryptophol, homotryptophol, serotonin, 5-hydroxy-tryptophan, 2,3-dihydroxypyridine, 2,6-pyridinedimethanol, and pyridoxine.

Amino Alcohol Products

Amino alcohols such as THAM are also effective nucleophiles for converting the ene and radical adducts from alloxan and ketomalonate ester to polyol products. Accordingly, the aminolysis of ketomalonate-hydrocarbon adducts with THAM in the presence of bases such as potassium carbonate, affords mixtures containing amido polyols as depicted below.

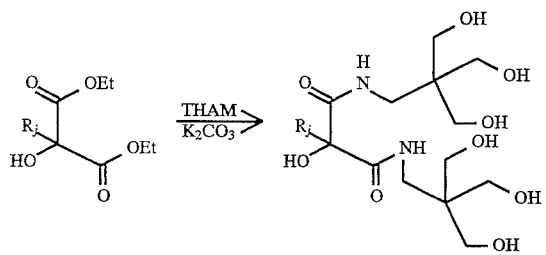

If heated at about 160° C. for about 8 hours, the amido polyol products cyclodehydrate to form oxazolines.

It is noted that mixtures of amido and ester polyol-containing products are formed via the aminolysis of alloxan-hydrocarbon adducts with THAM.

Examples of polyols bearing alkane, and cycloalkane groups include: ethylene glycol, 1,3-propane, 1,2-propane, 2,3-butane, 1,5-pentane, 2,4-pentane, 3,3-dimethyl-1,2-butane, 1,6-hexane, 2,5-hexane, 2-ethyl-1,3-hexane, 1,8-octane, 1,2-octane, 1,10-decane, 1,2-decane, 1,14-tetradecane, 1,2-tetradecane and 1,16-hexadecane-diol; glycerol, 1,1,1-tris-(hydroxymethyl)ethane, 1,2,3-heptanetriol, pentaerythritol (PE), threitol, erythritol, xylitol, ribose, fructose, glucose, 1,2-cyclopentane, 1,2-cyclohexanediol; 1,3,5-cyclohexanetriol, 1,2-cyclohexanedimethanol, 1,2-cyclooctanediol, pinanediol, inositol and the following cascade polyols (CP-12 and CP-36) as taught in U.S. Pat. No. 4,587,329.

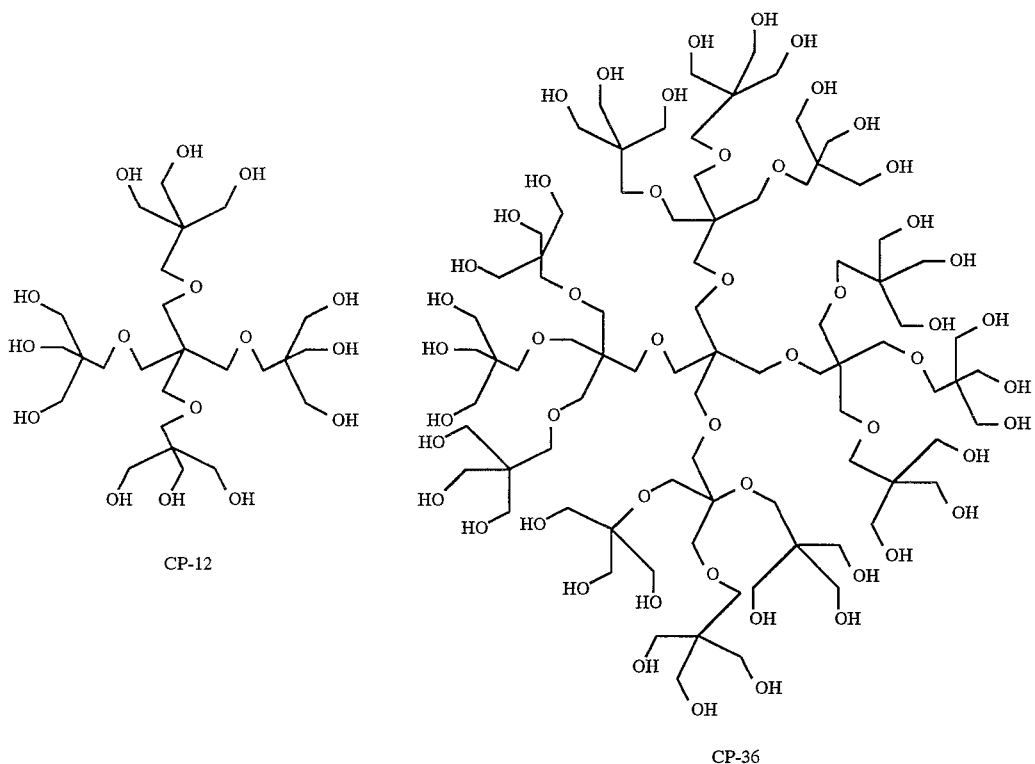

CP-12

CP-36

In another aspect of the instant invention, condensation of amino alcohols such as THAM with IT-hydrocarbon adducts produces mixtures containing oxazolidine derivatives useful as fuel and lube additives.

Polyols

Useful polyols and substituted polyols for converting ene and radical adducts to products feature two or more OH groups capable of reacting with one or more adducts. Polyhydric alcohols capable of reacting with one or more of the adducts of the present invention are depicted by the formula:

HO—λ—OH wherein λ is selected from ethylene, propylene, butylene, and trimethylene; —CH$_2$C(CH$_2$OH)$_2$CH$_2$—, and —CH$_2$(CHOH)$_x$CH$_2$.

Useful substituted polyols include: 3-methoxy-1,2-propanediol, diethylene glycol, dipropylene glycol, batyl alcohol, triethylene glycol, tripropylene glycol, tetraethylene glycol, pentaethylene glycol, hexaethylene glycol, dipentaerythritol, tripenterythritol, 1,2-dithiane-4,5-diol, 1,5-dithiacyclooctan-3-ol, 1,5,9,13,-tetrathiacyclohexadecane-3,11-diol, and 1,5,9,13,17,21-hexathia-cyclotetracosane-3,11,19-triol; gluconic acid, tartaric acid, mucic acid, quinic acid, shikimic acid, and ascorbic acid.

Other useful polyols are those wherein the hydroxy or hydroxyalkyl groups are attached to a homocycle or a heterocycle. Examples of polyols containing homocyclic and heterocyclic groups, and cyclic groups with substituents include: catechol, 4-t-butylcatechol, pyrogallol, resorcinol, olivetol, 2,3-dihydroxy-naphthalene, 4-t-butylcalix-(6)-arene, 1,3-benzenedimethanol, 1-phenyl-1,2-ethanediol, 2-benzyloxy-1,3-propanediol, 3-hydroxyphenethanol, hydro-quinone bis-(2-hydroxyethyl) ether, 4,4'-thiodiphenol, 2,4-dihydroxy-propiophenone, phloretin, quinalizarin, purpurin, fisetin, myricetin, 3,5-dihydroxybenzoic acid, gallic acid, and resorcinol sulfoxide; polyol containing heterocycles include: 2,5-furandimethanol, and 2,5-thiophenedimethanol.

Polyol Products

Polyol dispersant products are prepared by treating adducts, $R_jAX$, and $R_jKM$, with pentaerythritol (PE) and cascade polyols. Thus, $R_jAX$ undergoes alcoholysis with PE in the presence of diazabicycloundecene (DBN) to produce a mixture of polyol ester products comprising the bis-PE ester as shown below.

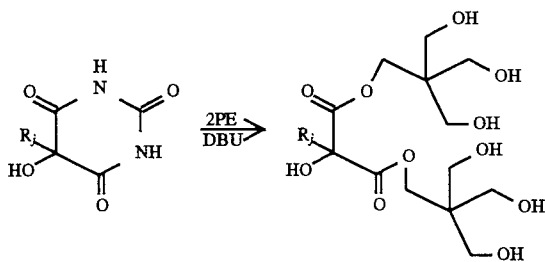

Moreover, combinations of polyol and polyamine reagents can be employed advantageously to produce mixed dispersants that are useful in certain fuel and lube applications. For example, the alcoholysis of polyamine-treated AX-hydrocarbon and KM-hydrocarbon adducts with PE and cascade polyols affords highly useful mixed dispersants.

Also, the acid-catalyzed addition of polyols such as glycerol, PE, and cascade polyols, to keto-bearing adducts such as IT- polymer adducts, affords useful fuel and lube additives.

Alternate routes to polyol products

Other synthetic protocols to polyol additives includes borohydride reduction or catalytic hydrogenation of adducts of the present invention. For example, the carbonyl groups of the ene and radical adducts of indantrione may be reduced in the presence of metal hydrogenation catalysts, such as palladium on carbon, in the presence of a suitable solvent, such as methanol, dioxane or toluene. Alternatively, the carbonyl can be reduced with chemical reducing agents, such as borohydrides, in an appropriate solvent like dioxane, tetrahydrofuran, and ethanol. In the case of chemical reducing agents, such as sodium borohydride, only the carbonyl groups are reduced, whereas, when the reducing reagent used is a metal hydrogenation catalyst, both the carbonyl groups and the olefinic groups are reduced.

Also, in accordance with the present invention, hydroxy substituted nitriles or phosphonates are formed by reacting IT-hydrocarbon adducts with acetone cyanohydrin (a source of HCN) or dialkyl phosphite nucleophiles in the presence of a base catalyst such as DBU.

Reactions of Metal salts and complexes

The adducts and products of the present invention can be treated with metal salts and metal complexes, to produce useful multi-functional additives for fuels and lubes. Thus, metal-containing derivatives of (i) adducts 1c, 2c, and 3c and (ii) certain products of such adducts with amines, polyamines, amino alcohols, alcohols, and polyhydric alcohols, can be produced via addition of metal salts and metal complexes to said adducts and products. Useful alkali, alkaline earth, and transition metal salts are preferably non-halogen, and, more preferably carboxylate, alkoxide, hydroxide, oxide, bicarbonate, and carbonate salts which upon interaction with certain adducts and products of the present invention, form innocuous carboxylic acid, alcohol, water, and $CO_2$ by-products, respectively. Useful metal complexes include alkali, alkaline earth, and transition metal derivatives of chelating agents such as 2,4-pentanedione.

Useful alkali and alkaline earth metals include sodium, lithium, potassium, calcium, magnesium, and barium, respectively. The preferred alkaline earth metals, calcium and magnesium, produce detergent derivatives which can neutralize corrosive acids generated in the combustion of fuels and lubes.

Moreover, the metal derivatives obtained from the metal-treated adducts and products of the present invention, owing to their antioxidant and detergent properties effectively maintain engine cleanliness by (a) suspending, and dissolving sludge, varnish and their precursors as well as (b) preventing or inhibiting the formation of sludge and varnish which tends to induce engine wear, and adversely affect engine performance.

Another preferred group of metal-containing adducts and products which impart useful additive properties feature transition metals such as copper, zinc, cobalt, nickel, chromium, and manganese. Useful carriers include counter ions such as carboxylic acids, and chelating agents such as 1,3-alkanediones, especially 1,3-pentanedione, and related derivatives.

Useful examples of metal carriers include acetic acid, propionic acid, dodecenylsuccinic acid, and polyisobutenylsuccinic acid. Preferred carriers are carboxylic acids derived from adducts 1c, 2c, and 3c, and their polyamine derivatives.

An especially useful group of salts derived from $R_jAX$, can be produced via the replacement of the amido protons with metal salts such as lithium isopropoxide as shown below. The metal salts of AX adducts which are selected from the group consisting of alkaline earth metals, especially calcium and magnesium, are useful detergents. Moreover, lithium and calcium salts of $R_jAX$ are also useful in greases.

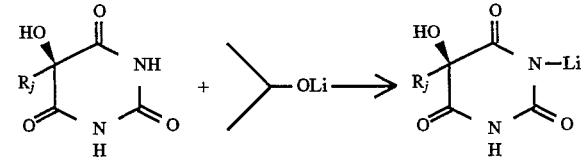

Complexes

Both the acyclic amidoamine ($R_jAC$) and macrocyclic amidoamine ($R_jMC$) products of the present invention readily form neutral metal complexes 6a, and 6b, respectively, as illustrated below, wherein $M_z$=Cu, Ni, and Co.

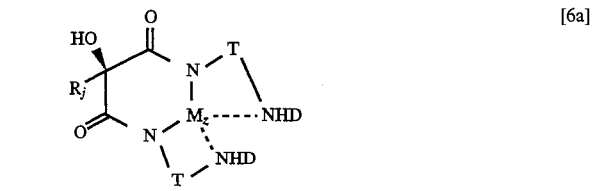

[6a]

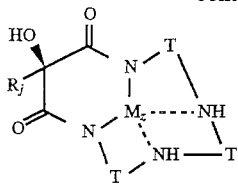

Metal complexes such as 6a, and 6b exhibit outstanding antioxidant properties owing to the ability of said metal complexes, particularly the copper derivatives, to neutralize radicals, presumably via the oxidative dehydrogenation of the polyamine ligands which surround the metal.

Carbon Acid Derivatives

A highly useful conversion of adducts to other additive precursors and products involves the use of carbon acid esters such as esters of cyanoacetic, acetoacetic, and malonic acid. Thus, adducts of IT for example, in the presence of basic catalysts such as beta-alanine, piperidine, ammonium acetate or diazabicyclo-undecene (DBU) undergo Knoevenagel condensation reactions with dimethyl malonate in refluxing toluene or xylene to produce modified adducts as shown below ($R_j$ as previously defined). The latter carbon acid-modified adduct, can react with amines, alcohols, polyamines, polyols, and metal salts to afford highly useful multi-functional additives.

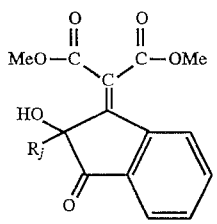

Moreover, the Stobbe condensation of indantrione adducts with esters of succinic acid provides another useful class of multi-functional additives and additive precursors.

POST PRODUCTS

A key embodiment of the present invention involves the post-treatment of the products 1d, 2d, and 3d to further enhance their properties as fuel and lube additives. Thus, the post-treatment, or "capping" of polyamine and polyol derivatives of 1d, 2d, and 3d, with electrophilic reagents can endow these products with enhanced seal compatibility properties; enhanced product stability; antioxidant properties and improved chelating, complexing, and aggregation properties. These attributes translate into improved dispersancy, viscometrics and fluoroelastomer seal compatibility properties for the additives of the present invention.

Useful "capping" reagents for the post-treatment of products 1d, 2d, and 3d include: boron-oxygen compounds; alkane carboxylic acids, anhydrides, and esters; 5-,6-, and 7-membered lactones; alpha, beta-unsaturated acids and esters; 1,3-diketones, and 1,3-keto esters; oxiranes, and thiiranes; aldehydes, and ketones; isocyanates, and isothiocyanates; sulfur and sulfur-oxygen reagents; and phosphorus-oxygen and phosphorus-sulfur reagents.

Examples of the above post-treatment (capping) reagents include: boric acid, meta-boric acid, boric oxide, and trialkyl borate and metaborate esters where alkyl=1 to 18 carbons; acetic anhydride, propionic anhydride, ethyl acetate; butyrolactone, ε-caprolactone; methyl acrylate, methyl methacrylate; 1,3-pentanedione, dimedone, ethyl acetoacetate; propylene oxide, butylene oxide, 1,2-epoxyoctane, 1,2-epoxytetradecane, and propylene sulfide; formaldehyde, butyraldehyde, decanal, cyclohexanone; butyl isocyanate, octadecyl isocyanate, phenyl isocyanate, butyl isothiocyanate, octadecyl isothiocyanate, phenyl isothiocyanate; disulfane, tetrasulfane, and polysulfane mixtures, diethoxy sulfane, and thiosulfuric acid; phosphorus pentoxide, phosphorous pentasulfide, phosphoric, and thiophosphoric acid; dialkyl and trialkyl phosphites, phosphates, and thiophosphates where alkyl denotes from about 1 to about 18 carbons. Besides passivating basic nitrogen, thiosulfuric and thiophosphoric acid can impart antioxidant properties to additives.

Boration

Post-products containing boron can be formed via the addition of boric acid, ester or metaborate ester to the aminated adducts of the present invention.

A preferred method of the present invention involves the direct treatment of adducts with a soluble form of boron which is prepared by combining a mixture of a polyamine and boric acid, and heating the mixture at about 130° C. until a clear liquid polyamine metaborate (PMB) salt is obtained as shown below wherein T is selected from the group consisting of ethylene, propylene, trimethylene, and $(CH_2CH_2NH)_xCH_2CH_2$; and x is a numerical value ranging from about 1 to about 10.

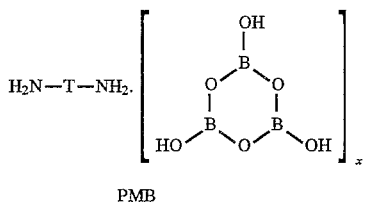

PMB

Addition of the PMB to an adduct of the present invention at about 120° C. to about 180° C., appears to "boraminate" the adduct, and produces a borated polyamine dispersant in one step. PMB derivatives are easily formed by reacting a mole of TETA, TEPA, PEHA or virtually any high molecular weight polyamine with one or more moles of boric acid at about 130° C. until a clear, liquid PMB salt is obtained. Typically, PMB salts will contain from one to about three moles of boric acid for each available amine group in the polyamine-treated adducts. Because heating mixtures of PAM and boric acid at temperatures above 150° C. for extended periods may form insoluble products, a preferred protocol for producing the PMB reagent is to simply stir a mixture of PAM and boric acid at about 130° C. until a clear amber solution is obtained. Note that the proposed PMB structure illustrated above is approximate since metaboric acids may also exist, in part, as linear structures.

Acylation

Electrophiles such as ethyl acetate, acetic anhydride, ethyl ortho-acetate, ethyl acetoacetate, and 2,4-pentandione react with polyamine-modified additives, thereby passivating their basic properties, and as a consequence, enhancing their seal compatibility properties.

Salt Formation

Similarly, the addition of thioacids such as sulfanes (di-, tri- and tetra-sulfane), thiosulfuric acid, and thiophosphoric acid to polyamine-treated adducts produces salt derivatives with enhanced seal compatibility properties as well as antioxidant properties.

Reduction

In another aspect of post-product synthesis, polyamine-treated adducts derived from IT such as 7a, are reduced with chemical reagents such as diborane or $NaBH_4$, to produce novel saturated derivatives as typified by the amino alcohol, 7b, shown below. Similarly, macrocyclic amidoamines such as 7c are readily reduced to macrocyclic polyamines, 7d, with borane. The reduced polyamine products are useful fuel and lube additives as well as valuable precursors to transition metal complexes.

represented by the formulae 1d and 3d, a is zero, J and K are equal to C=O, and L, Q, E and F are independently selected from the group consisting of OH and $NH(CH_2CH_2NH)_xH$, and L+Q are selected dependently from the group consisting of $NH(CH_2CH_2NH)_xCH_2CH_2NH$ and $NHCH_2CH_2NHCH_2CH_2CH_2NHCH_2CH_2NH$. In the case of products represented by the formula 2d, J and K are independently selected from the group consisting of C=O, C=$NR_n$ and C=$NR_o$.

In one embodiment, a composition is provided comprising a major amount of an oleaginous substance and a minor

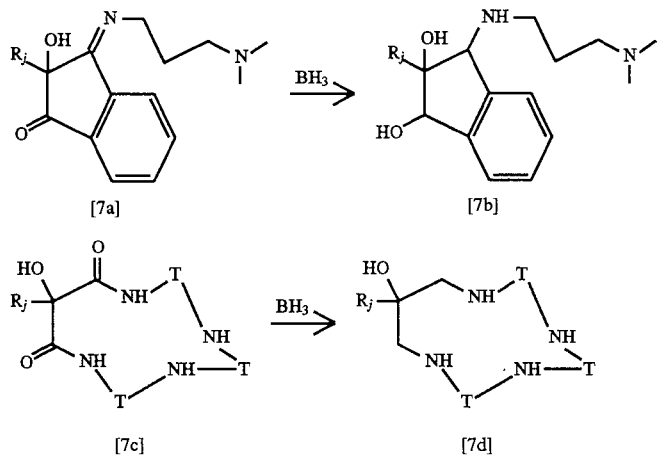

Additive Uses

The adducts, products, and post-products of the present invention constitute a new family of additives with broad applications. In a preferred embodiment of the present invention, the adducts, products, and post-products have been found to be especially useful as fuel and lube additives. Thus, they can be incorporated directly into a lubricant oil or fuel by dissolving or dispersing the additive at the desired concentration at room temperature or an elevated temperature which facilitates dissolution without affecting the integrity of the additive. If preferred, the additive can be blended with various natural and synthetic basestocks, and petroleum distillates to produce a concentrate which is blended with a lubricating oil or fuel to obtain the desired formulation. The additive concentrates will usually contain, on an active ingredient (a.i.) basis from about 5 to 50 wt % and preferably from about 10 to 40 wt % additive, and typically from about 30 to 90 wt %, preferably from about 40 to 60 wt % base oil, based on the concentrate weight.

Fuels

When the additive compositions of this invention are used in fuels, such as middle distillates boiling from about 65° C. to about 425° C., including kerosene, diesel fuels, home heating fuel oil, and jet fuels, a concentration of the additive in the fuel in the range of typically from about 0.001 wt. % to about 0.5 wt. %, preferably about 0.005 wt. % to about 0.2 wt. % based on the total weight of the composition, will usually be employed.

The adducts, products and post-products of this invention are useful additives for fuels in the gasoline boiling range, for preventing or reducing deposits in the combustion chamber, and adjacent surfaces such as valves, ports, and spark plugs, and thereby reducing octane requirements. Preferred products of formulae 1d, 2d and 3d, include those compounds where the $M_n$ of $R_j$ varies from about 500 to about 5K, and G is hydroxyl. In the case of products amount of an adduct of a hydrocarbon having a Mn ranging from about 500 to about 10 million with at least one VP monomer, and generally from about 1 to about 20 monomers. Typical amounts of the adduct will be from about 0.01 wt % to about 10 wt % based on the weight of the composition.

Other oleaginous compositions include minor amounts of products of ene and radical adducts, said adducts containing one or more VP monomers and a major amount of an oleaginous substance. As above, typically from about 0.01 wt % to about 10 wt % of products or mixture of products will be present in the composition.

Compositions including major amounts of oleaginous substances and minor amounts of post-products are also within the scope of the present invention. Typical amounts of post-products are from 0.01 wt % to about 10 wt % based on the weight of the composition.

Hereinafter specific mention will be made to fuel and lube compositons such specific illustrations however, should not be construed as limiting the scope of the disclosed invention.

Fuel Compositions

Suitable liquid hydrocarbon fuels of the gasoline boiling range are mixtures of hydrocarbons with a boiling range from 25° C. to about 230° C. The hydrocarbon composition and octane level of the base fuel are not critical. Any conventional motor fuel base can be used in the practice of the present invention. Hydrocarbons in the gasoline can be replaced by substantial amounts of conventional alcohols, or ethers known for use in fuels.

Preferably, the gasolines are lead-free, but may contain minor amounts of blending agents such as methanol, ethanol, and methyl t-butyl ether at from 0.1 to 10 volume % of the base fuel.

The fuels can also contain antioxidants such as 2-octadecenyl-2-hydroxy-indan-1,3-dione, 2,6-di-t- butylphenol or o-phenylene-diamines, dyes, metal dactivators, and dehazers. Corrosion inhibitors such as pentaerythritol esters of tartronic acid derivatives having from 20 to 500 carbons, for example, pentaerythritol mono-and diesters of polyisobutenyl tartronic acid, wherein the polyisobutene group has an $M_n$ of about 950 in an amount from about 10 to about 500 ppm by weight. An especially useful class of antioxidant dispersant for fuels is typified by IT adducts of octadecene, and polymers such as polybutene (wherein $M_n$ ranges from about 950 to about 2.5K), and ethylene butene copolymers (wherein $M_n$ ranges from about 1K to about 2K) aminated with a polyamine such as EDA, PDA, TETA, TEPA and 1.2-phenylene diamine. Said additives or a concentrate of said additives, can also be used in combination with poly(oxyalkylene) glycols or polyolefin amines.

The additives of the present invention can be effectively introduced into the combustion zone of an engine in a variety of ways to prevent buildup, reduction, or modification of harmful engine deposits. The additive can be injected into the intake manifold or added directly to the fuel, or blended with other additives.

Effective amounts of additive of the present invention will depend on the particular compound used, the engine and the fuel. For example, the polyamine-treated adducts, 2d and 3d or mixtures of 2d and 3d, are used in an amount of from about 20 to 800 ppm based on the total weight of fuel, and preferably from about 40 to about 500 ppm by weight.

Another aspect of the invention relates to diesel, heating and jet fuel compositions and to reduction of deposits and emissions. A need exists for emission-reducing additives for diesel and jet fuel that are metal free and combustible without contributing to particulate emissions. Polyamine-treated adducts of 1c, 2c and 3c of the present invention in combination with cetane enhancers, when used in diesel, heating, or jet fuel can effectively control particulate emissions. The additives may be used alone or in combination with other fuel additives at concentrations in the range of from about 0.001 to about 2, and preferably from 0.005 to about 0.3 wt % based on the weight of the fuel. Other additives which may be used in combination include, for example, diesel detergents, antifoam additives, anti-rust additives, and demulsifiers, and may be present in the fuel at a concentration of about 0.001 to about 1 wt %.

When the additives of this invention are added to the refinery process streams or other hydrocarbon fluid process streams, they function as antifoulants.

Lubes

The adducts, products and post-products of this invention, and particularly the polymer analogs, find their primary utility, however, in lubricating oil compositions, which employ a base oil in which the additives are dissolved or dispersed. Such base oils may be natural or synthetic. Indeed, base oils suitable for use in preparing the lubricating compositions of the present invention include those conventionally employed as crankcase lubricating oils for spark-ignited and compression-ignited internal combustion engines, such as automobile and truck engines, marine and railroad diesel engines, and the like.

Thus, the compositions of the present invention comprise a lubricating oil and an effective amount of an additive selected from the group consisting of ene and radical adducts, products, post-products, and mixtures thereof. These compositions may include conventional additives as well.

Accordingly, while any effective amount of these additives can be incorporated into a fully formulated lubricating oil composition, it is contemplated that the composition contain from about 0.01 to about 10 wt %, e.g., and preferably from about 0.1 to about 6 wt. %, based on the weight of said composition.

The additives of the present invention can be incorporated into the lubricating oil in any convenient way. Thus, they can be added directly to the oil by dispersing, or dissolving the same in the oil at the desired level of concentration, typically with the aid of a suitable solvent such as toluene, cyclohexane, or tetrahydrofuran. Such blending can occur at room temperature or elevated temperatures. Alternatively, these additives may be blended with a suitable oil-soluble solvent or base oil to form a concentrate, which may then be blended with a lubricating oil base stock to obtain the final formulation. Concentrates will typically contain from about 2 to about 80 wt. %, and preferably from about 5 to about 40 wt. % based on the weight of the additive.

Advantageous results are also achieved by employing the additives of the present invention in base oils conventionally employed in and/or adapted for use as power transmitting fluids such as automatic transmission fluids, tractor fluids, universal tractor fluids and hydraulic fluids, heavy duty hydraulic fluids, power steering fluids and the like. Gear lubricants, industrial oils, pump oils and other lubricating oil compositions can also benefit from the incorporation therein of the additives of the present invention.

Substantial benefits can also be realized by employing low molecular weight ($M_n$ ranging from about 400 to about 2K) products and post-products of polyamine-treated adducts especially $R_pAX$, $R_pIT$, and $R_pKM$ adducts, in two-cycle engine oils. Suitable polyamines include: EDA, PDA, DETA, TETA, TEPA, Polyamine-H, and o-phenylene diamine.

Thus, the additives of the present invention may be suitably incorporated into synthetic base oils such as alkyl esters of mono- and dicarboxylic acids, polyglycols and alcohols; poly-alpha-olefins, polybutenes, alkylbenzenes, organic esters of phosphoric acids, polysilicone oils, and synthetic base oils preferably stabilized by modification with IT. It should be noted that the functionalization of synthetic basestocks via the free-radical addition of 0.1 to 5 wt. % of IT imparts enhanced antioxidant properties to these lubricants.

Natural base oils include mineral lubricating oils which may vary widely as to their crude source, whether paraffinic, naphthenic, paraffinic-naphthenic, and the like; as well as to their formation, e.g., distillation range, straight run or cracked, hydrofined, solvent extracted and the like, and preferably, natural basestocks stabilized by modification with IT.

More specifically, the natural lubricating oil base stocks which can be used in the compositions of this invention may be straight mineral lubricating oil or distillates derived from paraffinic, naphthenic, asphaltic, or mixed base crudes, or, if desired, various blends oils may be employed as well as residuals, particularly those from which asphaltic constituents have been removed. The oils may be refined by conventional methods or they may be extracted oils.

Thus, the additives of the present invention can be employed in a lubricating oil composition which comprises a lubricating oil, or a lubricating oil partially functionalized with IT, and the additive, typically in a minor amount, which effectively imparts enhanced dispersancy, and/or V.I. improvement. Moreover, additional conventional additives as well as additives of the present invention can be used to meet the particular requirements of a lubricating oil composition.

The additives of this invention are oil-soluble, dissolvable in oil with the aid of a suitable solvent, or are stably dispersible materials. Oil-soluble, dissolvable or stably dispersible as that terminology is used herein does not necessarily indicate that the materials are soluble, dissolvable, miscible, or capable of being suspended in oil in all proportions. It does mean, however, that the additives, for instance, are soluble or stably dispersible in oil to an extent sufficient to exert their intended effect in the environment in which the oil is employed. Moreover, the additional incorporation of other additives may also permit incorporation of higher levels of a particular polymer adduct hereof, if desired. In some instances, partial IT-functionalization can enhance the solubilizing properties of basestocks.

The lubricating oil base stock for the additives of the present invention typically is adapted to perform a selected function by the incorporation of additives therein to form lubricating oil compositions (i.e., formulations).

Representative additives typically present in such formulations which can be selected from the adducts, products and post-products of the present invention, include viscosity modifiers, corrosion inhibitors, oxidation inhibitors, friction modifiers, other dispersants, anti-foaming agents, anti-wear agents, pour point depressants, detergents, rust inhibitors and the like.

A viscosity modifier (VM) imparts high and low temperature operability to the lubricating oil and permit it to remain shear stable at elevated temperatures, and also exhibits acceptable viscosity or fluidity at low temperatures. These viscosity modifiers are generally high molecular weight hydrocarbon polymers including polyesters. The viscosity modifiers may also be derivatized to include other properties or functions, such as the addition of dispersancy properties. The dispersant VM products of the present invention feature outstanding performance features.

These oil soluble viscosity modifying polymers will generally have $M_n$ values of about 20K to about a million, preferably from about 50K to about 500K.

Representative examples of suitable viscosity modifiers are any of the types known to the art including polyisobutylene, copolymers of ethylene and propylene (EP), polymethacrylates, methacrylate copolymers, copolymers of an unsaturated dicarboxylic acid and vinyl compound, interpolymers of styrene and acrylic esters, and partially hydrogenated copolymers of styrene/isoprene, styrene/butadiene, and isoprene/butadiene, as well as the partially hydrogenated homopolymers of butadiene and isoprene.

Especially useful dispersant VM products are selected from the group consisting of aminated adducts of ethylene propylene copolymers (with $M_n$ values ranging from about 20K to about 100K), and ethylene propylene 5-ethylidene-2-norbornene (ENB) terpolymers (with $M_n$ values ranging from about 50K to about 100K and containing about 5 to about 10 wt % ENB) and VP monomers comprising IT, AX, 1.3-dimethylalloxan, and KM. For example, the dispersant VM products, 8a, and 8b, shown below (Rq defined above) can be conveniently prepared in solution, or in the melt using a Braebender mixer or an extruder, wherein the polymer is first modified, for example, with a VP monomer in the melt, and successively aminated with 3-dimethylaminopropylamine (DMAP) directly in the melt, or with DMAP in solution at about 130° C. The number of pendant functional groups, n, can vary from about 2 to about a 200 with polymers having $M_n$ values of about 20K to about 500K.

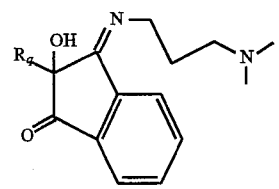

[8a]

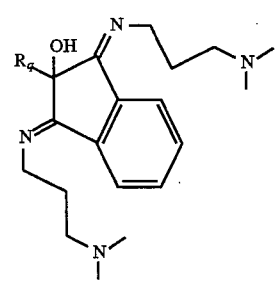

[8b]

In another aspect of the instant invention, highly useful dispersant-viscosity improvers are based on star-branched (partially hydrogenated) polyisoprenes functionalized with IT, AX, or 1.3-dimethylalloxan via ene processes which, owing to mild reaction conditions, (refluxing toluene, for example) afford ene adducts with molecular weight distributions comparable to the starting star-branched polymers having for example, $M_n$ values of about 280K. Amination of the ene adducts with 3-dimethylaminopropylamine affords highly effective viscosity improvers with antioxidant and dispersant properties. These products are useful as VI improvers for conventional basestocks and synthetic, e.g., poly-alpha-olefin or ester basestocks, because of their low contribution to cold cranking viscosities.

Corrosion inhibitors, also known as anti-corrosion agents, reduce the degradation of the metallic parts contacted by the lubricating oil composition. Illustrative of corrosion inhibitors are phosphosulfurized hydrocarbons and the products obtained by reaction of a phosphosulfurized hydrocarbon with an alkaline earth metal oxide or hydroxide, preferably in the presence of an alkylated phenol.

Oxidation inhibitors, or antioxidants, reduce the tendency of mineral oils to deteriorate as evidenced by the products of oxidation such as sludge and varnish-like deposits on the metal surfaces, and by viscosity growth. Such oxidation inhibitors include hindered phenols, dioctylphenylamine, phenyl-alpha-naphthylamine, $P_2S_5$-treated hydrocarbons, and sulfur-treated IT adducts.

Preferred antioxidants (shown below) are adducts (9a, 9b ,9c, and 9d) prepared from hydrocarbons and rhodizonic acid, naphthalene tetrone, IT, and dehydroascorbic acid, respectively, wherein $R_j$ is defined above.

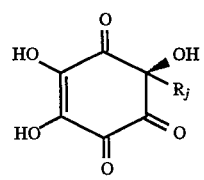

[9a]

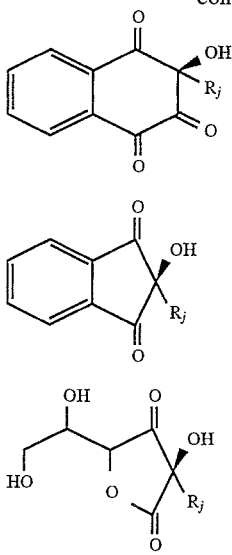

Thermogravimetric analysis (TGA) indicates that octadecene-1, and ethylene butene-1 (EB) copolymers modified with IT are significantly stabilized toward severe thermal oxidative conditions. Accordingly, lubricants containing IT adducts or IT-modified basestocks will feature enhanced thermal oxidative stability.

Other useful antioxidants include oil-soluble copper salts and complexes. A wide assortment of carriers can be used to dissolve the copper derivatives in lube oils, and include dialkyl and diaryl dithiophosphoric acids and dithiocarbamic acids, alkanoic acids wherein alkyl=1–18 carbons, and polymer acids as typified by polyisobutene succinic acids with $M_n$ values from about 950 to about 1.3K, and the adducts of this invention as typified by polyisobutene-, and ethylene butene copolymer-substituted tartronic acids with $M_n$ values from about 1K to about 3K. The copper antioxidants derived from oleic acid, polyisobutenesuccinic acid, and polymer substituted tartronic acids having $M_n$ values ranging from about 500 to about 1.5K will usually be employed in amounts ranging from about 50 to 500 ppm copper in the final lubricating oil or fuel composition.

Neutral macrocyclic copper complexes as typified by 6c (shown below) are readily derived from the polyamine treated adducts of AX, and KM with $R_jH$=octadecene, polybutenes, and ethylene butene copolymers having $M_n$ values of about 500 to about 20K. Said complexes are especially useful antioxidants.

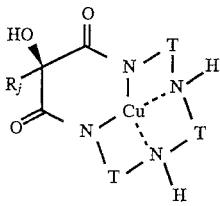

Friction modifiers impart desirable friction properties to lubricating oil compositions used in conventional gasoline and diesel engines and automatic transmissions. Preferred friction modifiers are hemi-esters of octadecenyl succinic acid and 2,2'-thio-bis-ethanol as described in U.S. Pat. No. 4,344,853, and the adducts and products of the present invention as typified by 2-octadecenyl tartronic acid, ester, and amide derivatives.

Dispersants can inhibit or suspend sludge and varnish resulting from thermal oxidation of the base oil thereby preventing the adverse effects of sludge flocculation and deposition on metal parts. While the polybutene succinimide dispersants are useful, the polyamine and polyol treated adducts of IT, AX, and KM with polyisobutenes, poly-n-butenes, poly-alpha-olefins and ethylene-alpha-olefin copolymers having $M_n$ values of about 1K to about 20K are outstanding dispersants. Moreover, the polyamine-treated adducts of IT and the above described polymers are highly useful antioxidant-dispersants.

Pour point depressants, otherwise known as lube oil flow improvers (LOFI), lower the temperature at which a fluid will flow or can be poured. Such additives are well known and useful additives which will optimize the low temperature fluidity of the lube or fluid, are dialkyl fumarate vinyl acetate copolymers (wherein alkyl comprises from 1 to about 18 carbons), and polymethacrylates.

Antifoamants such as silicone oil, and poly dimethylsiloxane, are useful in controlling excessive foam.

Anti-wear agents, as their name implies, reduce metal wear in engines. Typical antiwear agents include zinc salts of dialkyl and diaryl dithiophosphoric acid, and the borate, phosphite, and phosphate esters of 2-octadecenyl-2-hydroxy-indan-1,3-dione.

Detergents and metal rust inhibitors include the metal salts of sulfonic acids, alkylphenols, sulfurized alkylphenols, alkyl salicylates, naphthenates and other oil soluble carboxylic acids. High base (overbased) additives, such as alkaline earth metal sulfonates especially calcium and magnesium salts are frequently used as detergents. The sodium, calcium and magnesium salts of adducts derived from $R_jKM$, $R_jAX$, and $R_jIT$, wherein $R_j$ is selected from the group consisting of hydrocarbyl groups, and substituted hydrocarbyl groups containing about 8 to 40 carbon atoms, are especially useful detergent inhibitors.

Compositions containing the above additives are typically blended into the base oil in amounts which are effective to provide their normal attendant function. Representative effective amounts of such additives are illustrated as follows:

| Additive | Wt. % a.i. (Broad) | Wt. % a.i (Preferred) |
|---|---|---|
| Viscosity Modifier | .01–12 | .01–4 |
| Corrosion Inhibitor | .01–5 | .01–1.5 |
| Oxidation Inhibitor | .01–5 | .01–1.5 |
| Dispersant | .1–20 | .1–8 |
| PourPoint Depressant | .01–5 | .01–1.5 |
| Anti-Foaming Agents | .001–3 | .001–0.15 |
| Anti-Wear Agents | .001–5 | .001–1.5 |
| Friction Modifiers | .01–5 | .01–1.5 |
| Detergents/Rust Inhibitors | .01–10 | .01–3 |
| Mineral oil Base | Balance | Balance |

When other additives are employed, it may be desirable, although not necessary, to prepare additive concentrates comprising concentrated solutions or dispersions of the dispersant (in concentrate amounts herein above described), together with one or more of said other additives (said concentrate when constituting an additive mixture being referred to herein as an additive-package) whereby several additives can be added simultaneously to the base oil to form the lubricating oil composition. Dissolution of the additive concentrate into the lubricating oil may be facilitated by solvents and by mixing accompanied with mild heating, but this is not essential. The concentrate or additive-package will typically be formulated to contain the dispersant additive and optional additional additives in proper amounts to provide the desired concentration in the final formulation when the additive-package is combined with a predetermined amount of base lubricant. Thus, the products of the present invention can be added to small amounts of base oil or other compatible solvents along with other desirable additives to form additive-packages containing active ingredients in collective amounts of typically from about 2.5 to about 90%, and preferably from about 5 to about 75%, and most preferably from about 8 to about 50% by weight additives in the appropriate proportions with the remainder being base oil.

The final formulations may employ typically about 10 wt. % of the additive-package with the remainder being base oil.

All of said weight percents expressed herein are based on active ingredient (a.i.) content of the additive, and/or upon the total weight of any additive-package, or formulation which will be the sum of the a.i. weight of each additive plus the weight of total oil or diluent.

This invention will be further understood by reference to the following examples, which include preferred embodiments. All molecular weights are number average molecular weights ($M_n$), and are accurate to within about ±5–10% as denoted by the term, "Mn≈", in the appropriate examples; moreover, an $M_n$ value of a thousand or more will be defined by the symbol K. Thus, Mn≈1000 is simply Mn≈1K.

The following examples exemplify the preparation of the adducts, products and post-products used in accordance with the present invention.

EXAMPLES

ENE ADDUCTS OF ACYCLIC VP MONOMERS

Low MW KM Adducts and Products

Example A1

About 6.12 grams of diethyl ketomalonate (KM) and 8.84 grams of 1-octadecene were combined in a reaction flask, and stirred at 170° C. for 3 hours. The temperature was raised to 200° C. and kept at 200° C. for 30 hours. Upon cooling, the reaction mixture solidified. The solids, recrystallized from dioxane, analyzed for 17.45% oxygen, featured an infrared spectrum with a strong hydroxyl absorption band at 3 microns, and a very strong ester carbonyl band at 5.82 microns, a mass spectrum with a protonated molecular ion at m/z=427, and a CMR spectrum (DMSO-$d_6$) with ester, olefinic and carbinol carbon signals at 169.6, 133.8, 123.1, and 78.7 ppm. The characterization data fully support the adduct, diethyl 2-octadecenyl tartronate shown below:

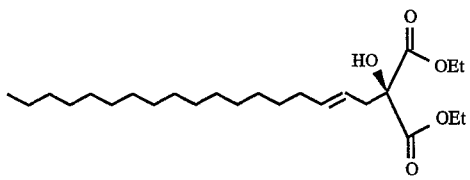

Example A2

About 0.48 g of diethyl 2-octadecenyl tartronate of Example A1, 0.83 g of tris-(hydroxymethyl) aminomethane (THAM), and 0.55 g of $K_2CO_3$ were added to about 75 ml of dimethyl sulfoxide (DMSO) at room temperature. After stirring at 40° C. for about 48 hours, the reaction mixture was filtered, and rotoevaporated at 100° C. for about 4 hours. The residue featured an IR spectrum with a strong amide band at 6 microns and a FAB MS with a protonated molecular ion at m/z=577, suggesting that the reaction mixture contained N,N'-bis-[(tris-hydroxymethyl)methyl] 2-(2-octadecenyl)-tartronamide as illustrated below.

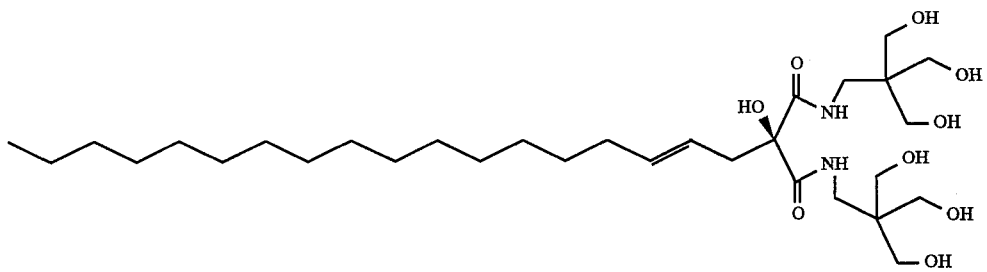

Polymer-KM Adducts and Products

Example A3

One hundred grams of polyisobutylene, $M_n$≈950, and 34.0 grams of KM were combined in a reaction flask and stirred 200° C. for about 40 hours. Rotoevaporation of the reaction mixture at about 100° C. for 8 hours afforded a residue which featured an infrared spectrum with a strong ester carbonyl adsorption band at 5.85 microns, and a saponification number of 92.

Example A4

About 0.01 mole of ethylene propylene copolymer ($M_n$≈1.1K, and 55 wt % ethylene), and 1.7 grams of KM were mixed together in a nitrogen blanketed reactor at 150° C. for about 24 hours. The mixture was diluted with about 100 ml of cyclohexane, and filtered. Rotoevaporation of the filtrate at 100° C. for 8 hours gave a residue featuring an infrared spectrum with a characteristic ester carbonyl band at 5.85 microns.

Example A5

Ninety grams (0.05 mole) of ethylene butene-1 (EB) copolymer ($M_n$≈1.8K, and 55 wt % ethylene) and 20 grams of KM were combined in a nitrogen-blanketed reactor and heated at 180° C. for 42 hours. Volatiles and unreacted ester were distilled off at 120° C. under high vacuum for about 8 hours. The residue featured a strong ester carbonyl absorption band at about 5.8 microns, and analysed for 4.07% oxygen. Chromatographic analysis indicated that the residue (EB-KM) contained 86.7 wt % active ingredient (functionalized polymer).

Example A6

Ten grams of an ethylidene norbornene (ENB) terpolymer ($M_n \approx 55K$ containing about 52% ethylene and about 5% ENB) were dissolved in 100 ml of xylene containing 4 grams of KM. The mixture was stirred at 135° C. for about 70 hours under a blanket of nitrogen. Addition of the cooled reaction mixture to one liter of acetone caused the functionalized polymer to precipitate from solution. The dried polymer analyzed for 3.17% oxygen, and featured an infrared spectrum (film) with an intense ester carbonyl band at 5.82 microns.

Example A7

Ten grams of EB-KM prepared in Example A5, and 5 grams of ethylene diamine (EDA) were combined and stirred at 110° C. for 26 hours. Rotoevaporation of the mixture for 4 hours at 110° C. afforded a residue which featured an infrared spectrum with a broad amido carbonyl absorption band at about 5.9 microns.

Example A8

Ten grams of EB-KM prepared in Example A5, and 1 gram of tetraethylene pentamine (TEPA) were combined and stirred at 120° C. or 32 hours. Rotoevaporation of the mixture for 4 hours at 120° C. afforded a residue which featured an infrared spectrum with a broad amido carbonyl absorption band at about 5.9 microns.

ENE ADDUCTS OF CYCLIC CARBONYL MONOMERS

Low MW Adducts and Products

Rhodizonic Acid

Example B1

A mixture of 2 grams of rhodizonic acid, 5 grams of 2-methylene-norbornane, and 5 grams of dioxane were combined in a nitrogen-blanketed reactor, and stirred at reflux for about 16 hours. The mixture was diluted with 20 ml of diethyl ether, and filtered. Rotoevaporation of the filtrate gave a residue which gave an IR trace with a strong carbonyl band at about 6 microns, and a CI mass spectrum with a protonated molecular ion at m/z=279.

Example B2

Two grams of rhodizonic acid, 2.5 grams of 1-octadecene, and 20 ml of dioxane were combined in a nitrogen-blanketed reactor and stirred at reflux for about 40 hours. Rotoevaporation gave a residue which was dissolved in 50 ml of diethyl ether, and filtered. Evaporation of the filtrate afforded a residue which gave a CI mass spectrum with a protonated molecular ion at m/z=423, thus confirming the presence of the ene adduct in the reaction mixture.

Dehydroascorbic Acid

Example B3

Two grams of dehydroascorbic acid, 6 grams of methylene norbornane, and 8 grams of glacial acetic acid, were combined and stirred at reflux in a nitrogen-blanketed reactor for about 24 hours. Rotoevaporation of the reaction solution gave a residue which featured a CI mass spectrum with protonated ions at m/z=283 and 325, thus confirming the presence of the ene adduct and its mono-acetylated product in the reaction mixture.

This finding indicates that ene adductions effected in the presence of carboxylic acids produce the ene adducts which readily undergo in situ acylation. Similarly, the ene adduction of indantrione to octene-1 in glacial acetic acid affords the acetylated mono- and bis-adducts as revealed by MS analysis which shows two protonated ions at m/z=315 and 517, respectively.

This synthetic protocol is a new process for producing acylated ene adducts. Moreover, this protocol allows ready identification of multi-functionalized adducts formed via the ene reactions of VP monomers and unsaturated hydrocarbons.

Naphthalene Tetrone

Example B4

One gram of naphthalene tetrone dihydrate in 20 ml of dioxane and 10 ml of octene-1 were combined and stirred at 100° C. in a nitrogen-purged reactor for about 12 hours. Rotoevaporation gave a residue which featured a CI mass spectrum with a protonated molecular ion at m/z=301.

Indantrione (IT) Adducts and Products

Example C1

Five grams of indantrione (IT) hydrate and 20 ml of octene-1 were combined and stirred at reflux temperature in a nitrogen-blanketed reactor for 8 hours. Rotoevaporation at room temperature gave a residue which was vacuum distilled, b.p. 170°–174° C. (1 mm). The distillate featured an IR with intense carbonyl bands at 5.72 and 5.85 microns, and analyzed for 75.27% carbon, 7.10% hydrogen, and 17.65% oxygen (Theory for the ene adduct requires 75.00% carbon, 7.35% hydrogen, and 17.65% oxygen). The analytic data fully confirm the structure of the ene adduct as 2-(2-octenyl)-2-hydroxy-1,3-indandione (OCIT)

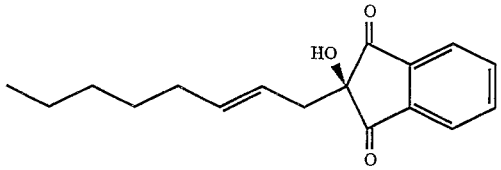

Example C2

Two tenths mole (35.6 grams) of IT hydrate dissolved in 120 ml of 1,4-dioxane, and 64 ml of 1-octadecene were successively added to a nitrogen blanketed reactor fitted with reflux condensor, thermometer, and magnetic stirrer. The reaction mixture was heated at reflux in an oil bath for about 28 hours, and then transferred into an Erlenmeyer flask for refrigeration. The white precipitate that separated from solution was filtered, and recrystallized from acetone. The recrystallized product featured hydrogen and carbon nuclear magnetic resonance spectra fully consistent with the expected ene adduct, an infrared spectrum with strong twin carbonyl absorption bands at 5.72 and 5.87 microns, and an elemental analysis showing 77.67% carbon, 10.06% hydrogen, and 11.39% oxygen (Theory for the ene adduct requires 78.64% carbon, 9.71% hydrogen, and 11.65% oxygen). The combined data fully support the proposed ene adduct, namely, 2-(2-octadecenyl)-2-hydroxy-1,3-indandione (ODIT) shown below:

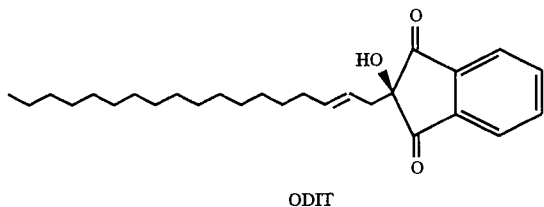

ODIT

Example C3

Fifty millimoles of oleyl alcohol and 8.9 grams of IT hydrate were combined in a nitrogen-blanketed reactor, and stirred at about 110° C. for about 27 hours. Rotoevaporation gave a residue which featured an IR spectrum with a strong carbonyl absorption band at 5.75 microns, and a CI mass spectrum with a base peak (protonated molecular ion) at m/z=429.

Reactions of ene adducts of IT

In the examples which follow, the reactions of ene adducts usually derived from octene-1 or octadecene-1, and IT, namely, OCIT, and ODIT, respectively, were reacted with electrophiles including borate esters and acylating agents such as acetic anhydride; nucleophiles including amine, polyamine, alcohol and polyol reagents; and inorganic bases including KOH to illustrate the preparation of products.

Boration

Example C4

About 0.01 mole of OCIT and 20 grams of triethyl borate were combined in a dry nitrogen-sparged reactor, and stirred at reflux for about 24 hours. Rotoevaporation of the mixture gave a residue which featured an IR spectrum devoid of a hydroxyl absorption band, and a CI mass spectrum with a protonated ion at m/z=373.

Acylation

Example C5

Fifteen grams of OCIT were mixed with 40 grams of acetic anhydride at room temperature. Addition of a small drop of concentrated sulfuric acid raised the temperature of the mixture to 27° C. Heating the stirred reaction mixture to 50° C. for 2 hours produced a clear solution, which was concentrated by rotoevaporation. Vacuum distillation of the residue gave a product, b.p. 176°–178° C. (1 mm Hg), having an infrared spectrum devoid of hydroxyl absorption bands and a CI mass spectrum with a protonated molecular ion at m/z=315.

Amine reactions

Example C6

About 5.4 grams of OCIT in 30 ml of dioxane and 2.9 grams of n-butylamine dissolved in 10 ml of dioxane were combined and stirred in a reactor at room temperature for several days. Rotoevaporation gave a residue which showed an IR with a strong absorption band at about 6 microns, and a FDMS with protonated ions at m/z=328, and 401.

Polyamine Reactions

Example C7

Thirteen grams of OCIT dissolved in 40 ml of dioxane, and 6 grams of ethylene diamine (EDA) in 30 ml of dioxane were combined, and stirred at room temperature. The reaction solution turned dark, but gradually lightened after a half hour. Solids separated from solution after stirring overnight at room temperature. Filtration afforded white crystals (A-EDA) which were recrystallized for tetrahydrofuran (THF), and dried. The white crystals melted at 140°–144° C.; analyzed for 72.55% carbon, 8.28% hydrogen, 8.78% nitrogen, and 9.76% oxygen (Theory for A-EDA requires 72.61% carbon, 8.28% hydrogen, 8.92% nitrogen, and 10.19 % oxygen), featured an IR spectrum with a characteristic C=N absorption band at 6.15 microns; a CI mass spectrum with dominant peaks at m/z=296 and 314; carbon and hydrogen NMR spectra which indicated the product contained 19 carbons and 26 protons, respectively. APT experiments revealed 4 quaternary carbons, seven methylene carbons, seven methine carbons, and one methyl carbon. Combining this information with 2D proton-proton and proton-carbon chemical shift correlation experiments provided clinching evidence for the proposed structure for A-EDA as shown below.

A second product (B-EDA) which formed via the facile dehydration of A-EDA was characterized by MS (protonated peak at m/z=297), and carbon and proton NMR which showed 19 carbons and 24 protons. An APT experiment indicated that there were 5 quaternary carbons, six methine carbons, seven methylene carbons, and one methyl carbon. The APT and 2D NMR data confirmed the proposed structure advanced for B-EDA. Dissolution of 5 grams of A-EDA in glacial acetic acid readily dehydrates it to B-EDA as the acetate salt which analyzes for 69.79% carbon, 7.61% hydrogen, 7.87% nitrogen, and 13.84% oxygen (Theory for B-EDA acetate requires 70.78% carbon, 7.86% hydrogen, 7.87% nitrogen, and 13.48% oxygen).

The hydrogenation of A-EDA in toluene at 60° C. over a Pd spectrum ($BaSO_4$) catalyst for 16 hours, afforded a crystalline product (C-EDA), m.p. 108°–109°. The hydrogenated product (C-EDA) featured an IR with a strong C=N absorption band at 6.15 microns, analyzed for 76.30% carbon, 9.56% hydrogen, and 9.28% nitrogen (Theory for C-EDA requires 76.00% carbon, 9.33% hydrogen, and 9.33% nitrogen); the CI mass spectrum featured a protonated molecular ion at m/z=301; the proton NMR spectrum showed 28 protons, and carbon APT experiments indicated there were 3 quaternary carbons, 6 methine carbons, 9 methylene carbons, and one methyl carbon. Combination 2D proton-proton and proton-carbon chemical shift correlation experiments led to a definitive structural assignment for C-EDA as shown below wherein $R_r$=n-octyl, and $R_s$=2-octenyl.

Reduction of 12.38 grams of A-EDA dissolved in 500 ml of THF with 100 ml of 1.0 molar sodium cyano-borohydride in THF affords, after work-up, a product featuring a CI mass spectrum with a protonated molecular peak at m/z=299, and a carbon NMR completely consistent with the saturated product (D-EDA) as illustrated below.

Finally, rotoevaporation of the supernatent from the above experiment gave a residue which featured a CI mass spectrum with a protonated peak at m/z=357 which is consistent with the bis-imidazolidine product, E-EDA, shown below.

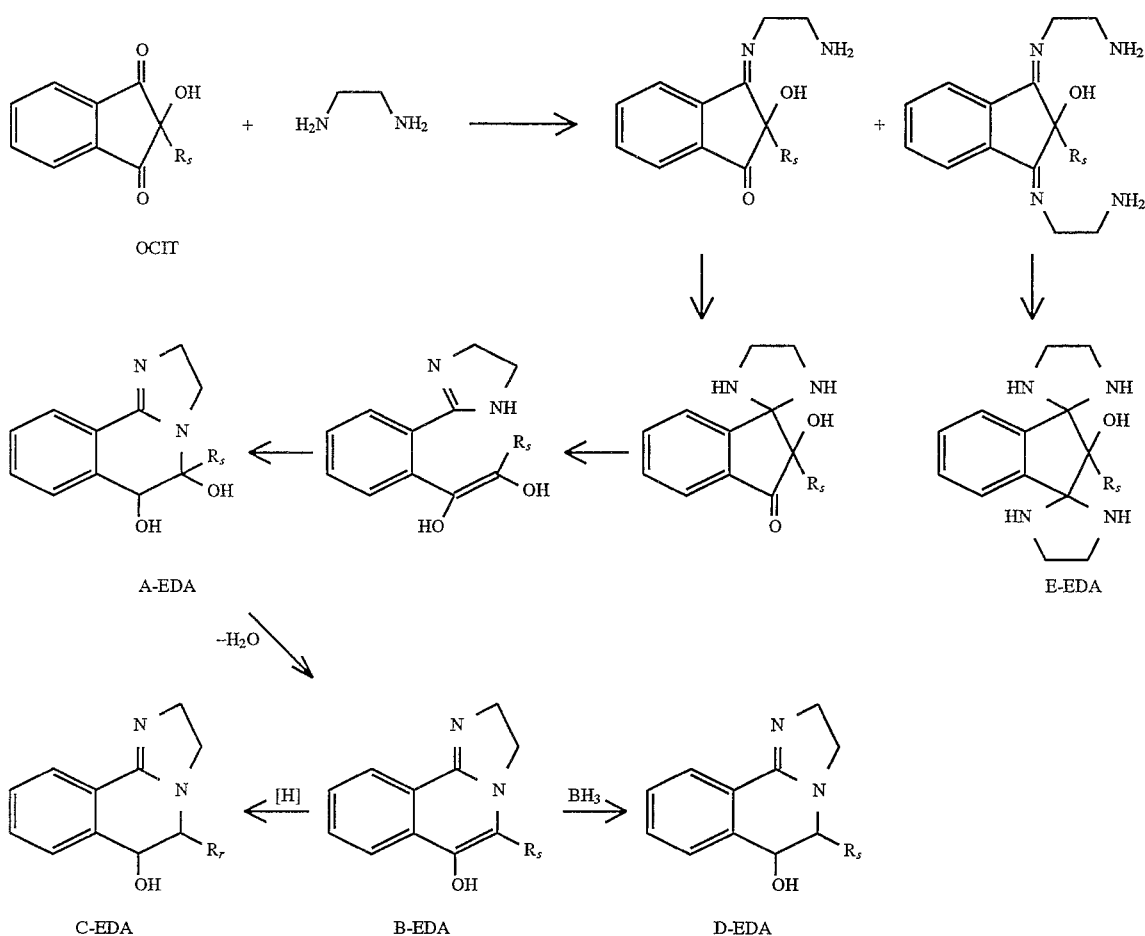

A-EDA

E-EDA

C-EDA  B-EDA  D-EDA

Example C8

About 8.2 grams of ODIT dissolved in 20 ml of dioxane, and 1.2 grams of EDA in 20 ml of dioxane were combined. The resulting mixture warms slightly, and turns dark and cloudy. After stirring at room temperature, the mixture becomes clear. After stirring for 6 days at room temperature, the solution is rotoevaporated, and the residue is diluted in 100 ml of diethyl ether which induces the product to precipitate. The solid product, F-EDA, is recrystallized from a dioxane-ether mixture. The recrystallizate (F-EDA), m.p. 124°–127° C., analyzes for 76.10% carbon, 9.93% hydrogen, and 5.93% nitrogen (Theory for F-EDA requires 76.65% carbon, 10.13% hydrogen, and 6.17% nitrogen), features an IR with a strong C=N absorption band at 6.15 microns; and shows a CI mass spectrum with a protonated peak at m/e=437 which corresponds to G-EDA which is the dehydrated derivative of F-EDA.

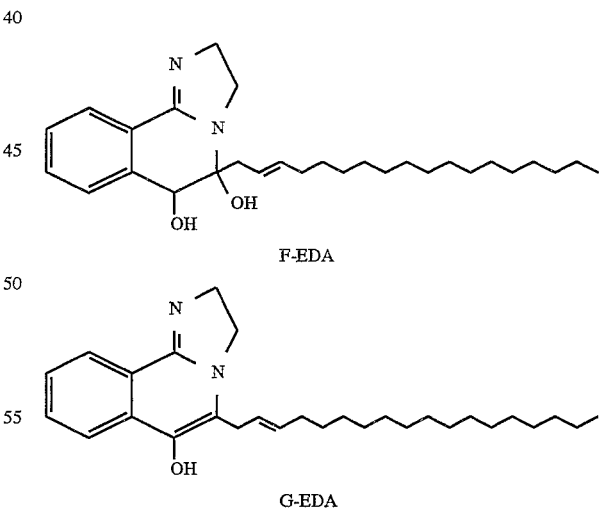

F-EDA

G-EDA

Example C9

About 27 grams of OCIT and 10.8 grams of o-phenylene diamine (1,2-diamino-benzene) were added to 200 ml of xylene at room temperature. The reaction mixture was stirred at reflux in a nitrogen-blanketed reactor fitted with a moisture trap to collect the water of reaction. After 12 hours of refluxing, 1.5 ml of water were collected, and the reaction mixture was rotoevaporated at 100° C. for 4 hours. The residue was diluted with 200 ml of diethyl ether, and filtered. The solids (A-OPD) were recrystallized from tetrahydrofuran, and dried, m.p. 131°–133° C. The recrystallizate analyzed for 76.29% carbon, 7.30% hydrogen, 7.71% nitrogen, and 8.63% oxygen (Theory for A-OPD requires 76.24% carbon, 7.18% hydrogen, 7.74% nitrogen, and 8.84% oxygen), and featured a CI mass spectrum with a protonated molecular ion at m/z=363. An X-ray crystal structure analysis confirmed the proposed structure, A-OPD, as shown below.

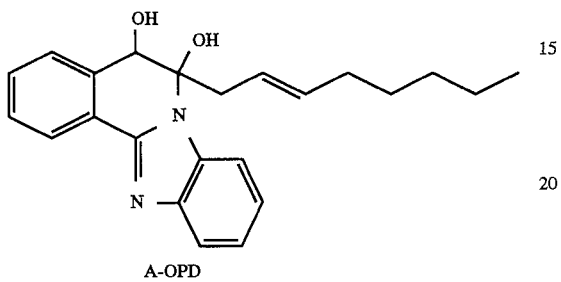

A-OPD

Example C10

Two millimoles of OCIT and 0.14 gram of 1,3-propanediamine (PDA) were mixed together in 5 ml of dioxane, and stirred at room temperature for about 6 days. Evaporation of the mixture at room temperature gave a residue which featured an IR spectrum with a strong C=N absorption band at 6.18 microns, a CI mass spectrum with protonated ions at m/z=311 and 329 which correspond to structures A-PDA, and its dehydrated analog, B-PDA (see below).

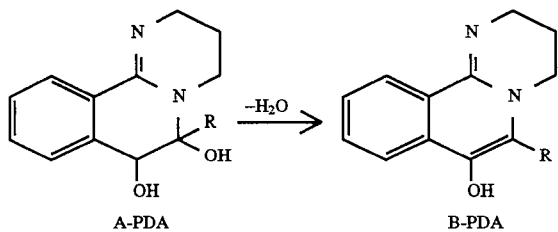

A-PDA        B-PDA

Example C11

About 4.1 grams(0.01 mole) of ODIT dissolved in 20 ml of dioxane, and 1.4 grams (0.19 mole) of 1,3-propanediamine dissolved in 20 ml of dioxane, were combined to give a solution which was stirred at room temperature for 4 days. Solids formed, and the mixture was diluted with 50 ml of diethyl ether, and filtered. The solids were recrystallized from dioxane, and dried, m.p. 97°–99° C. The recrystallizate (C-PDA) analyzed for 75.28% carbon, 10.62% hydrogen, and 5.91% nitrogen (Theory for the hemi-hydrate of C-PDA requires 75.31% carbon, 10.25% hydrogen, and 5.86 % nitrogen), and featured an IR spectrum with a C=N absorption band at 6.15 microns in harmony with the proposed structure shown below for C-PDA.

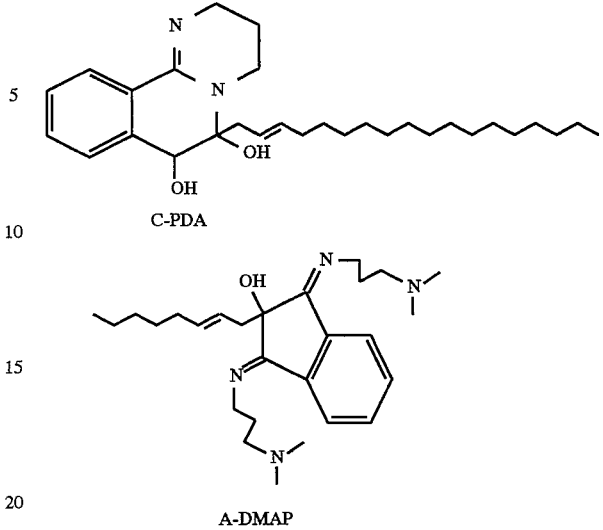

C-PDA

A-DMAP

Example C12

A solution of 0.51 gram of OCIT in 2 ml of dioxane and a solution of 1 gram of 3-dimethylaminopropylamine in 3 ml of dioxane were combined and stirred at room temperature for several days. Rotoevaporation of the mixture at 80° C. for 4 hours gave a residue which featured a CI mass spectrum with a protonated molecular ion at m/z=441, and an IR spectrum with a strong C=N absorption band at 6.05 microns. These spectral data and the cmr spectrum of the product are consistent with structure A-DMAP, shown above.

Example C13

N-Methyl-EDA (0.8 gram) and OCIT (2.8 grams) were dissolved in 3 ml of dioxane and stirred at room temperature for 4 days. Rotoevaporation of the mixture for 6 hours at 80° C. gave a residue which featured an IR spectrum with absorption bands at 5.8 and 6.06 microns, and a mass spectrum with a protonated peak at m/z=329.

A similar experiment with N-ethyl-EDA and OCIT afforded a 1:1 product with an IR spectrum with bands at 5.8 and 6.1 microns, and a mass spectrum featuring a protonated molecular ion at m/z=343. Doubling the amount of N-ethyl-EDA gives an mixture with an IR spectrum featuring a broad band at 6 microns and a mass spectrum with protonated ions at m/z=343 and 413.

Example C14

About 0.13 gram of 3,3'-imino-bis-propylamine (IBPA) and 0.54 gram of OCIT were dissolved in 3 ml of dioxane, and stirred at room temperature for about 5 days. Rotoevaporation of the mixture gave a residue with a mass spectrum featuring a protonated ion at m/z=499.

Example C15

About 0.20 gram of diethylenetriamine (DETA), and 0.54 Gram of OCIT were dissolved in 3 ml of dioxane, and stirred at room temperature for four days. Rotoevaporation Gave a residue which featured a mass spectrum with a protonated peak at m/z=358.

Amino alcohol reactions

Example C16

About 0.54 gram of OCIT and 0.24 gram of 2-aminoethanol (AE) were combined in 5 ml of dioxane, and stirred at 100° C. for 18 hours. Rotoevaporation of the mixture at 80° C. for 4 hours gave a residue which showed an IR with absorption bands at 5.8 and 6 microns, and a CI mass spectrum with protonated ions at m/z=316, and 359.

Example C17

Ten millimoles of ODIT in 25 ml of DMSO and 2.4 grams of tris-(hydroxymethyl)aminomethane (THAM) in 25 ml of DMSO were combined and stirred at about 120° C. for 2 days. Rotoevaporation of the mixture at 100° C. for 8 hours gave a residue with an IR spectrum featuring an absorption band at 6.05 microns. Carbonyl bands at 5.72 and 5.85 microns ascribable to the reactant, ODIT, were conspicuously absent. A FAB mass spectrum of the residue featured a protonated ion at m/z=498.

Example C18

About 0.54 gram of OCIT and 0.15 gram of 2-aminoethanethiol (cysteamine) were combined and stirred at 60° C. for about 8 days. Rotoevaporation of the mixture at 80° C. for 4 hours gave a residue which featured an IR spectrum with absorption bands at 5.8, and 6.0 microns, and a mass spectrum with a protonated molecular ion at m/z=332.

Alcohol reactions

Example C19

About 5.4 grams of OCIT, 3.7 grams of glycerol, 1 drop of sulfuric acid, and 50 ml of xylene were stirred at reflux in a nitrogen-purged reactor fitted with a moisture trap. After 16 hours of refluxing, about 0.8 ml of water was collected. Rotoevaporation of the reaction mixture at 100° C. for 8 hours gave a residue which featured an IR spectrum with two carbonyl absorption bands at 5.62 and 5.8 microns, and a CI mass spectrum having protonated ions at m/z=347, and 421. The intensity ratio of the protonated ions was about 5:1, respectively Alloxan Adducts and Products Example D1

Fifty millimoles (12.6 grams) of 1-octadecene dissolved in 12.5 grams of 1,4-dioxane were heated in a magnetically stirred, nitrogen blanketed reactor fitted with a reflux condensor and a thermometer. To the refluxing (ca. 102° C.) solution was gradually added fifty millimoles (8.0 grams) of alloxan (AX) hydrate dissolved in 80 ml of dioxane. After the addition of alloxan, the mixture was refluxed for about six hours. After standing overnight at room temperature, the reaction solution turned into a solid crystalline mass which, upon heating, redissolved in dioxane. The reaction mixture was heated to about 130° C. for about 8 hours, and then cooled overnight. The crystals that separated from solution were filtered off, and subsequently recrystallized from dioxane. The dried crystals melted at 102°–104° C. and analyzed for 64.32% C, 9.38% H, and 6.80% N. Theory for the monohydrate of the ene adduct requires 64.07% C, 9.71% H, and 6.80% N. The crystalline product featured an infrared spectrum with intense twin carbonyl absorptions at about 5.85 and 5.92 microns, a carbon magnetic resonance spectrum with characteristic sp2 carbon signals at about 170.3, 148.3, 138.3 and 119.5 ppm, and a CI mass spectrum with a protonated molecular ion at m/z=395, thus confirming the molecular weight of 394 for the ene adduct, 5-(2-octadecenyl) dialuric acid (OX) shown below (wherein $R_u$=H):

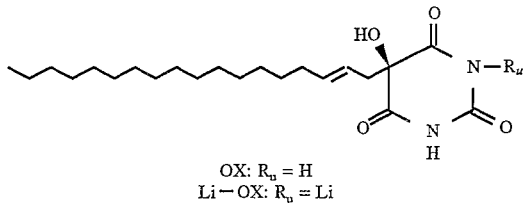

OX: $R_u$ = H
Li—OX: $R_u$ = Li

Example D2

A half gram of OX dissolved in 20 ml of hot methanol, and 90 mg of lithium isopropoxide in 10 ml of hot methanol were combined and stirred at room temperature. After about 30 minutes, the clear solution became cloudy, and a precipitate formed. Filtration gave a white solid which, after drying, featured an IR spectrum with intense absorption bands at 6.0, and 6.5 microns, a CMR spectrum in DMSO-$d_6$ with signals at 186, 170, 169, 134, 123, and 86 ppm, and analyzed for 6.67% nitrogen, and 1.73% lithium (Theory for the mono-lithium salt of OX [Li-OX] requires 6.98% nitrogen, and 1.75% lithium). The spectral and analytic data are consistent with the structure, Li-OX (wherein $R_u$=Li), shown above.

Example D3

Three grams of OX, 6.6 grams of magnesium methoxide (8 wt % solution in methanol), and 50 ml of anhydrous methanol were combined in a nitrogen-blanketed reactor, and stirred at room temperature for about 5 days. Filtration gave a filter cake which was dried in vacuo for 8 hours at room temperature. The dried solids featured an infrared spectrum with intense absorption bands at about 5.95 and 6.4 microns, showed a CMR spectrum in acetic acid-$d_4$ virtually identical to OX, and analyzed for 5.55% nitrogen and 8.02% magnesium.

Substituted Alloxan Adducts

Example D4

Eight grams (0.05 mole) of AX hydrate were added to 60 ml of dioxane in a nitrogen-blanked reactor fitted with thermometer, magnetic stirrer, addition funnel, and reflux condensor. The reaction mixture was heated to reflux, and 18.5 ml of oleyl alcohol (85%) were added dropwise over a 15 minute span. Refluxing the mixture for about an hour produced a clear solution which was heated at reflux for about 24 hours. Rotoevaporation of the reaction mixture afforded a residue, which was filtered and analyzed. A supercritical fluid chromatogram of the residue confirmed the presence of product. The residue featured an infrared spectrum with characteristic hydroxyl, and amido carbonyl absorption bands, and a mass spectrum (protonated ion at m/z=411) consistent with one or more isomeric ene adducts of oleyl alcohol and alloxan as typified by two possible isomeric products as shown below:

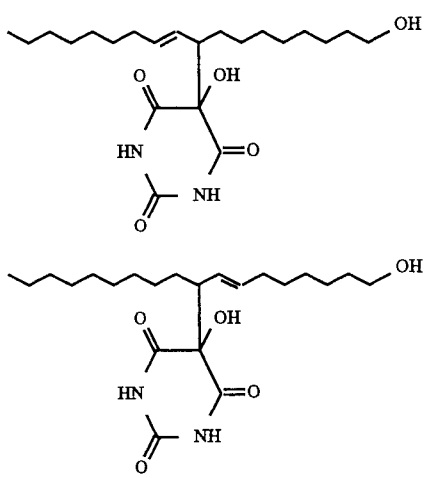

Example D5

In the same manner as described in Example D4, 8 grams of AX hydrate, 15.9 grams of oleic acid, and 60 ml of dioxane were combined in a reactor, and stirred at reflux temperature for 8 hours. The reaction mixture completely dissolved after an hour, and refluxing was continued for another 24 hours. Evaporation of the mixture gave a residue which was filtered and analyzed. A supercritical fluid chromatogram of the residue showed a broad product peak. The residue also featured an infrared spectrum with carbonyl absorption bands ascribable to carboxy and caraboxamido carbonyl functionality, and a mass spectrum featuring a protonated ion at m/z=425 which confirms the structure for the ene adduct of AX and oleic acid.

Example D6

A mixture of 4.8 grams (0.03 mole) of AX, 10 ml of methyl oleate, and 50 grams of dioxane was combined in a nitrogen-blanketed reactor, and stirred at reflux for 24 hours. Rotoevaporation afforded a residue which featured a supercritical fluid chromatogram with a product peak, an infrared spectrum with strong ester and amide carbonyl absorption bands, and a mass spectrum (protonated ion at m/z=439) consistent with the proposed isomeric ene adducts shown below:

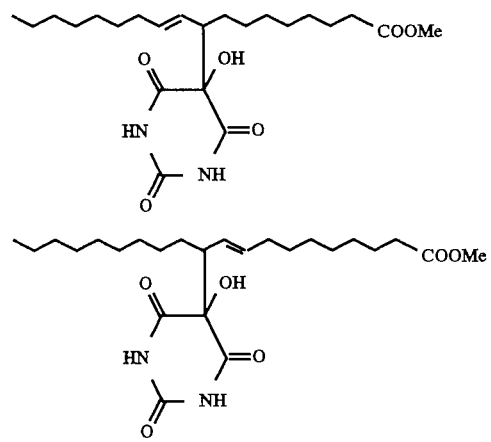

Example D7

Eight grams (0.05 mole) of AX hydrate and 50 ml of n-butanol were combined in a nitrogen-blanketed reactor, and stirred at reflux temperature until a clear solution was obtained (about an hour). Nineteen ml of oleyl alcohol ethoxylated with about two moles of ethylene oxide was added, and the mixture was refluxed for 8 hours. The reflux temperature was then increased to about 130° C. by distilling off some of the butanol. Heating at 130° C. was continued for about 24 hours. Evaporation gave a residue which featured an infrared spectrum with a strong amide carbonyl, and ether absorption bands, a supercritical fluid chromatogram with about 10 adduct peaks, and a thermospray mass spectrum a multiplicity of peaks including protonated molecular ions at m/z=411, 455, 499, 543, 587, 631, 675, 719, 763, 807 and 851. These major peaks correspond to isomeric alloxan adducts of oleyl alcohol ethoxylated with 0 to 10 moles of ethylene oxide, respectively as depicted in part by the structures featured below:

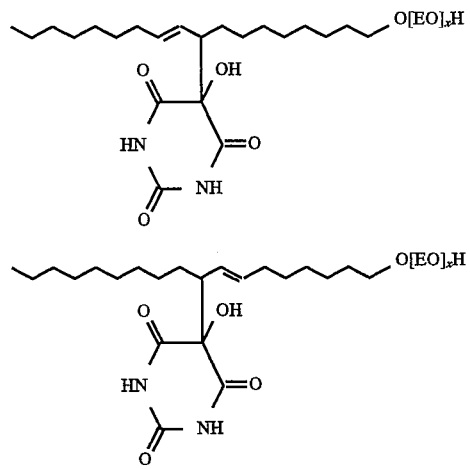

In another series of experiments similar to those illustrated in Examples C4 to C7, a wide spectrum of novel ene adducts were produced to demonstate the ene reactivity of the cyclic carbonyl monomers of the present invention such as indantrione, alloxan, 1,3-dimethylalloxan, and dehydroascorbic acid with oleyl alcohol, methyl oleate, methyl linoleate, methyl linolenate, oleic acid, linoleic acid, linolenic acid, ethoxylated oleyl alcohol, and methyl oleyl ketone.

Reactions of ene adducts of AX

To further demonstrate the preparation of products from alloxan (AX)-hydrocarbon adducts, a variety of reactions of said adducts with reagents such as amines, polyamines, amino alcohols, alcohols, and polyols were carried out, some of which are set forth below.

Amine Reactions

Example D8

To 4 grams of OX dissolved in about 50 ml of dioxane stirred at 40° C., were added dropwise 1 gram of n-butylamine dissolved in 5 ml of dioxane. Solids immediately separated from solution during the addition of the butylamine, and the reaction temperature climbed to about 43° C. Following addition of the amine, the stirred reaction mixture was allowed to cool to room temperature, and then filtered. The white powder, after drying, melted at 140°–145°, featured a single peak in a supercritical fluid chromatogram, a mass spectrum with a protonated molecular ion at m/z=468, an elemental analysis of 66.19% carbon, 10.04% hydrogen, 8.79% nitrogen (Theory for a 1:1 salt of OX and butylamine) requires 66.81% carbon, 10.49% hydrogen, and 8.99% nitrogen), and a carbon magnetic resonance spectrum consistent with salt formation between OX and butylamine.

Example D9

About 2 grams of OX, and 15 ml of n-butylamine were stirred at 60° C. until a clear solution was obtained. The reaction solution was then stirred at 70° C. for 5 hours, and allowed to cool to room temperature. The solids that separated from solution were isolated, dried, and analyzed by infrared spectroscopy to be urea. Rotoevaporation of the supernatent at 80° C. for 4 hours afforded a residue which featured an infrared spectrum with a strong amide absorption band centered at about 6 microns, a mass spectrum having a protonated molecular ion at m/z=481, and a carbon magnetic resonance spectrum consistent with the bis-amide structure: OX-B shown below:.

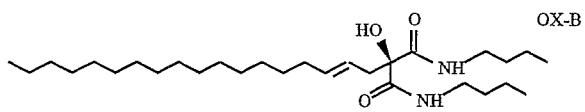

Polyamine Reactions

Example D10

Four grams of OX were combined with 20 grams of ethylene diamine of about 5° C. and then allowed to warm to room temperature. The mixture became clear after 15 minutes, and was stirred at about 25° C. for several days. Rotoevaporation of the mixture gave a residue (OX-C) which analyzed for 11.31% nitrogen (Theory for the hydrate requires 11.86% nitrogen); showed an infrared spectrum with a strong amide carbonyl band centered at about 6.1 microns, a CMR spectrum (DMSO-d$_6$) with carbonyl, olefin (2), carbinol, and N-methylene signals at 171, 133.8, 123.4, 78.2, and 42.4 ppm, respectively, and a mass spectrum with an intense protonated peak at m/z=455, thus confirming the presence of the bis-amidoamine product, namely, N,N'-bis-(2-aminoethyl) 2-(2-octadecenyl) tartronamide (OX-C), as shown below:

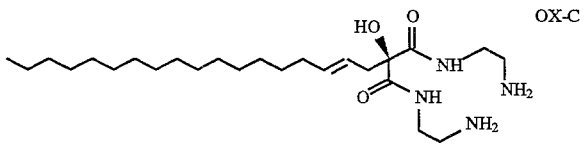

The bis-amidoamines are useful as friction modifiers, flow improvers, 2-cycle engine additives and fuel additives. Owing to their ability to function as tetradentate ligands, the bis-amidoamines readily form stable complexes with transition metals; moreover, the copper complex features A/O properties, and can be used in lube formulations as an antioxidant.

Example D11

About 1.7 grams of the ene adduct of 1-octene and 1,3-dimethyl-alloxan, and 2 grams of 3-(dimethylamino) propylamine were added to 20 ml of xylene in a nitrogen blanketed reactor, and the stirred mixture was refluxed for about 24 hours. Rotoevaporation afforded a residue which featured an IR spectrum with carbonyl bands at 5.5, 5.72, and 5.95 microns.

Example D12

About 0.4 gram of OX, 0.15 gram of triethylenetetramine (TETA), and 5 ml of dioxane were added to a nitrogen blanketed reactor equipped with stirrer and reflux condensor, and then heated at 60° C. for 6 hours. Rotoevaporation of the filtered reaction mixture gave a residue, OX-TETA, which featured an infrared spectrum having a strong amide carbonyl absorption band centered at 5.9 microns, a mass spectrum featuring a protonated molecular ion at m/z=481, and an elemental analysis for 10.99% nitrogen (Theory requires 11.24% for the hydrate of OX-TETA). The analytic data confirm the macrocyclic polyamine structure for OX-TETA as shown below::

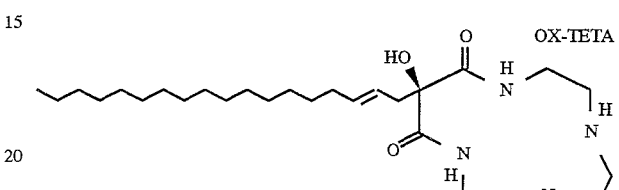

In a similar manner, polymers bearing macrocyclic polyamine functionality were prepared via the reaction of equimolar quantities of alloxan adducts of EB copolymer ($M_n$=2K) with a polyamine such as 3,3'-imino-bis-propylamine, diethylene-triamine, triethylenetetramine, 1,3-bis-(2-amino-ethyl)-1,3-propanediamine, 1,3-bis-(3-aminopropyl)-1,3-propanediamine, tetra-ethylenepentamine (TEPA), and polyamine-H (a mixture of higher ethyleneamines including pentaethylenehexamine).

Example D13

Four grams of OX and 1.6 grams of bis-1,3-(2-aminoethyl)-1,3-propanediamine (BAP), and 50 ml of dioxane were added to a nitrogen purged reactor fitted with thermometer, magnetic stirrer, and reflux condensor. The mixture gradually dissolved upon heating to 60° C. for a half hour. The clear solution was stirred at 60° C. for five hours, then cooled, filtered, and rotoevaporated. The residue which contains OX-BAP, featured an infrared spectrum having an intense amide carbonyl absorption band at 5.9 microns, a supercritical fluid chromatogram with a single product peak, a mass spectrum with a protonated molecular ion at m/z= 495, and an elemental analysis of 12.02% nitrogen (Theory for the macrocycle requires 11.34% nitrogen). The analytical data are consistent with the macrocyclic amidoamine structure, OX-BAP, illustrated below.

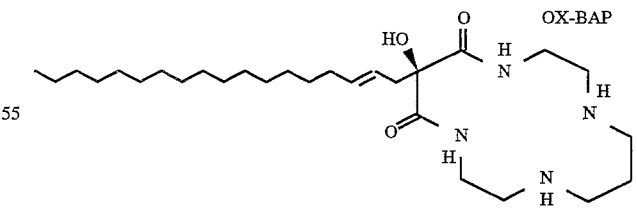

OX-BAP was also obtained via aminolysis of diethyl 2-octadecen-2-yl tartronate, with a mole of BAP.

Metal Complexes

Example D14

One gram of the macrocyclic amidoamine derived from OX and triethylene tetraamine (TETA) described in Example D12, and 0.53 grams of cupric acetylacetonate, were dissolved in 50 ml of hot methanol, and stirred at room temperature for about 4 weeks. The reaction mixture was heated to boiling, and filtered hot. Rotoevaporation of the filtrate gave a solid product, OX-TETA-Cu, which featured an IR spectrum with a strong absorption band at 6.3 microns, a FAB MS with a molecular ion at m/z=541, and analyzed for 9.34% nitrogen, and 12.04% copper (Theory for the OX-TETA-Cu neutral complex requires 10.29% nitrogen, and 11.76% copper). The structure for OX-TETA-Cu is shown below.

[3MeOH] complex requires 8.66% nitrogen, and 9.12% nickel). The structure for the OX-BAP-Ni neutral complex is depicted in the formula above wherein $M_z$=Ni.

Amino alcohol reactions

Example D17

Four grams of OX dissolved in 30 ml of DMSO and 2.4 grams of THAM were combined and stirred at 120° C. for several days. Rotoevaporation afforded a residue which showed an IR spectrum with ester and amide carbonyl

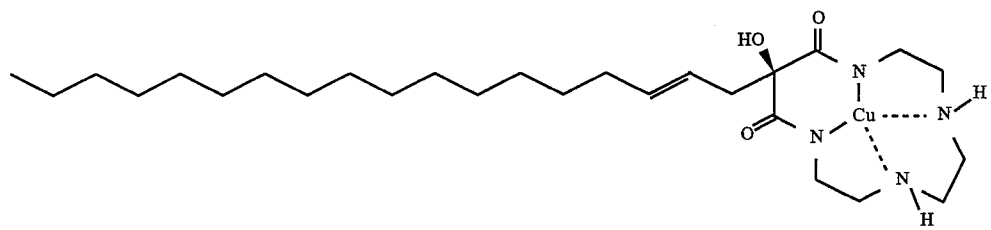

OX-TETA-Cu

Example D15

Three grams of the OX-BAP product of Example D13, and 1.6 grams of cupric acetylacetonate in 150 ml of methanol, were combined and stirred at 30° C. for about 24 hours, and then refluxed for about 5 hours. Filtration of the mixture gave a supernatent which was concentrated by evaporation. The methanol solution, upon dilution with ether, gave a crystalline product, OX-BAP-Cu, which showed a UV spectrum with absorption bands at 293.2, and 243 nanometers (in dioxane), featured an IR specrum with absorption bands at about 6.3 and 6.5 microns, gave a FAB MS with a molecular ion at m/z=555 and analyzed for 9.79% copper (Theory for the OX-BAP-Cu[3MeOH] complex requires 9.83% copper). The proposed structure for the neutral complex, OX-BAP-Cu, is shown in the formula below wherein $M_z$=Cu.

absorption bands at 5.8 and 6.0 microns, and a FAB mass spectrum with a protonated ion at m/z=456.

Alcohol reactions

Example D18

About 0.4 Gram of OX, 20 mG of DBU, and 4 ml of n-butanol were stirred at 90° C. for about 24 hours. Rotoevaporation of the solution gave a residue which featured an IR spectrum with carbonyl bands at 5.75 and 5.85 microns and a CI mass spectrum with protonated ions at m/z=469 and 483.

Polyol reactions

Example D19

One gram of OX, 4 grams of glycerol, and 20 milligrams of DBU were stirred at about 120° C. for about 24 hours. The

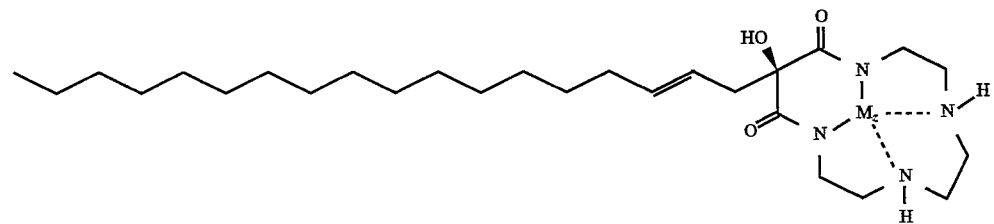

OX-BAP-Cu($M_z$ = Cu); OX-BAP-Ni($M_z$ = Ni)

Example D16

Three grams of OX-BAP of Example C13, 1.5 grams of nickel acetylacetonate, and 20 ml of methanol were combined, and stirred at room temperature for 9 days. The green solution was filtered, concentrated by passing a stream of nitrogen over the surface of the solution, and diluted with diethyl ether. Cooling the methanol-ether solution induced the precipitation of solids which were isolated by filtration and dried. The green solids featured an IR spectrum with a strong absorption band at 6.3 microns,a FAB mass spectrum with a protonated peak at m/z=552, and analyzed for 8.40% nitrogen, and 9.37% nickel (Theory for the OX-BAP-Ni reaction product featured an IR spectrum with an ester carbonyl band at about 5.75 microns, and a CI mass spectrum with a protonated ion at m/z=427.

Example D20

About 4.1 grams of OX in 35 ml of DMSO, 2.7 grams of pentaerythritol (PE) in 20 ml of DMSO, and 30 mg of DBU were combined in a nitrogen sparged reactor, and stirred at 120° C. for about 24 hours. Rotoevaporation of the reaction mixture at 120° C. for 8 hours Gave a residue (OX-PE) which featured an IR spectrum with ester carbonyl absorption bands at 5.75 and 5.8 microns, and a field desorption (FD) mass spectrum with a protonated molecular ion at m/z=607 in harmony with the OX-PE structure shown below:

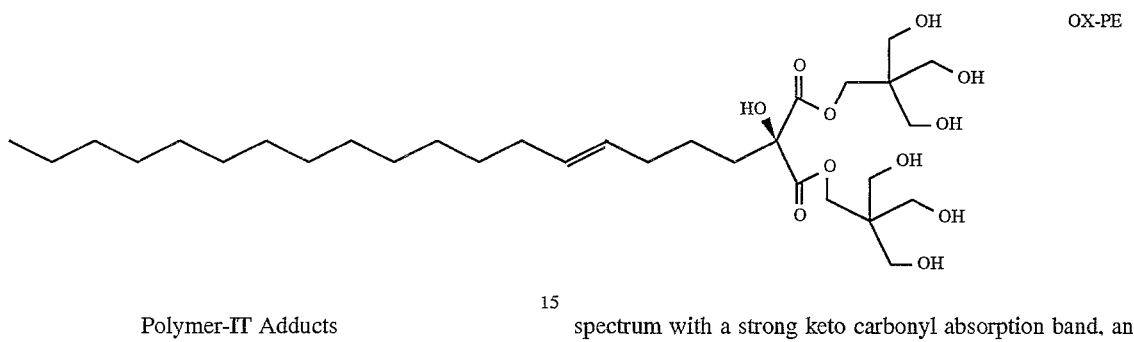

Polymer-IT Adducts

Example E1

Ten grams of polyisobutylene with $M_n \approx 950$, and 2 grams of IT were combined in a reactor blanketed with nitrogen, and stirred at 150° C. for 28 hours. The cooled mixture was diluted with about 100 ml of cyclohexane, and filtered. Rotoevaporation of the filtrate gave a residue which featured an infrared spectrum with a strong keto carbonyl absorption band at about 5.85 microns, and analyzed for 3.96% oxygen.

Example E2

About 24 grams of polyisobutylene, $M_n \approx 2.4K$, was heated to 170° C. in a nitrogen blanketed reactor. The stirred polymer was ene-reacted with anhydrous IT via the dropwise addition of 50 ml of a dioxane solution containing 1.6 grams of IT. After removing the dioxane by distillation, the mixture was stirred at 170° C. for about 24 hours, and subsequently rotoevaporated for 8 hours at about 100° C. The residue analyzed for 1.67% oxygen, and featured an infrared spectrum with a strong ketone carbonyl adsorption band at about 5.8 microns.

Example E3

A tenth mole of poly-n-butene with $M_n \approx 550$, and 17.8 grams of IT hydrate were combined, and stirred at about 160° C. for 16 hours. The mixture was diluted with about 100 ml of cyclohexane, and filtered. Rotoevaporation of the filtrate afforded a residue which featured an infrared spectrum with a dominant keto carbonyl absorption band at about 5.8 microns, and analyzed for 3.39% oxygen.

Example E4

Forty grams of ethylene butene-1 (EB) copolymer with $M_n \approx 1.9$, and 55 wt % ethylene, and 3.6 grams of IT hydrate were combined in a nitrogen-blanketed reactor, and stirred at 155° C. for 4 hours. Rotoevaporation of the mixture for 4 hours at 100° C. gave a residue which featured an infrared spectrum having twin carbonyl bands at 5.7 and 5.82 microns, and analyzed for 2.11% oxygen. Chromatographic analysis indicated that 75.2% of the EB polymer was grafted with IT monomer. Based on the oxygen analysis and chromatographic data, the functionality level, n, is calculated to be 1.33.

Example E5

About forty grams of EB copolymer ($M_n \approx 1.9K$, and 55 wt % ethylene) and 4 grams (0.025 mole) of anhydrous IT were combined in a nitrogen-blanketed reactor, and stirred at 160° C. for about 10 hours. Rotoevaporation of the mixture for about 8 hours at 100° gave a residue which featured an IR spectrum with a strong keto carbonyl absorption band, and analyzed for 2.41% oxygen.

Example E6

Forty grams of EB copolymer ($M_n \approx 2K$, and 55 wt % ethylene) were stirred at 160° C. in a nitrogen blanketed reactor while 40 ml of tetrahydrofuran containing 3.2 grams of sublimed IT were added dropwise over an hour period. The reaction mixture was stirred at 160° C. for about 5 hours, and then rotoevaporated for about 8 hours at 100° C. The residue featured an infrared spectrum with a strong carbonyl band at 5.8 microns, and analyzed for 2.24% oxygen.

Example E7

In similar fashion, 40 grams of EB copolymer ($M_n \approx 2K$, and 55 wt %) and 5 grams of sublimed IT were combined and stirred at 160° C. in a nitrogen-blanketed reactor for 8 hours. The adduct contained 3.49% oxygen, and featured an IR spectrum with a strong carbonyl absorption at 5.8 microns. Chromatographic analysis indicated that 90.3% of the EB polymer was modified with the IT monomer.

To ascertain the effect of IT-functionality on the thermal oxidative stability of the above polymer adduct, the starting EB polymer and the IT-treated EB polymer were submitted for thermogravimetric analysis (TGA) which basically measures weight loss due to oxidative degradation as the polymers are heated gradually to 350° C. in the presence of air. The TGA data shown below in Table 1 clearly indicate that the functionalization of the EB polymer with IT according to the instant synthetic protocol, significantly stabilizes the above described polymer mixture toward thermal oxidative degradation.

TABLE 1

TEMPERATURE RAMPED TGA (10° C./minute) OF STARTING POLYMER (EB) AND ADDUCT (EBIT) CUMULATIVE WEIGHT LOSSES (% OF INITIAL WT.) AIR (100 ml/minute)

| Sample | 150° C. | 200° C. | 250° C. | 300° C. | 350° C. |
|---|---|---|---|---|---|
| EB | 0.31 | 1.26 | 4.10 | 12.34 | 38.67 |
| EBIT | 0.13 | 0.79 | 2.40 | 6.70 | 13.14 |

Example E8

One hundred grams of EB copolymer with $M_n \approx 3.2$ and 46 wt % ethylene, and 6 grams of sublimed IT (20 mole % excess) were combined and stirred at 155° C. for about eleven hours. Analyses indicated that 79.4% of the EB polymer was functionalized, and that the functionalized polymer contained 1.62% oxygen indicating that the functionality factor, n=1.26. The IR spectrum of the adduct featured a strong carbonyl absorption at 5.82 microns. Ultraviolet (UV)- and Differential Refractive Index (DRI)-GPC analyses of the mother EB polymer and the IT-functionalized EB polymer indicated that the polymer was uniformly modified with the IT monomer, and that the molecular weight distribution of the mother polymer was retained.

Example E9

In similar fashion, the ene addition of 7.8 grams of IT hydrate (40 mole % excess) to 100 grams of EB copolymer ($M_n \approx 3.2K$, and 46 wt % ethylene) conducted at 155° C. for about ten hours afforded the expected adduct which analyzed for 1.75% oxygen. Chromatographic analysis indicated that 74.9% of the EB polymer was functionalized, indicating that the functionality factor, n,was 1.34. UV- and DRI-GPC analyses of the mother EB polymer and the IT-functionalized EB polymer indicate that the polymer is uniformly modified with the IT monomer, and that the molecular weight distribution of the mother polymer is retained. The GPC trace of the functionalized polymer and the mother polymer were comparable.

Example E10

Thirty six grams of EB copolymer ($M_n \approx 1.9K$ with 55 wt % ethylene) and 3.6 grams of IT hydrate were combined, and stirred at 165° C. in a nitrogen blanketed reactor for about an hour. The adduct featured an infrared spectrum with a strong carbonyl band at 5.75 microns and analyzed for 2.1% oxygen. Moreover, chromatographic analysis of the adduct indicated that 86.5% of the EB copolymer was functionalized.

To ascertain the effect of IT-functionality on the thermal oxidative stability of the above polymer adduct, the starting EB polymer and the IT-treated EB polymer were submitted for thermogravimetric analysis (TGA) which basically measures weight loss due to oxidative degradation as the polymers are heated gradually to 350° C. in the presence of air. The TGA data shown below in Table 2 clearly show that the functionalization of the EB polymer with IT according to the instant synthetic protocol, significantly stabilizes the above described mixture of EB polymer and polymer adduct (EBIT) toward thermal oxidative degradation.

TABLE 2

TEMPERATURE RAMPED TGA (10° C./minute)
OF STARTING POLYMER (EB) AND ADDUCT (EBIT)
CUMULATIVE WEIGHT LOSSES (% OF INITIAL WT.)
AIR (100 ml/minute)

| Sample | 150° C. | 200° C. | 250° C. | 300° C. | 350° C. |
|---|---|---|---|---|---|
| EB | 0.32 | 1.36 | 4.14 | 12.44 | 38.70 |
| EBIT | 0.14 | 0.79 | 2.42 | 6.70 | 13.16 |

Polymer-IT Products

Example F1

Forty grams of poly-n-butene with $M_n \approx 2K$, and 3.2 grams of sublimed IT were combined in a nitrogen blanketed reactor, and mechanically stirred at a temperature of 160° C. for about 5 hours. The reactor was cooled to about 100° C., and 1.9 grams of tetraethylene pentamine (TEPA) were added dropwise over 10 minutes. The mixture was stirred at about 120° C. for about 4.5 hours while the reactor was swept with a strong current of nitrogen to remove the water formed during condensation of the polyamine with the IT-modified poly-n-butene. Rotoevaporation of the mixture for about 8 hours at 100° C. gave a residue free of unreacted TEPA. Elemental analysis indicated that the residue contained 1.42% nitrogen.

Example F2

A mixture of one hundred ten grams (0.05 mole) of an unhydrogenated poly-alpha-olefin derived from decene-1 with $Mn \approx 2.2K$, and 8.9 grams (0.05 mole) of IT hydrate was stirred at 160° C. for about 4 hours. A sample of the reaction product featured an infrared spectrum consistent with the expected ene adduct. Thereafter, 0.02 mole of tetraethylenepentamine (TEPA) was added to the remaining adduct (ca. 0.04 mole), and the mixture was stirred at about 120° C. for about 16 hours. Rotoevaporation of the reaction mixture for 8 hours at about 100° C. afforded a residue which analyzed for 0.54% nitrogen.

Example F3

The reaction mixture obtained in Example E10 was cooled to about 80° C., and 3.0 grams of linear triethylene tetramine (TETA) were added gradually over a 2 minute period. Following the addition of the TETA, the mixture was then stirred at 80° for about an hour, and rotoevaporated for 2 hours at 80° C. The product displayed an infrared spectrum with two broad absorption bands at 5.9 and 6.05 microns, and analyzed for 4.24% nitrogen. Chromatographic analysis indicated that the 1:1 mole product contained less than 0.3% residual TETA.

Example F4

Thirty six grams of EB copolymer ($M_n \approx 1.9K$ and 55 wt % ethylene) and 3.6 grams of IT hydrate were combined, and stirred at 160° C. in a nitrogen blanketed reactor for about an hour. The adduct featured an infrared spectrum with a strong carbonyl band at 5.75 microns and an elemental analysis for 2.14% oxygen. Moreover, chromatographic analysis of the adduct indicated that 86.5 % of the EB copolymer was functionalized. The reaction mixture was cooled to about 80° C., and 1.5 grams of linear triethylene tetramine (TETA) were added gradually over a 2 minute period. Following the addition of TETA, the mixture was then stirred at 100° C. for about an hour, and rotoevaporated for 2 hours at 80° C. The product displayed an infrared spectrum with a broad absorption band at 5.9 microns, and analyzed for 1.58% nitrogen.

Chromatographic analysis indicated that the product contained less than 0.067% residual TETA. To ascertain the effect of functionality on the thermal oxidative stability of the above dispersant product, the starting EB polymer, the IT-treated EB polymer (adduct), and the TETA-treated adduct (dispersant product) were submitted for thermogravimetric analysis (TGA). As indicated above, TGA measures weight loss due to oxidative degradation as the polymers are heated gradually to 350° C. in the presence of air.

A comparison of the TGA data shown below in Table 3 for the three polymers clearly indicate that the adduct and dispersant product are significantly more stable than the starting polymer toward thermal oxidative degradation. It is plausible that the ene diol and ketol products generated during amination may contribute to the outstanding thermal oxidation stability of the dispersant.

TABLE 3

TEMPERATURE RAMPED TGA (10° C./minute)
OF STARTING POLYMER (EB), ADDUCT (EBIT) AND
DISPERSANT PRODUCT (2:1 EBIT-TETA)
CUMULATIVE WEIGHT LOSSES (% OF INITIAL WT.)
AIR (100 ml/minute)

| Sample | 150° C. | 200° C. | 250° C. | 300° C. | 350° C. |
|---|---|---|---|---|---|
| EB | 0.31 | 1.26 | 4.10 | 12.34 | 38.67 |
| EBIT | 0.13 | 0.79 | 2.40 | 6.70 | 13.14 |
| EBIT-TETA | 0.50 | 1.06 | 2.53 | 5.07 | 8.90 |

Example F5

Thirty six grams of EB copolymer ($M_n \approx 1.9K$ with 55 wt % ethylene) and 3.6 grams of IT hydrate were combined, and stirred at 160° C. in a nitrogen blanketed reactor for about an hour. The adduct featured an infrared spectrum with a strong carbonyl band at 5.8 microns and an elemental analysis for 2.40% oxygen. Moreover, chromatographic analysis of the adduct indicated that 84.7% of the EB copolymer was functionalized.

The reaction mixture was cooled to about 100° C., and 6 grams of linear triethylene tetramine (TETA) were added gradually over a 2 minute period. Following the addition of the TETA, the mixture was then stirred at 100° C. for about an hour, and rotoevaporated for 2 hours at 80° C. The product displayed an infrared spectrum with a broad absorption band at 5.95 microns, and analyzed for 6.22% nitrogen. Chromatographic analysis indicated that the product contained about 2.6% residual TETA.

Example F6

In similar fashion, 36 grams of EB copolymer ($M_n \approx 1.9K$ with 55 wt % ethylene) and 3.6 grams of IT hydrate were mixed together, and stirred at 155° C. for about 2 hours. The infrared spectrum of a sample of the adduct showed twin carbonyl peaks at 5.7 and 5.8 microns. Chromatographic analysis indicated that 88.2% of the EB polymer was functionalized while elemental analysis revealed that the adduct contained 2.83% oxygen.

Amination of the adduct was effected by the addition of 1.2 grams of ethylene diamine (EDA) to the reactor, followed by stirring the reaction mixture at 80° C. for an hour. Rotoevaporation at 80° C. for 2 hours gave a residue which analyzed for 0.99% nitrogen, and featured an infrared spectrum with a C=N absorption band at 6.15 microns.

Example F7

In similar fashion, 36 grams of the EB copolymer described in Example F6, and 3.6 grams of IT hydrate were combined and heated at 145° C. for about 2 hours to yield an adduct which analyzed for 2.15% oxygen, and featured an IR spectrum with an intense carbonyl band at 5.8 microns. Chromatographic analysis indicated that 87.6 wt % of the polymer was functionalized with IT. The addition of 3.7 grams of linear tetraethylenepentamine (TEPA) to the reaction mixture at 80° C., followed by stirring the mixture at 100° C. for 2 hours, afforded a product which showed an IR spectrum with absorption bands at 5.9 and 6.1 microns, a nitrogen content of 2.74%, and a residual TEPA content of 0.24%.

Example F8

A repeat of Example F7 afforded an EBIT adduct which analyzed for 2.46% oxygen. Chromatographic analysis revealed that 87.6 wt % of the EB polymer was functionalized, and the functionality factor, n=1.14. Following the addition of 1.9 grams of TEPA , the mixture was stirred at 100° C. for about an hour to afford a product which analyzed for 1.68% nitrogen, and 0.081 wt % residual TEPA.

To ascertain the effect of functionality on the thermal oxidative stability of the above dispersant product, the starting EB polymer, the IT-treated EB polymer (adduct), and the TEPA-treated adduct (dispersant product) were submitted for thermogravimetric analysis (TGA).

As indicated above, TGA measures weight loss due to oxidative degradation as the polymers are heated gradually to 350° C. in the presence of air. A comparison of the TGA data shown below in Table 4 for the three polymers clearly indicate that the adduct and dispersant product are significantly more stable than the starting polymer toward thermal oxidative degradation.

TABLE 4

TEMPERATURE RAMPED TGA (10° C./minute)
OF STARTING POLYMER (EB), ADDUCT (EBIT) AND
DISPERSANT PRODUCT (2:1 EBIT-TETA)
CUMULATIVE WEIGHT LOSSES (% OF INITIAL WT.)
AIR (100 ml/minute)

| Sample | 150° C. | 200° C. | 250° C. | 300° C. | 350° C. |
|---|---|---|---|---|---|
| EB | 0.31 | 1.26 | 4.10 | 12.34 | 38.67 |
| EBIT | 0.13 | 0.79 | 2.40 | 6.70 | 13.14 |
| EBIT-TEPA | 0.12 | 1.44 | 2.94 | 5.50 | 9.37 |

Example F9

Forty grams of EB copolymer ($M_n = 2K$ with 55 wt % ethylene) and 3.8 grams of IT hydrate were combined in a dry, nitrogen-blanketed reactor, and stirred at 165° for one hour. The reaction mixture was cooled to 80° C., and 2.9 grams of triethylene tetramine (TETA) were added to the mixture, stirred at 80° C. for about 2 hours. The cooled reaction mixture was diluted with 200 ml of cyclohexane, and filtered. Rotoevaporation of the filtrate gave a residue which analyzed for 1.99% nitrogen, and featured an IR spectrum with a broad band at about 5.9 microns.

Example F10

Forty grams of EB copolymer ($M_n \approx 2K$ with 47 wt % ethylene) were added to a nitrogen blanketed reactor, and stirred at 160° C. while 30 ml of tetrahydrofuran (THF) containing 4 grams of IT hydrate were added dropwise over a half hour period. After addition, the reaction mixture was stirred at 160° C. for 5 hours. Four grams of the mixture were removed from the reactor for analyses. The sample featured an infrared spectrum with a strong carbonyl absorption band at 5.8 microns. The reaction mixture (36 grams) was then stirred at 120° C. while 30 ml of THF containing 4.2 grams of polyamine-H (MW≈234) were added dropwise over a half hour period. Following the addition of the polyamine, the reaction mixture was stirred at 120° C. for about 5 hours, and then rotoevaporated for 8 hours at 120° C. The residue featured an infrared spectrum with a broad carbonyl band at about 5.9 microns, and analyzed for 3.35% nitrogen.

Polymer-AX Adducts

Example G1

Ten grams of polyisobutylene, $M_n \approx 950$, were added to a nitrogen blanketed reactor fitted with a mechanical stirrer, thermometer and condenser. The polyisobutylene was heated to about 150° C. in an oil bath, and 1.6 grams of alloxen monohydrate dissolved in 20 ml of dioxane, were added dropwise to the stirred polymer over a four hour period. After the dioxane solvent distilled off, the reaction mixture was stirred at 150° C. for about ten hours. The cooled reaction mixture was dissolved in about 100 ml of cyclohexane, filtered, and concentrated by rotoevaporation for eight hours at 100° C. The residue analyzed for 1.84% nitrogen, and featured an infrared spectrum with a dominant carbonyl absorption band at about 5.85 microns. Ultraviolet-gel phase chromatography (UV-GPC) analysis showed that the polyisobutylene polymer was uniformly substituted with alloxen, and that the MW distribution of the polyisobutylene was unaffected by ene-modification.

Example G2

About a tenth mole of polyisobutylene ($M_n \approx 2.2K$) was stirred at 155° in a reactor blanketed with nitrogen. A tenth mole (1.7 grams) of sublimed 1,3-dimethylalloxan dissolved in 40 ml of dioxane was added dropwise to the stirred reactor over an hour period. After distilling off the dioxane, the mixture was stirred at 170° C. for about 16 hours, and subsequently rotoevaporated for 8 hours at about 100° C. The residue featured an infrared spectrum with a prominent amide carbonyl absorption band at 5.92 microns, and analyzed for 0.65% nitrogen.

Example G3

A tenth mole of ethylene propylene copolymer with $M_n \approx 2.3K$ and 45 wt % ethylene, was mechanically stirred at 140° C. in a reactor blanketed with nitrogen. A tenth mole of alloxan hydrate dissolved in 50 ml of dioxane was added dropwise over an hour period. The reaction mixture was stirred at 140° C. for about 5 hours, then cooled and diluted with 200 ml of cyclohexane. Filtration and rotoevaporation of the supernatent gave a residue which featured an infrared spectrum with a strong amide absorption band at 5.9 microns, and analyzed for 0.82% nitrogen.

Example G4

A mixture of eleven grams of ethylene propylene copolymer with $M_n \approx 1.1$ and 45 wt % ethylene, 1.6 grams of AX, and 100 ml of dioxane was refluxed for about 6 hours. Rotoevaporation of the mixture at 100° C. for 5 hours afforded a residue which was dissolved in 200 ml of cyclohexane, and filtered. Rotoevaporation of the filtrate gave a residue which showed an infrared spectrum with a strong amide carbonyl absorption band at 5.9 microns, and an elemental analysis for 2.28% nitrogen.

Example G5

Forty grams of EB copolymer ($M_n \approx 2K$ with 55 wt % ethylene), and 2.8 grams of anhydrous AX were combined and stirred at 155° C. for about 2 hours in a nitrogen-blanketed reactor. The clear residue showed an IR spectrum with an intense amide carbonyl band at 5.85 microns, and analyzed for 1.12% nitrogen.

Example G6

Thirty ml of tetrahydrofuran containing 3.2 grams of AX hydrate were added dropwise over a 15 minute period to 40 grams of EB copolymer, $M_n=2K$, stirred at 155° C. After addition, the mixture was again stirred at 155° C. for 2 hours. Rotoevaporation for 2 hours at 100° C. gave a residue which analyzed for 1.30% nitrogen, and featured an IR spectrum with a strong carbonyl absorption band at 5.85 microns. Chromatographic analysis indicated that 73% of the EB polymer was functionalized, and n=1.37.

Example G7

Forty grams of EB copolymer ($M_n \approx 2K$ with 55 wt % ethylene), and 3.4 grams of 1,3-dimethylalloxan were combined and stirred at 165° C. for about 5 hours. Rotoevaporation of the reaction mixture for 2 hours at 100° C. gave a residue which analyzed for 1.22% nitrogen, and featured an IR spectrum with an intense amide carbonyl absorption band at 5.9 microns.

Polymer-AX Products

Example H1

An adduct of poly-alpha-olefin derived from decene-1 ($M_n \approx 2.2$) and AX was prepared by stirring an equimolar (0.05 mole) mixture of the reactants at 160° C. for 5 hours. After sampling the reaction mixture, 5.8 grams (0.04 mole) of TETA were added to the remaining adduct (ca. 0.04 mole), and the reaction mixture was stirred at 120° C. for about 6 hours. Rotoevaporation of the mixture produced a residue featuring an infrared spectrum with a broad amide carbonyl absorption band at 5.9 microns, and analyzing for 1.18% nitrogen.

Example H2

Forty grams of EB copolymer ($M_n \approx 2K$ with 55 wt % ethylene) and 3.2 grams of AX hydrate are combined and stirred at 165° C. for about 2 hours in a nitrogen-blanketed reactor. The reaction mixture features an IR spectrum with an intense amide carbonyl absorption band at 5.8 microns ascribable to the ene adduct. The reaction mixture is cooled to 60° C., and 2.9 grams of TETA is added, and the reaction mixture is stirred at 80° C. for about 2 hours. The mixture is then diluted with 200 ml of cyclohexane, and filtered. Rotoevaporation of the supernatent for 6 hours at 80° C. afforded a residue which showed an IR spectrum with a broad amide carbonyl absorption at 5.9 microns. The amide product analyzed for 2.73% nitrogen, and 0.16% residual TETA.

Example H3

In like manner, 40 grams of EB copolymer described in Example H2, and 3.2 AX hydrate were combined, and stirred at 165° C. for about 2 hours in a nitrogen-blanketed reactor. The mixture was cooled, and 2.9 grams of TETA were added, and stirring was continued at 165° C. for about 2 hours. The reaction mixture was diluted with 200 ml of cyclohexane, and filtered. Rotoevaporation of the filtrate for 2 hours at 100° C. gave a residue which analyzed for 2.97% nitrogen, and featured an IR spectrum with an amide carbonyl absorption band at 5.95 microns.

Example H4

In like manner, forty grams of EB copolymer of Example H2 were functionalized with 3.2 grams of AX hydrate. The IR sprectrum of the adduct featured an intense amide carbonyl absorption band at 5.8 microns. The macrocyclic amidoamine product was formed by combining the adduct with 3 grams of bis-(2-aminoethyl)-1,3-propanediamine (BAP) at 80° C. for 2 hours. The reaction mixture was diluted with 200 ml of cyclohexane, filtered, and then concentrated by roto-evaporation at 80° C. for 2 hours. The residue showed an IR with a broad band centered at 6 microns, and analyzed for 2.73% nitrogen, and 0.14% residual BAP.

Example H5

In like manner forty grams of EB copolymer of Example H2, and 3.4 grams of 1,3-dimethylalloxan were combined and stirred at 165° C. for about 5 hours in a nitrogen blanketed reactor. A sample of the adduct featured an IR with a strong carbonyl absorption band at 5.9 microns. Amination of the adduct was effected by adding 2.9 grams of TETA to the reactor, and stirring the mixture at 80° C. for about 2 hours. The reaction mixture was then diluted with 200 ml of cyclohexane, and filtered. Rotoevaporation of the filtrate at 80° C. for 3 hours gave a residue which analyzed for 2.28% nitrogen, and featured an IR spectrum with an amide carbonyl absorption band at 5.95 microns.

Dispersant Activity of Polyamine-Treated Adducts

Example I

The products of Examples F4, F5, F9, H2, H3, H4 and H5 were then tested for sludge inhibition properties via the SIB test and varnish inhibition properties via the VIB test.

The SIB test has been found, after a large number of evaluations, to be an excellent test for assessing the dispersing power of lubricating oil dispersant additives.

The medium chosen for the SIB test was a used crankcase mineral lubricating oil composition having an original viscosity of about 325 SUS at 38° C. that had been used in a taxicab that was driven generally for short trips only, thereby causing a buildup of a high concentration of sludge precursors. The oil that was used contained only a refined base mineral lubricating oil, a viscosity index improver, a pour point depressant and zinc dialkyldithiophosphate anti-wear additive. The oil contained no sludge dispersant. A quantity of such used oil was acquired by draining and refilling the taxicab crankcase at 1000–2000 mile intervals.

The SIB test is conducted in the following manner: The aforesaid used crankcase oil, which is milky brown in color, is freed of sludge by centrifuging for one hour at about 39,000 gravities (gs.). The resulting clear bright red supernatant oil is ten decanted from the insoluble sludge particles thereby separated out. However, the supernatant oil still contains oil-soluble sludge precursors which on heating under the conditions employed by this test will tend to form additional oil-insoluble deposits of sludge. The sludge inhibiting properties of the additives being tested are determined by adding to portions of the supernatant used oil, a small amount, such as 0.5, 1 or 2 weight percent, of the particular additive being tested.

Ten grams of each blend being tested are placed in a stainless steel centrifuge tube and are heated at 135° C. for 16 hours in the presence of air. Following the heating the tube containing the oil being tested is cooled and then centrifuged for about 30 minutes at room temperature at about 39,000 gs. Any deposits of new sludge that form in this step are separated from the oil by decanting the supernatant oil and then carefully washing the sludge deposits with 25 ml of heptane to remove all remaining oil from the sludge and further centrifuging. The weight of the new solid sludge that has been formed in the test, in milligrams, is determined by drying the residue and weighing it.

The results are reported as amount of precipitated sludge in comparison with the precipitated sludge of a blank not containing any additional additive, which blank is normalized to a rating of 10. The less new sludge precipitated in the presence of the additive, the lower the SIB value and the more effective is the additive as a sludge dispersant. In other words, if the additive gives half as much precipitated sludge as the blank, then it would be rated 5.0, since the blank will be normalized to 10.

The VIB test was used to determine varnish inhibition. Here, each test sample consisted of 10 grams of lubricating oil containing a small amount of the additive being tested. The test oil to which the additive is ad-mixed is of the same type as used in the above-described SIB test. Each 10 gram sample was heat soaked over night at about 140° C. and thereafter centrifuged to remove the sludge. The supernatant fluid of each sample was subjected to heat cycling from about 150° C. to room temperature over a period of 3.5 hours at a frequency of about 2 cycles per minute. During the heating phase, gas which was a mixture of about 0.7 volume percent $SO_2$, 1.4 volume percent NO and balance air was bubbled through the test samples. During the cooling phase water vapor was bubbled through the test samples.

At the end of the test period, which testing cycle can be repeated as necessary to determine the inhibiting effect of any additive, the wall surfaces of the test flasks in which the samples were contained are visually evaluated as to the varnish inhibition. The amount of varnish imposed on the walls is rated to values of from 1 to 11 with the higher number being the greater amount of varnish, in comparison with a blank with no additive that was rated 11.

Ten grams of SIB test oil were mixed with 0.025 or 0.05 grams of the products of Examples and tested in the above described SIB and VIB tests. The test results are summarized below in Table 5.

TABLE 5

SLUDGE INHIBITION AND VARNISH INHIBITION BENCH TEST (SIB AND VIB) RESULTS

| Additive | SIB | VIB | % N[a] | % a.i.[b] |
|---|---|---|---|---|
| Example F9 [1:1] .05 g | 0.0[c] | 3 | 1.04 | 55.8 |
| Example F9 [1:1] .025 g | 0.9 | 3+ | 1.04 | 55.8 |
| Example F5 [1:2] .05 g | 0.0 | 3 | 3.40 | 56.2 |
| Example F4 [1:0.5] .05 g | 0.0 | 4 | 0.81 | 54.7 |
| Example H2 [1:1] .05 g | 0.0 | 3 | 1.42 | 44.1 |
| Example H5 [1:1] .05 g | 0.0 | 4 | 1.11 | 45.8 |
| Example H3 [1:1].05 g | 1.7 | 4 | 1.72 | 32.3 |
| Example H4 [1:1] .05 g | 0.0 | 4 | 1.41 | 29.3 |
| Standard A[d] .05 g | 4.1 | 5 | 0.88 | 49.4 |
| Standard B[e] .05 g | 7.3 | 7 | 1.51 | 52.0 |
| Blank | 14.5 | | | |

[a]Analysis for dispersants in S150N mineral oil
[b]Active ingredient determined by chromatography
[c]Milligrams sludge.
[d]Standard A is a high MW commerical polyamine substituted polyisobutylene ($M_n$ = 2250) succinimide.
[e]Standard B is a low MW commercial polyamine substituted polyisobutylene ($M_n$ = 950) succinimide.

As shown by the above test data in Table 5, the additives of Examples F9, F5, F4, H2, H5, H3 and H4 featured outstanding results in varnish inhibition and sludge dispersing ability compared with the high and low MW commercial dispersants, standards A and B, respectively.

Post-Products

Boration

Example J1

Two grams of the product of Example F4 dissolved in 6 ml of tetrahydrofuran (THF) and 70 mg of boric acid were combined and stirred at 100° for 24 hours. Rotoevaporation of the filtered reaction mixture afforded the borated product.

Example J2

About a tenth mole (23.4 grams) of Polyamine-H (a commercial polyamine composed primarily of ethyleneamines heavier than TEPA with the PEHA cut left in the product, and analyzing for 33% nitrogen) was stirred at 120° C. in a 250 ml beaker, while 12.4 grams of boric acid were added in gram portions over a 5 minute period. The mixture was stirred at 120° C. for about an hour, or until a clear solution was obtained. The clear, amber-colored PAM metaborate (PMB) reagent analyzed for 6.05% boron and 23.29% nitrogen.

Example J3

About 36 grams of EB copolymer ($M_n \approx 1.8K$ and 55% ethylene) and 4 grams of IT hydrate were stirred at 160° C. for 8 hours in a nitrogen-blanketed reactor. Chromatographic analysis of a 6 gram sample indicated that 83.9% of the EB polymer was functionalized. The remainder of the reaction mixture, which was stirred at about 140° C., was treated with 1.8 grams of PMB described in Example J2. After PMB addition, the mixture was stirred at 140° C. for about 2 hours and subsequently diluted with 24 grams of S150N mineral oil. A sample of the product analyzed for 0.75% nitrogen, and 0.11% boron. Chromatographic analysis confirmed that the product contained 49.6% active ingredient.

Example J4

One hundred grams of ethylene butene-1 (EB) copolymer ($M_n \approx 3.2K$ and 55 wt % ethylene), and 6 grams of anhydrous IT were combined and stirred at 160° C. for 24 hours. To boraminate the resulting adduct, EBIT, a TEPA-metaborate reagent was prepared by heating 18.9 grams of TEPA in a 100 ml beaker, and adding 12.4 grams of boric acid in small portions to the TEPA over an 15 minute period. The mixture was stirred at 120° C. for about 1 hour until the boric acid underwent dehydration to the metaborate and dissolved in the TEPA to form a clear, amber-colored liquid (TEPA-MBA).

The reaction mixture containing the EBIT was diluted with 40 grams of S150N mineral oil to facilitate stirring at 140° C., and then treated with 6.3 grams of TEPA-MBA prepared above. The mixture was stirred at 140° C. for an hour while a mild flow of nitrogen over the reaction surface removed water from the reactor. Twenty two more grams of S150N mineral oil were added to make a ca. 50% oil solution of the bor-aminated EBIT product. The oil solution of EBIT-TEPA-MBA dispersant analyzed for 0.81% nitrogen and 0.26% boron.

Example J5

In a similar manner, 100 grams of EB ($M_n \approx 3.2$), and 6.2 grams of IT hydrate were combined and stirred at 155° C. for about 5 hours to give a clear rust-colored adduct which analyzed for 1.34% oxygen. Chromatographic analysis of a ten gram sample of the reaction mixture indicated that 72.5% of the polymer was functionalized; the functionality factor, n=1.38. The adduct, EBIT, was bor-aminated by adding 5.33 grams of TEPA-MBA to the EBIT, and stirring the resulting mixture at 130° C. for about 3 hours to effect complete bor-amination. After adding 50 grams of S150N mineral oil to obtain a ca. 50% oil solution of the product, the diluted solution was stirred for 2 hours at 140° C. Rotoevaporation at 100° C. for 4 hours gave a S150N mineral oil solution of the TEPA-MBA treated EBIT which analyzed for 0.84% nitrogen, and 0.20% boron.

Acylation

Example J6

Typically, one mole equivalent of an acylating agent such as ethyl acetate, ethyl acetoacetate, butyrolactone, or 2,4-pentadione is added to one or more basic NH and/or $NH_2$ groups in the dispersant by heating the aminated adduct with the acylating agent at 120° C. until IR analysis indicates complete reaction.

Salt Formation

The addition of thiosulfuric acid (TSA) and thiophosphoric acid (TPA) to polyamine-treated adducts 1c, 2c, and 3c affords salt derivatives with antioxidant properties, and enhanced seal compatibility properties. A synthetic option to TSA and TPA involves the use of the corresponding ammonium salts, $(NH_4)_2S_2O_3$ and $(NH_4)_2HPSO_3$, in place of the respective thio acids.

TSA and TPA-Treated Additives

Example J7

Typically, sufficient amounts of TSA and/or TPA are added directly to the polyamine-treated adducts to form salts via neutralization of one or more basic nitrogen sites present in the additive or dispersant. For example, an amine-treated adduct and sufficient TSA and/or TPA are stirred at about 80° C. for 4 hours to effect salt formation.

Example J8

Four grams of the EBIT-TETA product of Example F4 and 250 mg of ammonium thiosulfate were combined and stirred at 100° C. for 48 hours. Rotoevaporation of the mixture at 80° for 4 hours afforded a residue which corresponds to the thiosulfate salt of the EBIT PAM dispersant.

High MW Polymer-IT Adducts

Example K1

Ten grams of ethylene propylene ethylidene norbornene terpolymer ($M_n \approx 55K$, containing about 43 wt % propylene, and 5 wt. % 2-ethylidene-5-norbornene) were dissolved in 90 grams of xylene at 100° C., and poured into a nitrogen-blanketed reactor fitted with a mechanical stirrer, and reflux condensor. Using a silicone oil bath, the reactor was heated to 120° C. and a half gram IT hydrate dissolved in 10 ml of dioxane was added dropwise to the reactor. The reaction mixture was stirred at 120° C. for about 6 hours, and at 140° C. for 15 hours. The functionalized polymer was precipitated by addition of the cooled reaction mixture to a liter of acetone. The dried polymer analyzed for 0.94% oxygen, and featured an infrared spectrum (film) with an intense carbonyl absorption band at about 5.8 microns. GPC analysis showed that ene functionalization with IT monomer did not affect the molecular weight distribution of the terpolymer.

Example K2

Ten grams of the terpolymer described in Example K1 were dissolved in 90 grams of o-dichlorobenzene at 100° C., and poured into a nitrogen-blanketed reactor fitted with a mechanical stirrer, and reflux condensor. Using a silicone oil bath, the reactor was heated to 130° C. and 1 gram of IT hydrate was added in one portion. Dissolution of the IT monomer produced a green-colored solution which was stirred at 130° C. for about 5 hours. The reaction mixture was added to a liter of acetone causing the functionalized polymer to separate from solution. The dried polymer featured an IR spectrum (film) with an intense carbonyl absorption band at 5.8 microns, and analyzed for 2.16% oxygen.

Example K3

Ten grams of ethylene propylene ethylidene norbornene terpolymer ($M_n \approx 55K$, containing about 43 wt % propylene, and 9 wt. % ethylidene norbornene) were dissolved in 90 grams of xylene at 60° C., and charged into a nitrogen-blanketed reactor fitted with a mechanical stirrer, and reflux condensor. Using a silicone oil bath, the reactor was heated to 120° C. and a half gram of IT hydrate dissolved in 10 ml of dioxane was added dropwise to the reactor. The reaction mixture was stirred at 120° for about 6 hours, and then refluxed for 24 hours. The functionalized polymer was precipitated by addition of the cooled reaction mixture to a liter of acetone, and redissolved into 200 ml of cyclohexane, and re-precipitated from a liter of acetone. The dried polymer analyzed for 2.73% oxygen, and featured an infrared spectrum (film) with an intense carbonyl absorption band at about 5.8 microns.

Example K4

Polyolefins can be modified in bulk, or in the melt quickly and conveniently by simply adding a carbonyl monomer such as IT to the unsaturated polymer in an extruder or in this case a Braebender mixer in the range of about 100° C. to about 220° C. for 1 to 15 minutes.

A typical synthetic protocol follows:

A 55 gram sample of terpolymer described in Example K1 is introduced into a Braebender mixer at about 170° C., and mixed for several minutes to attain reaction temperature. Then, a gram of IT hydrate is added in several portions in the span of a minute, using moderate mixing conditions (40 RPM). The formation of anhydrous IT colors the polymer mass a vibrant purplish blue color, which in 1 to 2 minutes changes to a golden yellow color indicating that the ene addition of IT to the polymer is complete. The functionalized polymer dissolves completely in cyclohexane indicating that crosslinking did not occur under the experimental conditions used for melt functionalization. Addition of the polymer solution to a large volume of acetone precipitates the polymer which is redissolved in cyclohexane, and reprecipitated again from acetone. The dried polymer analyzes for 0.70% oxygen, and features an IR spectrum (film) with an intense carbonyl band at 5.8 microns. Repeating this synthetic protocol using 2, 3, and 4 grams of IT hydrate afforded twice precipitated and dried polymers which analyzed for 1.02%, 1.50%, and 2.08% oxygen, respectively. In all instances, the functionalized polymers dissolved completely into cyclohexane, indicating that no crosslinking had occurred. GPC analysis showed that the MW distribution of the polymer did not change after functionalization with IT. Similar results were obtained in a Banberry mixer.

Example K5

Melt functionalization of a styrene butadiene diblock copolymer ($M_n \approx 70K$ with 25 wt % styrene) was carried out in the following manner.

Fifty five grams of the copolymer were combined with 3 grams of IT in a Braebender mixer at 160° C. for seven minutes. The melt was initially bluish-purple colored upon the addition of IT but within 2–3 minutes the melt turned a clear, amber color. The functionalized polymer was dissolved in cyclohexane, and precipitated from acetone, and dried. The dry polymer analyzed for 1.50% oxygen (Theory requires 1.47% oxygen), and featured an IR spectrum with a carbonyl absorption band at 5.8 microns.

Example K6

Ten grams of a partially hydrogenated star branched polyisoprene polymer ($M_n \approx 280K$) and 90 grams of dichlorobenzene were combined and stirred at 145° C. in a nitrogen-blanketed reactor until the polymer dissolved. A gram of sublimed IT was added to the reactor, and the mixture was stirred at 145° C. for about 12 hours. The reaction mixture was added to a liter of acetone to precipitate the functionalized polymer which was then redissolved in cyclohexane, and reprecipitated from acetone. The dried polymer featured an IR with a strong carbonyl absorption band at 5.75, and analyzed for 1.24% oxygen.

Example K7

Ten grams of the polymer described in Example K6, and 90 grams of toluene were combined in a nitrogen blanketed reactor, and stirred at reflux until dissolution of the polymer occurred. At that point, 0.25 gram of anhydrous IT was added, and the mixture refluxed for seven hours. The mixture was added to a liter of acetone to precipitate the functionalized polymer which was dissolved in cyclohexane, and re-precipitated from acetone. The dried polymer analyzed for 0.59% oxygen, and displayed a carbonyl absorption band at 5.8 microns in the infrared. The GPC traces of the starting polymer and the IT-modified polymer were comparable.

High MW Polymer-IT products (MFVI's)

Example L1

Ten grams of styrene butadiene radial copolymer ($M_n \approx 215K$ with 30 wt % styrene) were dissolved in 90 grams of xylene at 80° C. A half gram of anhydrous IT was added and the reaction mixture was stirred at reflux for about an hour. The mixture was added to a liter of acetone to precipitate the functionalized polymer. The IR spectrum of the dried polymer featured a strong carbonyl band at 5.8 microns. An infrared spectral study shows that the reaction of IT-modified polymer with an excess of 3-(dimethylamino) propylamine (DMAP) in refluxing xylene produces a C=N absorption band at 6.0 microns which grows at the expense of the 5.8 micron band ascribable to the IT-adduct. The isolated and dried aminated IT adduct analyzed for 0.40% nitrogen.

Example L2

In accord with Example K7, 10 grams of star polymer were functionalized with 0.5 gram of anhydrous IT via reaction at 145° C. for 4 hours in 90 grams of dichlorobenzene. Three grams of DMAP were added, and the mixture was heated at 100° C. for about 10 hours. The aminated polymer was recovered by precipitation from acetone, and after drying, analyzed for 0.37% nitrogen.

Example L3

Ten grams of star polymer described in Example K6 and 90 grams of toluene were combined in a nitrogen blanketed reactor, and stirred at reflux until dissolution of the polymer occurred. At that point, 0.25 gram of anhydrous IT was added, and the mixture refluxed for 12 hours. After removing 10 ml of the reaction mixture for analysis, two grams of DMAP were added, and the mixture was refluxed for 12 hours. The reaction mixture was diluted with 70 grams of S100N mineral oil, and rotoevaporated at 100° C. for 8 hours. The aminated polymer analyzed for 0.26% nitrogen.

Example L4

The present example demonstrates that a multi-functional viscosity modifier can be designed in a Braebender mixer.

Fifty grams of terpolymer described in Example K1 is introduced into a Braebender mixer at about 150° C., and mixed for several minutes to attain reaction temperature. Then, 1.1 gram of IT hydrate is added in several portions in the span of a minute, using moderate mixing conditions (40 RPM). The formation of anhydrous IT colors the polymer mass a vibrant purplish blue color, which in 1 to 2 minutes changes to a golden yellow color indicating that the ene addition of IT to the polymer is complete. At this juncture, 0.8 gram of N-(3-aminopropyl) morpholine (NAPM) is added in two doses over a minute period. The functionalized polymer is removed from the mixer after one minute, dissolved in cyclohexane, and precipitated from acetone. The dried polymer analyzes for 0.11% nitrogen. Repeating this procedure with 1.6 grams of NAPM affords a functional polymer which analyzes for 0.22% nitrogen. No crosslinking was detected during polymer functionlization; moreover, upon standing for over a month, mineral oil solutions of the NAPM-treated polymer showed no signs of increased thickening.

Example L5

Ten grams of terpolymer described in Example K1 were dissolved in 90 grams of xylene at 100° C., and poured into a nitrogen-blanketed reactor fitted with a mechanical stirrer, and reflux condensor. Using a silicone oil bath, the reactor was heated to 120° C. and 0.25 gram of IT hydrate dissolved in 10 ml of dioxane was added dropwise to the reactor. The reaction mixture was stirred at about 140° C. for about 16 hours. A sample of the precipitated polymer featured an IR spectrum (film) with a strong carbonyl band at 5.8 microns.

Then, two grams of DMAP were added to the reaction mixture stirred at 80° C. for 24 hours, at 100° C. for 24 hours, and at 125° C. for about 18 hours. A thirty gram sample of the reaction mixture was diluted with 17 grams of S150N mineral oil, and the xylene was removed by rotoevaporation at 120° C. for about 16 hours. The mineral oil solution of the functionalized polymer (12% active ingredient by chromatography) analyzed for 0.30% nitrogen, and featured an IR spectrum with a broad absorption band at about 6 microns.

High MW Polymer-Ax Adducts

Example M1

Ten grams of terpolymer described in Example K1 were dissolved in 90 grams of S150N mineral oil at 100° C., and charged into a nitrogen-blanketed reactor fitted with a mechanical stirrer, and reflux condensor. Using a silicone oil bath, the reactor was heated to 140° C. and one gram of AX hydrate dissolved in 35 ml dioxane was added dropwise to the xylene solution of the terpolymer. The reaction mixture was then stirred at 120° C. for about 22 hours. The functionalized polymer was precipitated by addition of about 20 ml of the reaction mixture to a half liter of acetone, and redissolved in cyclohexane, and reprecipitated from acetone. The dried polymer analyzed for 0.36% nitrogen, and featured an infrared spectrum (film) with an intense carbonyl absorption band at about 5.9 microns.

Example M2

Forty grams of styrene butadiene linear copolymer ($M_n \approx 68K$ with 28 wt % styrene) were dissolved in 160 grams of xylene at 80° C. The polymer solution was stirred at reflux while 3 grams of anhydrous AX dissolved in 40 ml of tetrahydrofuran (THF) were added dropwise over a half hour. After the THF boiled off, the reaction mixture was stirred at reflux for about 24 hours. The functionalized polymer was isolated by adding the reaction mixture to a liter of acetone. The polymer was dissolved in cyclohexane, and precipitated from acetone. The dried polymer analyzed for 1.41% nitrogen and featured an IR spectrum with a strong carbonyl band at 5.9 microns.

High MW Polymer-AX Products (MFVI's)

Example N1

Ten grams of star polymer described in Example K6 and 90 grams of toluene were combined in a nitrogen purged reactor, and stirred at reflux until dissolution of the polymer occurred. At that point, 0.25 gram of anhydrous 1,3-dimethylalloxan was added, and the mixture refluxed for 24 hours. After removing 10 ml of the reaction mixture for analysis (the adduct featured an IR with a strong imide carbonyl band at 5.9 microns), two grams of DMAP were added, and the mixture was refluxed for 36 hours. The functionalized polymer was precipitated from acetone, and after drying, analyzed for 0.39% nitrogen and featured an IR (film) with carbonyl bands at 5.5 and 5.7 microns.

Example N2

Ten grams of terpolymer described in Example K1 were dissolved in 90 grams of hot xylene contained a nitrogen-blanketed reactor fitted with a mechanical stirrer, and reflux condensor. A half gram of anhydrous 1,3-dimethylalloxan was added, and the reaction mixture was stirred at 140° C. for about 24 hours. The functionalized polymer was precipitated by addition of about 20 ml of the reaction mixture to a half liter of acetone, re-dissolved in cyclohexane, and re-precipitated from acetone. The dried polymer analyzed for 0.41% nitrogen, and featured an infrared spectrum (film) with an intense carbonyl absorption band at about 5.9 microns.

Two grams of DMAP were added, and the mixture was stirred at 60° C. for 8 hours, and at 100° C. for 24 hours. The addition of a 30 ml sample of the reaction mixture to a half liter of acetone precipitated the functionalized polymer which was dissolved in cyclohexane, and reprecipitated from acetone. The dried polymer analyzed for 0.42% nitrogen, and featured an IR spectrum (film) with carbonyl absorption bands at 5.5 and 5.7 microns.

What is claimed is:

1. A product formed by reacting (a) an adduct of a hydrocarbyl and a vicinal polycarbonyl compound having three or more carbonyl groups, the adduct having a value of greater than 1, wherein n is the average number of vicinal polycarbonyl compounds incorporated per adduct, with (b) a reagent, wherein said reagent comprises a nucleophile selected from the group consisting of polyamines, polyols, amino alcohols and mixtures thereof.

2. The product according to claim 1, wherein the product is post-treated with an electrophilic reagent.

3. The product according to claim 2, wherein the electrophilic reagent comprises a boron-oxygen compound.

4. A composition comprising a major amount of a base oil and a minor mount of a product formed by reacting (a) an adduct of a hydrocarbyl and at least one vicinal polycarbonyl compound having three or more carbonyl groups, the adduct having a value of n greater than 1, wherein n is the average number of vicinal polycarbonyl compounds incorporated per adduct, with (b) a reagent, wherein said regent comprises a member selected from nucleophiles, electrophiles, metal salts and metal complexes.

5. A composition comprising a major amount of base oil and a minor amount of a reaction product of an adduct having the formula selected from 1c, 2c and 3c:

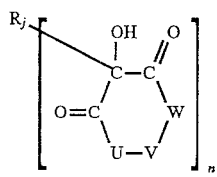  [1c]

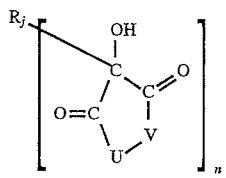  [2c]

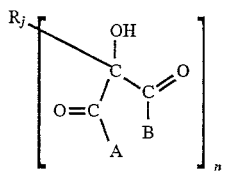  [3c]

wherein $R_j$ is selected from the group consisting of saturated and unsaturated hydrocarbyl groups containing about 8 to about 40 carbon atoms and polyalkyl and polyalkenyl groups of Mn of about 500 to about 10 million, and wherein $R_j$ optionally contains one or more polar substituents; n is greater than 1; U, V and W are independently selected from the group consisting of C=O, C=NH, C=NR$_g$, O, NH, NR$_g$, S, CHR$_g$, C(R$_g$)$_2$ and CHCHOHCH$_2$OH; U and V may be selected such that U+V=1,2-phenylene, napthalene-1, 2-diyl, and 1,2-dihydroxy-ethylene-1,2-diyl; A and B are independently selected from OH, OR$_g$, N(R$_g$)$_2$, COOH, COOR$_g$, and R$_g$ wherein R$_g$ is selected independently from the group consisting of alkyl radicals having 1 to about 18 carbon atoms, and aryl radicals; and a reagent wherein said reagent comprises a member selected from nucleophiles, electrophiles, metal salts and metal complexes.

6. The composition according to claim 5, wherein the adduct comprises a radical adduct and Rj comprises a polyalkyl group.

7. The composition according to claim 5, wherein the adduct comprises an ene adduct and Rj comprises a polyalkenyl group.

8. The composition according to claim 7, wherein the polyalkenyl group has a number average molecular weight of from about 500 to 20,000.

9. The composition according to claim 7, wherein the polyalkenyl group has a number average molecular weight of from about 20,000 to 200,000.

10. A process for preparing a bor-aminated product which comprises treating an adduct of a hydrocarbon and at least one vicinal polycarbonyl compound having three or more carbonyl groups with a liquid polyamine metaborate, the polyamine metaborate prepared by heating boric acid in a mixture with polyamine.

11. A bor-aminated product prepared by the process according to claim 10.

* * * * *

UNITED STATES PATENT AND TRADEMARK OFFICE
CERTIFICATE OF CORRECTION

PATENT NO. : 5,646,098
DATED : July 8, 1997
INVENTOR(S) : Stanley J. Brois

It is certified that error appears in the above-indentified patent and that said Letters Patent is hereby corrected as shown below:

In column 75, claim 1, line 2, before the word "greater" insert --n--.

In column 75, claim 4, line 12, delete the word "mount" and insert therefore --amount--.

In column 75, claim 4, line 17, delete the word "regent" and insert therefore --reagent--.

In column 76, claim 5, line 11, delete the word "napthalene" and insert therefore --naphthalene--.

Signed and Sealed this

Thirtieth Day of September, 1997

Attest:

BRUCE LEHMAN

Attesting Officer

Commissioner of Patents and Trademarks